(12) United States Patent
Bian et al.

(10) Patent No.: US 10,376,555 B2
(45) Date of Patent: Aug. 13, 2019

(54) IDENTIFICATION OF CYCLIC PEPTIDE AGONISTS OF GALANIN RECEPTOR 2 AND 3 GUIDED BY SPEXIN SOLUTION STRUCTURE

(71) Applicant: Hong Kong Baptist University, Hong Kong (HK)

(72) Inventors: Zhaoxiang Bian, Hong Kong (HK); Tao Huang, Hong Kong (HK); Chengyuan Lin, Hong Kong (HK)

(73) Assignee: Hong Kong Baptist University, Hong Kong (HK)

( * ) Notice: Subject to any disclaimer, the term of this patent is extended or adjusted under 35 U.S.C. 154(b) by 0 days.

(21) Appl. No.: 15/925,949

(22) Filed: Mar. 20, 2018

(65) Prior Publication Data
US 2018/0289766 A1    Oct. 11, 2018

Related U.S. Application Data

(60) Provisional application No. 62/482,751, filed on Apr. 7, 2017, provisional application No. 62/506,654, filed on May 16, 2017.

(51) Int. Cl.
| | |
|---|---|
| *C07K 5/12* | (2006.01) |
| *C07K 7/08* | (2006.01) |
| *A61K 38/10* | (2006.01) |
| *A61K 38/12* | (2006.01) |
| *A61K 38/02* | (2006.01) |
| *A61K 38/22* | (2006.01) |
| *A61K 38/00* | (2006.01) |
| *A61K 38/17* | (2006.01) |
| *A61K 9/00* | (2006.01) |
| *A61P 3/04* | (2006.01) |

(52) U.S. Cl.
CPC ............ *A61K 38/02* (2013.01); *A61K 9/0019* (2013.01); *A61K 38/005* (2013.01); *A61K 38/1796* (2013.01); *A61K 38/22* (2013.01); *A61P 3/04* (2018.01)

(58) Field of Classification Search
CPC .......... C07K 5/12; C07K 7/08; A61K 38/005; A61K 38/10; A61K 38/12; A61K 38/02; A61K 38/1796; A61K 38/22; A61K 9/0019; A61P 3/04
See application file for complete search history.

(56) References Cited

U.S. PATENT DOCUMENTS

| | | | | |
|---|---|---|---|---|
| 8,435,940 B2 * | 5/2013 | Bulaj | ............... | C07K 5/1019 514/5.2 |
| 9,057,726 B2 * | 6/2015 | Leroy | ............... | G01N 33/566 |
| 2004/0234537 A1 * | 11/2004 | Bougueleret | ............... | C07K 14/47 424/185.1 |
| 2009/0281031 A1 * | 11/2009 | Bulaj | ............... | C07K 5/1019 514/1.1 |
| 2013/0196348 A1 | 8/2013 | Leroy | | |

FOREIGN PATENT DOCUMENTS

| | | |
|---|---|---|
| CN | 101448513 A | 6/2009 |
| CN | 103391784 A | 11/2013 |
| WO | 2016146513 A1 | 9/2016 |

OTHER PUBLICATIONS

Freimann et al.; Galanin receptors as a potential target for neurological disease; Expert Opinion on Therapeutic Targets; 2015; vol. 19, Issue 12; pp. 1665-1676; Informa (United Kingdom).

Lang et al.; Physiology, Signaling, and Pharmacology of Galanin Peptides and Receptors: Three Decades of Emerging Diversity; Pharmacological Reviews; 2015; vol. 67, Issue 1; pp. 118-175; The American Society for Pharmacology and Experimental Therapeutics.

Lang et al.; The galanin peptide family in inflammation; Neuropeptides; 2011; vol. 45, Issue 1; pp. 1-8; Elsevier.

Webling et al.; Galanin receptors and ligands; Frontiers in endocrinology; 2012; vol. 3; Article 146; Frontiers Media.

Mirabeau et al.; Identification of novel peptide hormones in the human proteome by hidden Markov model screening; Genome research; 2007; vol. 17, Issue 3; pp. 320-327; Cold Spring Harbor Laboratory Press.

Porzionato et al.; Spexin expression in normal rat tissues; The journal of histochemistry and cytochemistry : official journal of the Histochemistry Society; 2010; vol. 58, Issue 9; pp. 825-837; SAGE Publications.

Rucinski et al.; Expression of the spexin gene in the rat adrenal gland and evidences suggesting that spexin inhibits adrenocortical cell proliferation; Peptides; 2010; vol. 31, Issue 4; pp. 676-682; Elsevier.

Porzionato et al.; Spexin is expressed in the carotid body and is upregulated by postnatal hyperoxia exposure; Advances in experimental medicine and biology; 2012; vol. 758; pp. 207-213; Springer.

Gu et al.; Spexin peptide is expressed in human endocrine and epithelial tissues and reduced after glucose load in type 2 diabetes; Peptides; 2015; vol. 71; pp. 232-239; Elsevier.

Lin et al.; Spexin Enhances Bowel Movement through Activating L-type Voltage-dependent Calcium Channel via Galanin Receptor 2 in Mice; Scientific Reports; 2015; vol. 5, Article 12095; Nature Publishing Group.

Toll et al.; Peptides derived from the prohormone proNPQ/spexin are potent central modulators of cardiovascular and renal function and nociception; FASEB Journal; 2012; vol. 26, Issue 2; pp. 947-954; The Federation of American Societies for Experimental Biology.

(Continued)

*Primary Examiner* — Julie Ha
(74) *Attorney, Agent, or Firm* — Spruson & Ferguson (Hong Kong) Limited

(57) ABSTRACT

Cyclic peptide agonists toward human galanin receptor 2 (GalR2) and galanin receptor 3 (GalR3) based on hidden conformation of spexin solution structure for GalR2 and GalR3-related and spexin-deficient disorders are designed and synthesized. LH101, LH102, and LH101 (Ac) are potent spexin analogs with prolonged action, which can be used in the treatment of GalR2 and GalR3-related diseases and spexin-deficient disorders, such as obesity.

19 Claims, 63 Drawing Sheets

Specification includes a Sequence Listing.

(56) References Cited

OTHER PUBLICATIONS

Liu et al.; A novel neuropeptide in suppressing luteinizing hormone release in goldfish, Carassius auratus; Molecular and cellular endocrinology; 2013; vol. 374, Issues 1-2; pp. 65-72; Elsevier.

Wong et al.; Goldfish spexin: solution structure and novel function as a satiety factor in feeding control; The American Journal of Physiology; Endocrinology and Metabolism; 2013; vol. 305, Issue 3; pp. E348-E366; American Physiological Society.

Walewski et al.; Spexin Is a Novel Human Peptide that Reduces Adipocyte Uptake of Long Chain Fatty Acids and Causes Weight Loss in Rodents with Diet-Induced Obesity; Obesity; 2014; vol. 22, Issue 7; pp. 1643-1652; Wiley.

Kumar et al.; Decreased Circulating Levels of Spexin in Obese Children; The Journal of clinical endocrinology and metabolism; 2016; vol. 101, Issue 7; pp. 2931-2936; The Endocrine Society.

Ge et al.; Regulation of Hepatocellular Fatty Acid Uptake in Mouse Models of Fatty Liver Disease with and without Functional Leptin Signaling: Roles of NfKB and SREBP-1C and the Effects of Spexin; Seminars in liver disease; 2016; vol. 36, Issue 4; pp. 360-372; Thieme Medical Publishers, Inc.

Kim et al.; Coevolution of the spexin/galanin/kisspeptin family: Spexin activates galanin receptor type II and III; Endocrinology; 2014; vol. 155, Issue 5; pp. 1864-1873; The Endocrine Society.

Tyndall et al.; Over one hundred peptide-activated G protein-coupled receptors recognize ligands with turn structure; Chemical reviews; 2005; vol. 105, Issue 3; pp. 793-826; ACS Publications.

Ruiz-Gomez G et al.; Update 1 of: Over one hundred peptide-activated G protein-coupled receptors recognize ligands with turn structure; Chemical reviews; 2010; vol. 110, Issue 4; pp. PR1-PR41; ACS Publications.

Verly et al.; Structure and membrane interactions of the antibiotic peptide dermadistinctin K by multidimensional solution and oriented 15N and 31P solid-state NMR spectroscopy; Biophysical journal; 2009; vol. 96, Issue 6; pp. 2194-2203; The Biophysical Society.

Fisone et al.; N-terminal galanin-(1-16) fragment is an agonist at the hippocampal galanin receptor; Proceedings of the National Academy of Sciences of the United States of America (PNAS); 1989; vol. 86, Issue 23; pp. 9588-9591; United States National Academy of Sciences.

Wennerberg et al.; A 1H NMR study of the solution conformation of the neuropeptide galanin; Biochemical and Biophysical Research Communications; 1990; vol. 166, Issue 3; pp. 1102-1109; Elsevier.

Nilsson et al.; Molecular Dynamics Simulation of Galanin in Aqueous and Nonaqueous Solution; Journal of the American Chemical Society; 1992; vol. 114; pp. 4028-4035; ACS Publications.

Morris et al.; Structural and biochemical studies of human galanin: NMR evidence for nascent helical structures in aqueous solution; Biochemistry; 1995; vol. 34, Issue 14; pp. 4538-4545; ACS Publications.

Barany-Wallje et al.; NMR solution structure and position of transportan in neutral phospholipid bicelles; FEBS letters; 2004; vol. 567, Issue 2-3; pp. 265-269; Wiley.

Carpenter et al.; The glycine residue in cyclic lactam analogues of galanin(1-16)-NH2 is important for stabilizing an N-terminal helix; Biochemistry; 1999; vol. 38, Issue 46; pp. 15295-15304; ACS Publications.

Bock et al.; Getting in Shape: Controlling Peptide Bioactivity and Bioavailability Using Conformational Constraints; ACS Chemical Biology; 2013; vol. 8, Issue 3; pp. 488-499; ACS Publications.

Krulich et al.; Stimulatory and inhibitory effects of purified hypothalamic extracts on growth hormone release from rat pituitary in vitro; Endocrinology; 1968; vol. 83, Issue 4; pp. 783-790; The Endocrine Society.

Veber et al.; Conformationally restricted bicyclic analogs of somatostatin; Proceedings of the National Academy of Sciences of the United States of America (PNAS); 1978; vol. 75, Issue 6; pp. 2636-2640; United States National Academy of Sciences.

Veber et al.; Highly active cyclic and bicyclic somatostatin analogues of reduced ring size; Nature; 1979; vol. 280, Issue 5722; pp. 512-514; Nature Publishing Group.

Veber et al.; A potent cyclic hexapeptide analogue of somatostatin; Nature; 1981; vol. 292, Issue 5818; pp. 55-58; Macmillan Journals Ltd.

Lamberts et al.; Drug therapy—Octreotide; The New England Journal of Medicine; 1996; vol. 334, Issue 4; pp. 246-254; Massachusetts Medical Society.

Roe et al.; PTRAJ and CPPTRAJ: Software for Processing and Analysis of Molecular Dynamics Trajectory Data; 2013; Journal of Chemical Theory and Computation; vol. 9, Issue 7; pp. 3084-3095; ACS Publications.

Lindorff-Larsen et al.; Improved side-chain torsion potentials for the Amber ff99SB protein force field; Proteins-Structure Function and Bioinformatics; 2010; vol. 78, Issue 8; pp. 1950-1958; Wiley.

Vymetal et al.; Parametrization of 2,2,2-Trifluoroethanol Based on the Generalized Amber Force Field Provides Realistic Agreement between Experimental and Calculated Properties of Pure Liquid as Well as Water-Mixed Solutions; The Journal of Physical Chemistry B; 2014; vol. 118, Issue 35; pp. 10390-10404; ACS Publications.

Gotz et al.; Routine Microsecond Molecular Dynamics Simulations with AMBER on GPUs. 1. Generalized Born; Journal of Chemical Theory and Computation; 2012; vol. 8, Issue 5; pp. 1542-1555; ACS Publications.

Salomon-Ferrer et al.; Routine Microsecond Molecular Dynamics Simulations with AMBER on GPUs. 2. Explicit Solvent Particle Mesh Ewald; Journal of Chemical Theory and Computation; 2013; vol. 9, Issue 9; pp. 3878-3888; ACS Publications.

Liu et al.; Evolution of galanin receptor genes: insights from the deuterostome genomes; Journal of Biomolecular Structure and Dynamics; 2010; vol. 28, Issue 1; pp. 97-106; Adenine Press.

Church et al.; Molecular modelling and site-directed mutagenesis of human GALR1 galanin receptor defines determinants of receptor subtype specificity; Protein engineering; 2002; vol. 15, Issue 4; pp. 313-323; Oxford University Press.

Kask et al.; Delineation of the peptide binding site of the human galanin receptor; The EMBO Journal; 1996; vol. 15, Issue 2; pp. 236-244; Wiley.

Kessler; Peptide Conformations.19. Conformation and Biological-Activity of Cyclic-Peptides; Angewandte Chemie International Edition; 1982; vol. 21, Issue 7; pp. 512-523; Wiley.

Reyes-Alcaraz et al.; Development of Spexin-based Human Galanin Receptor Type II-Specific Agonists with Increased Stability in Serum and Anxiolytic Effect in Mice; Scientific Reports; 2016; vol. 6; Article 21453; Nature.

Ohtaki et al.; Isolation and cDNA cloning of a novel galanin-like peptide (GALP) from porcine hypothalamus; The Journal of biological chemistry; 1999; vol. 274, Issue 52; pp. 37041-37045; The American Society for Biochemistry and Molecular Biology, Inc.

Skinner et al.; CcpNmr AnalysisAssign: a flexible platform for integrated NMR analysis; Journal of biomolecular NMR; 2016; vol. 66, Issue 2; pp. 111-124; Springer.

Tam et al.; Disulfide bond formation in peptides by dimethyl sulfoxide. Scope and applications; Journal of the American Chemical Society; 1991; vol. 113, Issue 17; pp. 6657-6662; ACS Publications.

International Search Report and Written Opinion of PCT application No. PCT/CN2018/080353 issued from the International Search Authority dated Jun. 21, 2018.

\* cited by examiner hSPX in β-hairpin (MD, Water)

hSPX in α-helix (MD, 50% TFE)

| | | |
|---|---|---|
| hSPX | N W T P Q A M L Y L K G A Q - NH₂ | SEQ ID NO: 2 |
| C1 | ⒸW T P Q A M L Y L K G A Q - NH₂ | SEQ ID NO: 3 |
| C2 | N Ⓒ T P Q A M L Y L K G A Q - NH₂ | SEQ ID NO: 12 |
| C3 | N W Ⓒ P Q A M L Y L K G A Q - NH₂ | SEQ ID NO: 13 |
| C4 | N W T Ⓒ Q A M L Y L K G A Q - NH₂ | SEQ ID NO: 4 |
| C5 | N W T P Ⓒ A M L Y L K G A Q - NH₂ | SEQ ID NO: 14 |
| C6 | N W T P Q Ⓒ M L Y L K G A Q - NH₂ | SEQ ID NO: 15 |
| C7 | N W T P Q A Ⓒ L Y L K G A Q - NH₂ | SEQ ID NO: 16 |
| C8 | N W T P Q A M Ⓒ Y L K G A Q - NH₂ | SEQ ID NO: 17 |
| C9 | N W T P Q A M L Ⓒ L K G A Q - NH₂ | SEQ ID NO: 18 |
| C10 | N W T P Q A M L Y Ⓒ K G A Q - NH₂ | SEQ ID NO: 19 |
| C11 | N W T P Q A M L Y L Ⓒ G A Q - NH₂ | SEQ ID NO: 20 |
| C12 | N W T P Q A M L Y L K Ⓒ A Q - NH₂ | SEQ ID NO: 21 |
| C13 | N W T P Q A M L Y L K G Ⓒ Q - NH₂ | SEQ ID NO: 5 |
| C14 | N W T P Q A M L Y L K G A Ⓒ - NH₂ | SEQ ID NO: 22 |

Figure 42

IDENTIFICATION OF CYCLIC PEPTIDE AGONISTS OF GALANIN RECEPTOR 2 AND 3 GUIDED BY SPEXIN SOLUTION STRUCTURE

CROSS-REFERENCE TO RELATED APPLICATIONS

This application claims priority from U.S. Provisional Patent Application No. 62/482,751 filed on Apr. 7, 2017 and U.S. Provisional Patent Application No. 62/506,654 filed on May 16, 2017, the disclosures of which are hereby incorporated by reference in its entirety.

FIELD OF THE INVENTION

The present disclosure relates to cyclic peptide agonists of human galanin receptor 2 (GalR2) and galanin receptor 3 (GalR3) and methods of preparation and use in the treatment of spexin-deficient disorders thereof. More particularly, present disclosure provides cyclic peptide agonists of GalR2 and GalR3, which are useful in for the treatment of GalR2-related, GalR3-related, and/or spexin-deficient disorders, such as obesity.

BACKGROUND OF THE INVENTION

Galanin receptors (GalRs) are G-protein-coupled receptors (GPCRs) that mediate signaling of galanin and other neuropeptides in the galanin family. So far, three subtypes of GalRs have been identified, namely GalR1, GalR2 and GalR3. With relatively low sequence similarity between one and other. However, their sequences are highly conserved among different vertebrate species.

Widely expressed in the brain and peripheral tissues, GalRs are involved in the regulation of a number of biological functions, including nociception, cognition, mood control, neuroendocrine function, reproduction, feeding control, energy and osmotic homeostasis, and metabolism. They have also been implicated in many human diseases, including neurological and metabolic disorders, inflammation, and cancers. However, understanding the roles of GalRs in health and disease, and clinical translation have been hindered by the lack of metabolically stable and receptor-specific probes.

Spexin (SPX) is a newly identified, GalR-cognate neuropeptide. Expressed centrally and peripherally, SPX can regulate gastrointestinal motility, adrenocortical cell proliferation, cardiovascular and renal function, nociception, reproduction, and feeding. It has also been implicated in a number of human disorders, including obesity, type-II diabetes, nonalcoholic fatty liver disease, and constipation.

Containing 14 amino acids and amidated at C-terminal, SPX is similar to the N-terminal sequence of galanin. Nevertheless, receptor recognition profiles of these two neuropeptides are different: galanin activates GalR1, GalR2 and GalR3. Whereas, SPX only activates GalR2 and GalR3. For GalR2, SPX and galanin have comparable activity; while for GalR3, SPX has much better activity than galanin.

Elucidating the biological role of GalRs in health and disease, and clinical translation of this knowledge to new methods of medical treatment has been hindered by the lack of metabolically stable and receptor-specific probes. Thus, there is a need to develop new agonists receptor selective probes of GalR2 and GalR3 with improved metabolic properties.

SUMMARY OF THE INVENTION

Accordingly, it is an object of the present disclosure to provide peptide agonists of GalR2 and GalR3 and methods of use thereof in the treatment of GalR2- and GalR3-related and spexin-deficient disorders, such as obesity.

In a first aspect of the present disclosure, there is provided herein is a peptide comprising a sequence having at least 92.8% homology with SEQ ID NO: 23 or SEQ ID NO: 24; or having at least 93.7% homology with SEQ ID NO: 25 or a therapeutically effective salt thereof, wherein R is hydrogen, alkyl, or acyl with the proviso that SEQ ID NO: 23 must contain cysteine at position one and position thirteen of SEQ ID NO: 23; SEQ ID NO: 24 must contain cysteine at position four and position thirteen of SEQ ID NO: 25; SEQ ID NO: 25 must contain cysteines at position one and position thirteen of SEQ ID NO: 25.

In a first embodiment of the first aspect, provided herein is the peptide of the first aspect, wherein R is hydrogen, $(C_1-C_6)$alkyl, or $(C_1-C_6)$acyl.

In a second embodiment of the first aspect, provided herein is the peptide of the first aspect, wherein R is hydrogen or $(C_1-C_3)$acyl.

In a third embodiment of the first aspect, provided herein is the peptide of the first aspect, wherein R is hydrogen or acetyl.

In a fourth embodiment of the first aspect, provided herein is the peptide of the first aspect, wherein the peptide comprises SEQ ID NO: 23; SEQ ID NO: 24; or SEQ ID NO: 25.

In a fifth embodiment of the first aspect, provided herein is the peptide of the fourth embodiment of the first aspect, wherein R is hydrogen, $(C_1-C_6)$alkyl, or $(C_1-C_6)$acyl.

In a sixth embodiment of the first aspect, provided herein is the peptide of the fourth embodiment of the first aspect, wherein R is hydrogen or $(C_1-C_3)$acyl, In a seventh embodiment of the first aspect, provided herein is the peptide of the fourth embodiment of the first aspect, wherein R is hydrogen or acetyl.

In a second aspect of the present disclosure, provided herein is a peptide consisting of SEQ ID NO: 23; SEQ ID NO: 24; or SEQ ID NO: 25 or a therapeutically effective salt thereof, wherein R is hydrogen, alkyl, or acyl.

In a first embodiment of the second aspect, provided herein is the peptide of the second aspect, wherein R is hydrogen, $(C_1-C_6)$alkyl, or $(C_1-C_6)$acyl.

In a second embodiment of the second aspect, provided herein is the peptide of the second aspect, wherein the peptide is SEQ ID NO: 6; SEQ ID NO: 7; SEQ ID NO: 8; SEQ ID NO: 10; or SEQ ID NO: 11.

In a third aspect of the present disclosure, provided herein is a pharmaceutical composition comprising a peptide of the first aspect and at least one pharmaceutically acceptable excipient.

In a fourth aspect of the present disclosure, provided herein is a method of treating a spexin-deficient disorder in a patient in need thereof comprising the step of administering a therapeutically effective amount of a peptide of the first aspect to the patient.

In a first embodiment of the fourth aspect, provided herein is the method of the fourth aspect, wherein the spexin-deficient disorder is obesity, type-II diabetes, nonalcoholic fatty liver disease or constipation.

In a second embodiment of the fourth aspect, provided herein is the method of the fourth aspect, wherein the peptide comprises SEQ ID NO: 23; SEQ ID NO: 24; or SEQ ID NO: 25; or a therapeutically acceptable salt thereof.

In a third embodiment of the fourth aspect, provided herein is the method of the fourth aspect, wherein the peptide is SEQ ID NO: 6; SEQ ID NO: 7; SEQ ID NO: 8; SEQ ID NO: 10; or SEQ ID NO: 11; or a therapeutically acceptable salt thereof.

In a fourth embodiment of the fourth aspect, provided herein is the method of the fourth aspect, wherein the spexin-deficient disorder is obesity.

In a fifth embodiment of the fourth aspect, provided herein is the method of the first embodiment of the fourth aspect, wherein the peptide comprises SEQ ID NO: 23; SEQ ID NO: 24; or SEQ ID NO: 25; or a therapeutically acceptable salt thereof.

In a sixth embodiment of the fourth aspect, provided herein is the method of the first embodiment of the fourth aspect, wherein the peptide is SEQ ID NO: 6; SEQ ID NO: 7; SEQ ID NO: 8; SEQ ID NO: 10; or SEQ ID NO: 11; or a therapeutically acceptable salt thereof.

In a seventh embodiment of the fourth aspect, provided herein is the method of the fourth aspect, wherein the peptide is administered to the patient intraperitoneally.

Those skilled in the art will appreciate that the invention described herein is susceptible to variations and modifications other than those specifically described. The invention includes all such variation and modifications. The invention also includes all of the steps and features referred to or indicated in the specification, individually or collectively, and any and all combinations or any two or more of the steps or features.

The term "amino acid" refers to naturally occurring and non-natural amino acids. Naturally occurring amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine.

An "amino terminus modification group" refers to any molecule that can be attached to the amino terminus of a polypeptide. Similarly, a "carboxy terminus modification group" refers to any molecule that can be attached to the carboxy terminus of a polypeptide. Terminus modification groups include, but are not limited to, various water soluble polymers (such as polyethylene glycol (PEG)), peptides or proteins such as serum albumin, albumin binding domain or other moieties that increase serum half-life of peptides.

As used herein, the term "variant" refers to a polynucleotide or nucleic acid differing from a reference nucleic acid or polypeptide, but retaining essential properties thereof. Generally, variants are overall closely similar, and, in many regions, identical to the reference nucleic acid or polypeptide.

A variant can, for example, comprise the amino acid sequence of the parent polypeptide sequence with at least one conservative amino acid substitution. Alternatively or additionally, the variant can comprise the amino acid sequence of the parent polypeptide sequence with at least one non-conservative amino acid substitution. In this case, it is preferable for the non-conservative amino acid substitution to not interfere with or inhibit the biological activity of the functional variant. The non-conservative amino acid substitution may enhance the biological activity of the variant, such that the biological activity of the variant is increased as compared to the parent polypeptide.

Amino acid substitutions of the described polypeptides can be conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), an amino acid with a side chain of a certain size with another amino acid with a side chain of similar size, etc.

The terms "percentage homology" and "percentage sequence identity", when used in reference to a polypeptide or polynucleotide sequence, are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Homology is evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988, Proc. Natl. Acad. Sci. USA 85(8):2444-2448; Altschul et al., 1990, J. Mol. Biol. 215(3):403-410; Thompson et al., 1994, Nucleic Acids Res. 22(2):4673-4680; Higgins et al. 1996, Methods Enzymol. 266:383-402; Altschul et al., 1990, J. Mol. Biol. 215(3):403-410; Altschul et al., 1993, Nature Genetics 3:266-272). In certain embodiments, protein and nucleic acid sequence homologies are evaluated using the Basic Local Alignment Search Tool ("BLAST") which is well known in the art (see, e.g., Karlin and Altschul, 1990, Proc. Natl. Acad. Sci. USA 87:2267-2268; Altschul et al., 1990, J. Mol. Biol. 215:403-410; Altschul et al., 1993, Nature Genetics 3:266-272; Altschul et al., 1997, Nuc. Acids Res. 25:3389-3402).

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term "alkyl" refers to unsubstituted alkyl groups that do not contain heteroatoms. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer, about 10 or fewer, about 9 or fewer, about 8 or fewer, about 7 or fewer, about 6 or fewer, about 5 or fewer, about 4 or fewer, about 3 or fewer, or about 2 or fewer carbon atoms. Thus, the term includes straight chain alkyl groups such as methyl, ethyl, propyl, butyl, pentyl, hexyl, heptyl, octyl, nonyl, decyl, undecyl, dodecyl and the like. The term also includes branched chain isomers of straight chain alkyl groups, including but not limited to, the following which are provided by way of example: —CH($CH_3$)$_2$, —CH($CH_3$)($CH_2CH_3$), —CH($CH_2CH_3$)$_2$, —C($CH_3$)$_3$, —C($CH_2CH_3$)$_3$, —$CH_2$CH($CH_3$)$_2$, —$CH_2$CH($CH_3$)($CH_2CH_3$), —$CH_2$CH($CH_2CH_3$)$_2$, —$CH_2$C($CH_3$)$_3$, —$CH_2$C($CH_2CH_3$)$_3$, —CH($CH_3$)CH($CH_3$)($CH_2CH_3$), —$CH_2CH_2$CH($CH_3$)$_2$, —$CH_2CH_2$CH($CH_3$)($CH_2CH_3$), —$CH_2CH_2$CH($CH_2CH_3$)$_2$, —$CH_2CH_2$C($CH_3$)$_3$, —$CH_2CH_2$C($CH_2CH_3$)$_3$, —CH($CH_3$)$CH_2$CH($CH_3$)$_2$, —CH($CH_3$)CH($CH_3$)CH($CH_3$)$_2$, —CH($CH_2CH_3$)CH($CH_3$)CH($CH_3$)($CH_2CH_3$), and others. Likewise, cycloalkyls have from about 3 to about 10, about 3 to about 6, or about 3 to about 5 carbon atoms in their ring structure, and alternatively about 3, 4, 5, 6, or 7 carbons in the ring structure. Thus, the term also includes cyclic alkyl groups, such as cyclopropyl, cyclobutyl, cyclopentyl, cyclohexyl, cycloheptyl and such rings substituted with straight and branched chain alkyl groups as defined above.

The term "acyl" is art-recognized and refers to a group represented by the general formula:

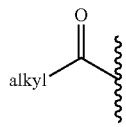

wherein alkyl is as defined above. As used herein, "Ac" represents acetyl (i.e., $CH_3(C=O)$—).

As used herein, the term "therapeutically effective amount" refers to a quantity sufficient to achieve a desired therapeutic and/or prophylactic effect, e.g., an amount which results in the prevention of, or a decrease in a disease or disorder or one or more signs or symptoms associated with a disease or disorder. In the context of therapeutic or prophylactic applications, the amount of a composition administered to the subject will depend on the degree, type, and severity of the disease and on the characteristics of the individual, such as general health, age, sex, body weight and tolerance to drugs. A therapeutically effective amount can be given in one or more administrations. The skilled artisan will be able to determine appropriate dosages depending on these and other factors. The compositions can also be administered in combination with one or more additional therapeutic compounds. In the methods described herein, the therapeutic compounds may be administered to a subject having one or more signs or symptoms of a disease or disorder.

As used herein, an "isolated" or "purified" polypeptide or peptide is substantially free of cellular material or other contaminating polypeptides from the cell or tissue source from which the agent is derived, or substantially free from chemical precursors or other chemicals when chemically synthesized. For example, an isolated peptide would be free of materials that would interfere with diagnostic or therapeutic uses of the agent. Such interfering materials may include enzymes, hormones and other proteinaceous and nonproteinaceous solutes.

As used herein, the terms "treat", "treating", "treatment", and the like refer to reducing or ameliorating a disorder and/or symptoms associated therewith. It will be appreciated, although not precluded, treating a disorder or condition does not require that the disorder, condition, or symptoms associated therewith be completely eliminated. In certain embodiments, treatment includes prevention of a disorder or condition, and/or symptoms associated therewith. The term "prevention" or "prevent" as used herein refers to any action that inhibits or at least delays the development of a disorder, condition, or symptoms associated therewith. Prevention can include primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

As used herein the term "patient" refers to a human or non-human subject (rodent, non-human primate, canine, bovine, ovine, equine, feline, etc) to be treated.

Cysteine residues having side chains forming disulfide linkages present in the polypeptides described herein can be represented by C̲.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF DRAWINGS

The above and other objects and features of the present invention will become apparent from the following description of the invention, when taken in conjunction with the accompanying drawings, in which.

Figure 1A:
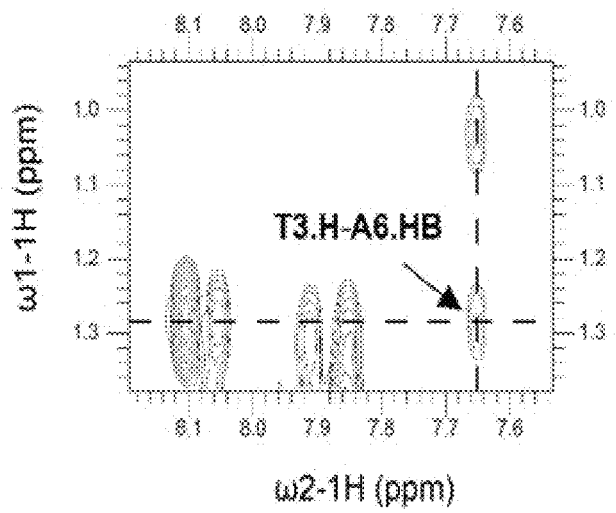
FIG. 1A shows the combined MD simulations and NMR analysis suggested an unexpected hSPX solution structure, the βαβ conformation. The distance constraint between $T^3$.H and $A^6$.HB as suggested by 2D-NOESY experiments of hSPX in water ($H_2O:D_2O$ (90:10), 298 K, mixing time: 500 msec).
Figure 1B:
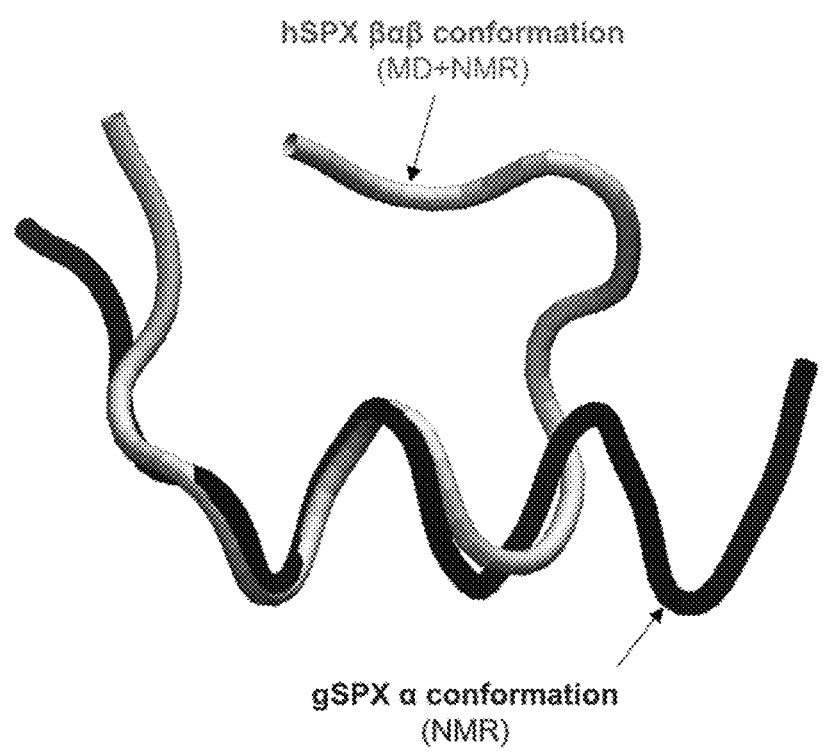
FIG. 1B shows the combined MD simulations and NMR analysis suggested an unexpected hSPX solution structure, the βαβ conformation. The comparison between gSPX α conformation solved by NMR and hSPX βαβ conformation determined by MD and NMR.
Figure 1C:
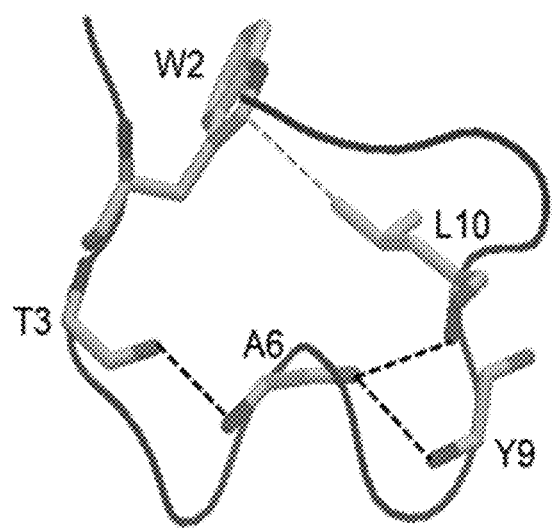

FIG. 1C shows the combined MD simulations and NMR analysis suggested an unexpected hSPX solution structure, the βαβ conformation. The important intra-molecular interactions that stabilize the hSPX βαβ conformation. The hydrogen bonds a depicted in dark dashed line, while the hydrophobic packing were represented by a light dashed line.

Figure 1D:
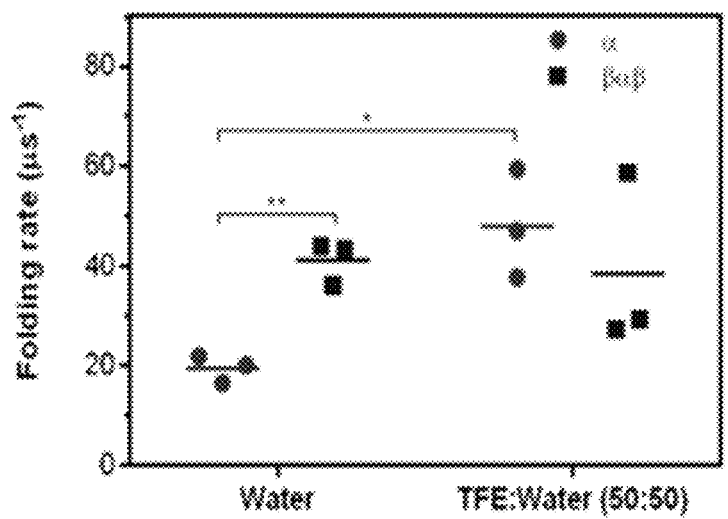

FIG. 1D shows the combined MD simulations and NMR analysis suggested an unexpected hSPX solution structure, the βαβ conformation. The folding rate of hSPX two distinct conformations in three independent, 10 μs MD simulations within different solvents. The conformational- and solvent effects were analyzed by two-way ANOVA (*, $p<0.05$; **, $p<0.01$).

Figure 1E:
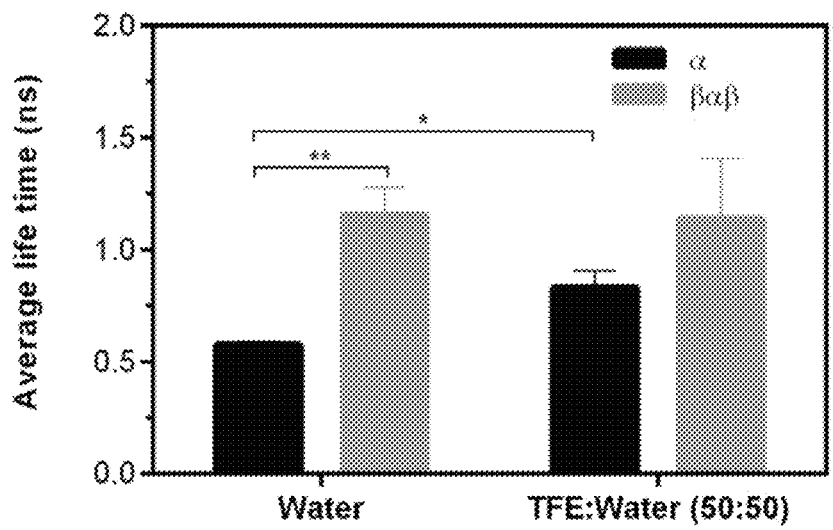

FIG. 1E shows the combined MD simulations and NMR analysis suggested an unexpected hSPX solution structure, the βαβ conformation. The average life time of hSPX two distinct conformations in three independent, 10 μs MD simulations within different solvents. The conformational- and solvent effects were analyzed by two-way ANOVA (*, $p<0.05$; **, $p<0.01$).

Figure 1F:
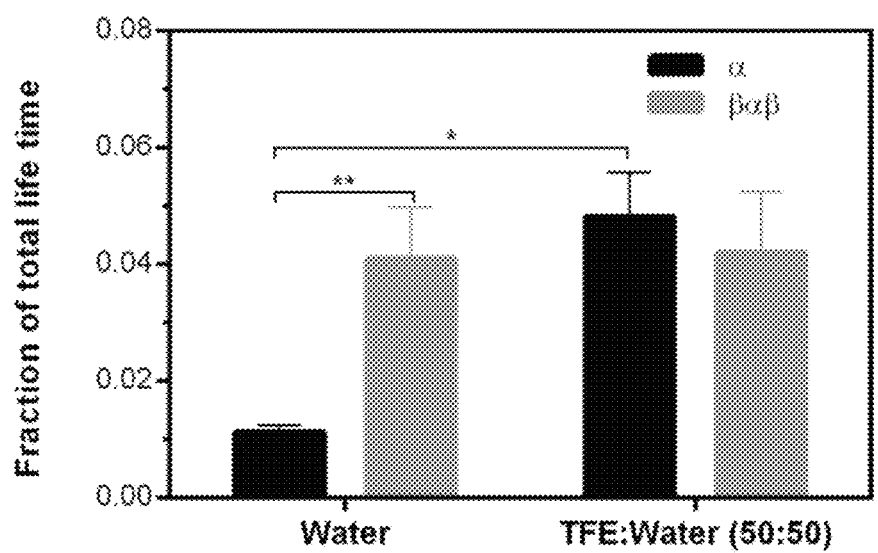

FIG. 1F shows the combined MD simulations and NMR analysis suggested an unexpected hSPX solution structure, the βαβ conformation. The fraction of total life time of hSPX two distinct conformations in three independent, 10-μs MD simulations within different solvents. The conformational- and solvent effects were analyzed by two-way ANOVA (*, $p<0.05$; **, $p<0.01$).

Figure 2A:
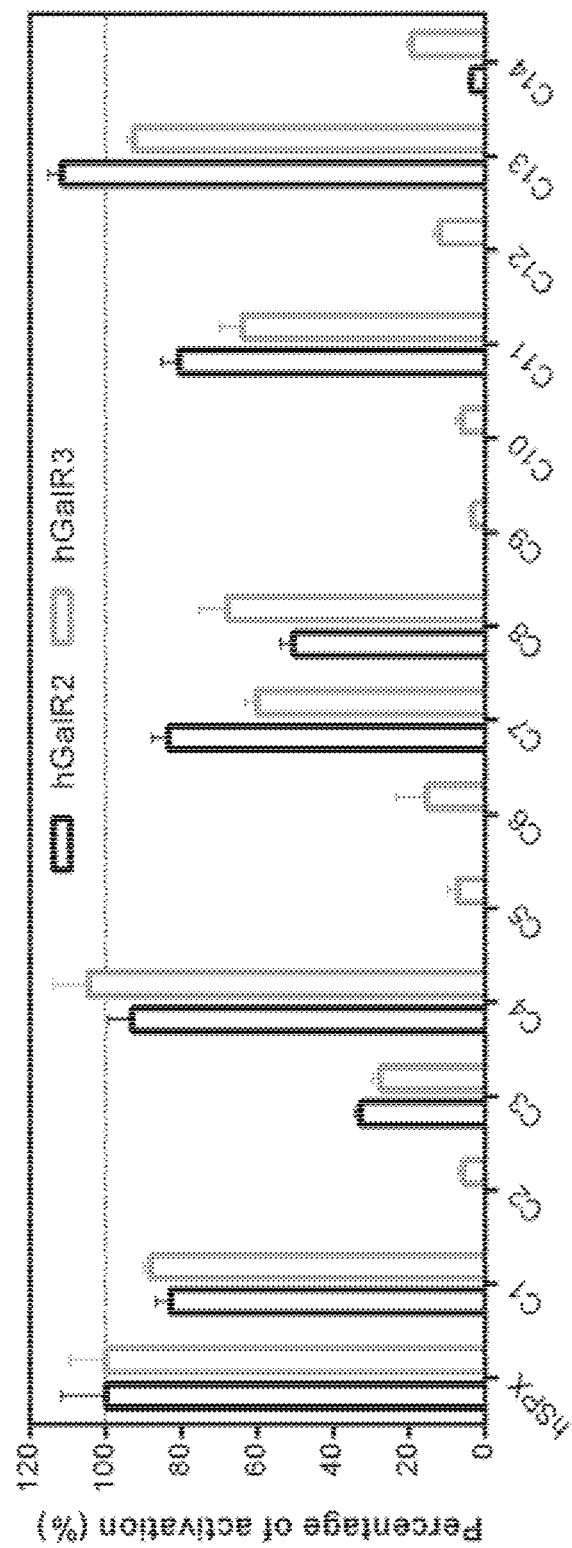

FIG. 2A shows Cysteine-scanning of hSPX identified three candidate sites for disulfide bonding. The relative hGalR2/hGalR3 activation potency of 14 hSPX mutant with single cysteine mutation in SRE-Luc assay. The fold induction of each mutant was compared with the wild type counterpart at single-dose (1-μM) treatment.

Figure 2B:
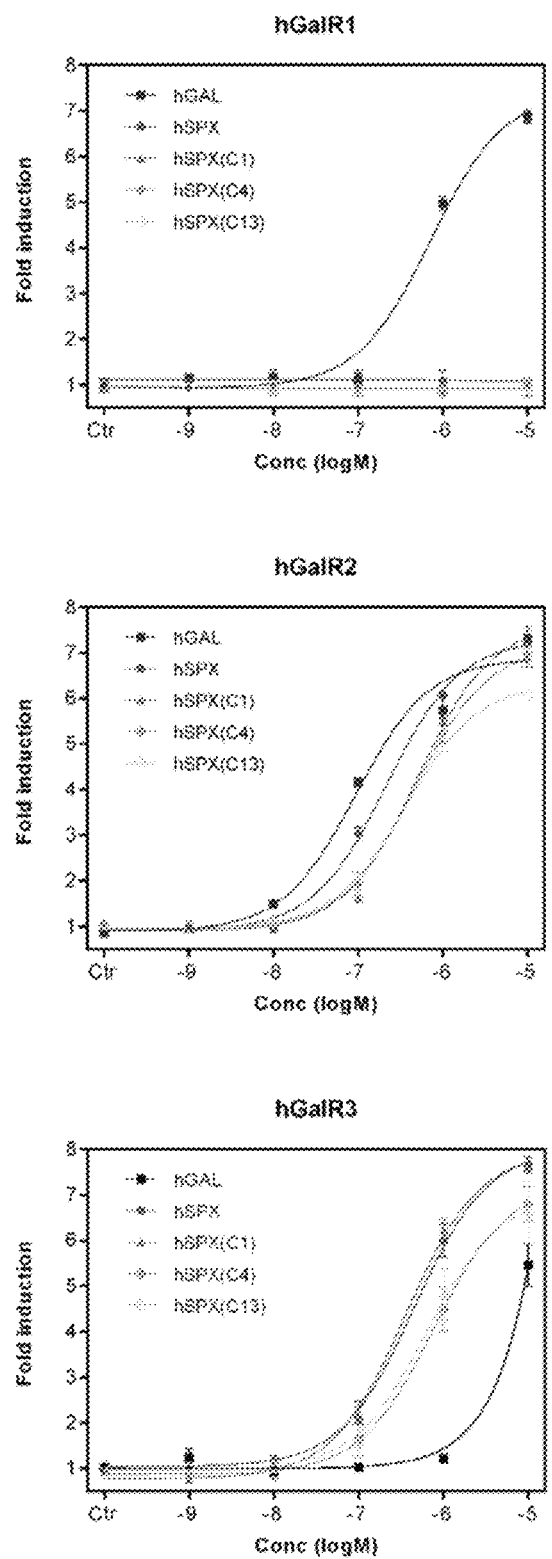

FIG. 2B shows dose response curves for three candidates identified by cysteine-scanning of hSPX for disulfide bonding. The full-dose experiments confirmed that C1, C4, and C13 were candidate sites for disulfide bonding. The dose-response curves were chosen from multiple experiments with three replicates (n=3).

Figure 3A:
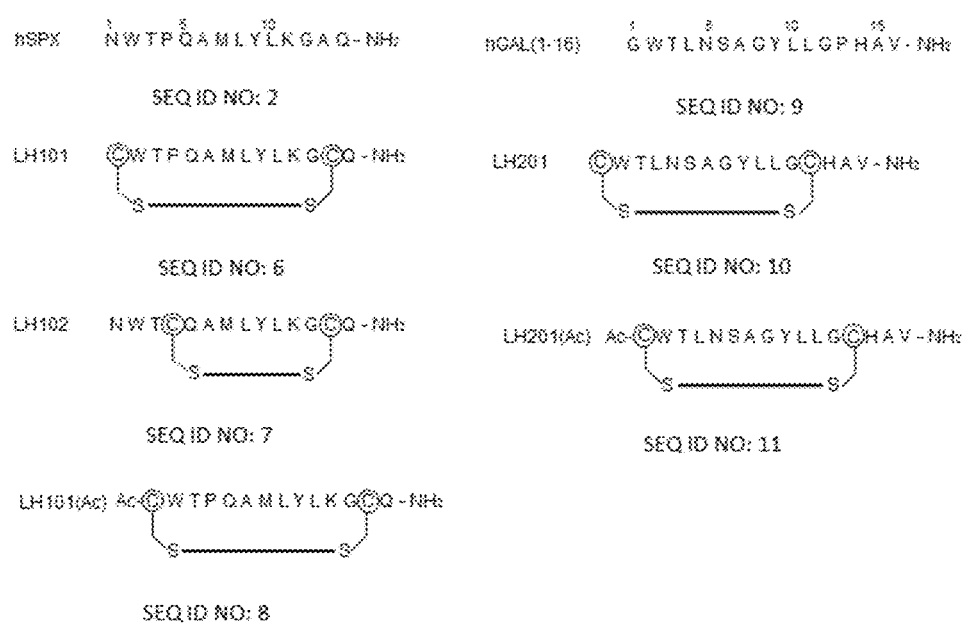

FIG. 3A shows the sequence of cyclic analogs of hSPX and hGAL (1-16) stapled by disulfide bonding.

Figure 3B:
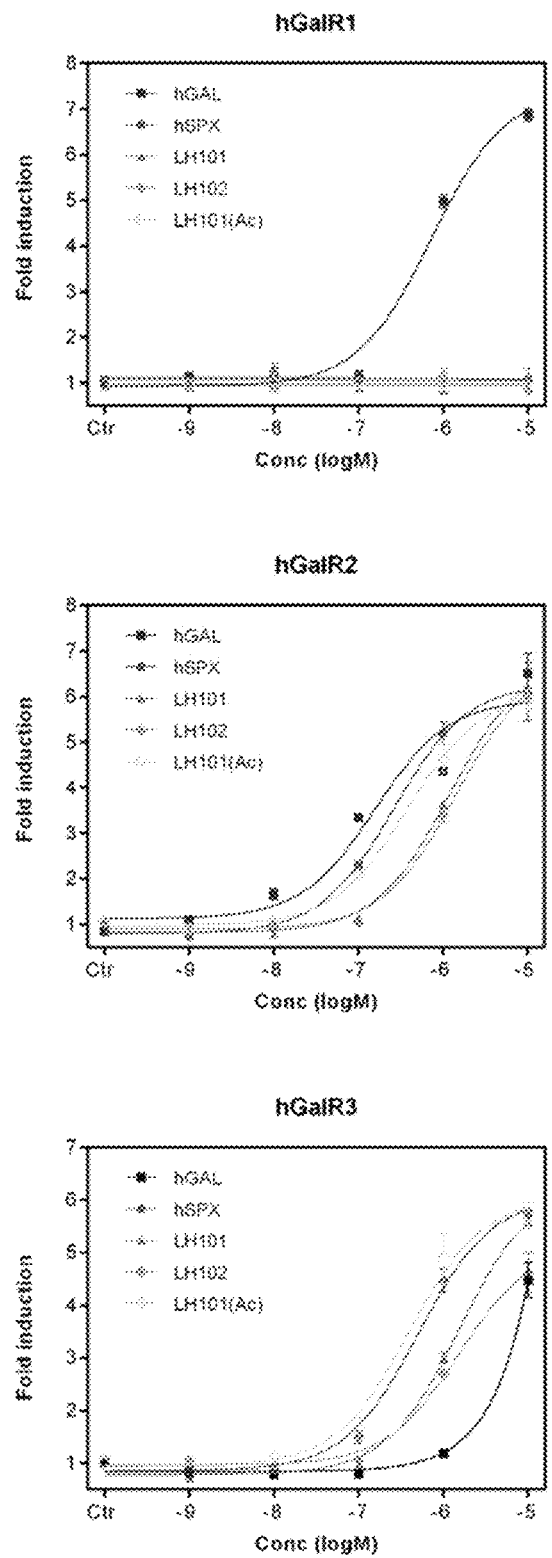

FIG. 3B shows the testing of cyclic analogs of hSPX and hGAL (1-16). The fold induction of cyclic hSPX analogs (LH101, LH102, and LH101 (Ac)) in full-dose SRE-Luc experiments. The wild type hGAL and hSPX were employed as controls. The dose-response curves were chosen from multiple experiments with three replicates (n=3).

Figure 3C:
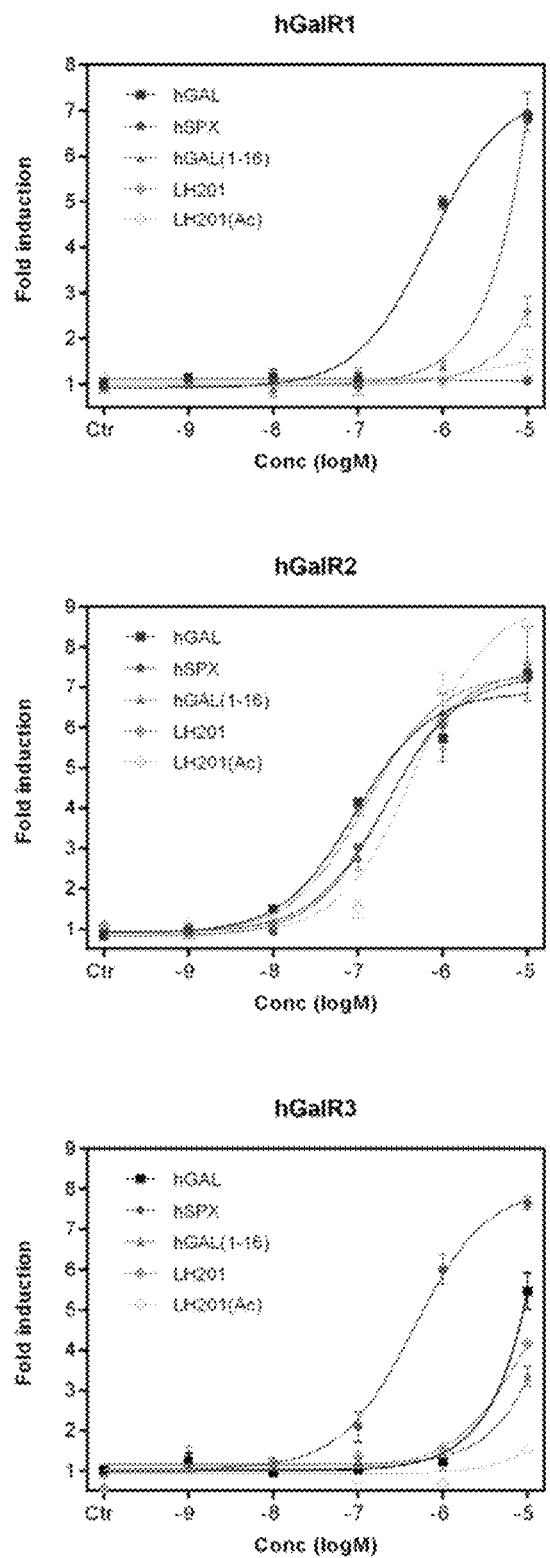

FIG. 3C shows the testing of cyclic analogs of hSPX and hGAL (1-16). The fold induction of cyclic hGAL (1-16) analogs (LH201, LH201 (Ac)) in full-dose SRE-Luc experiments. The wild type hGAL, hSPX, and hGAL (1-16) were employed as controls. The dose-response curves were chosen from multiple experiments with three replicates (n=3).

Figure 4A:
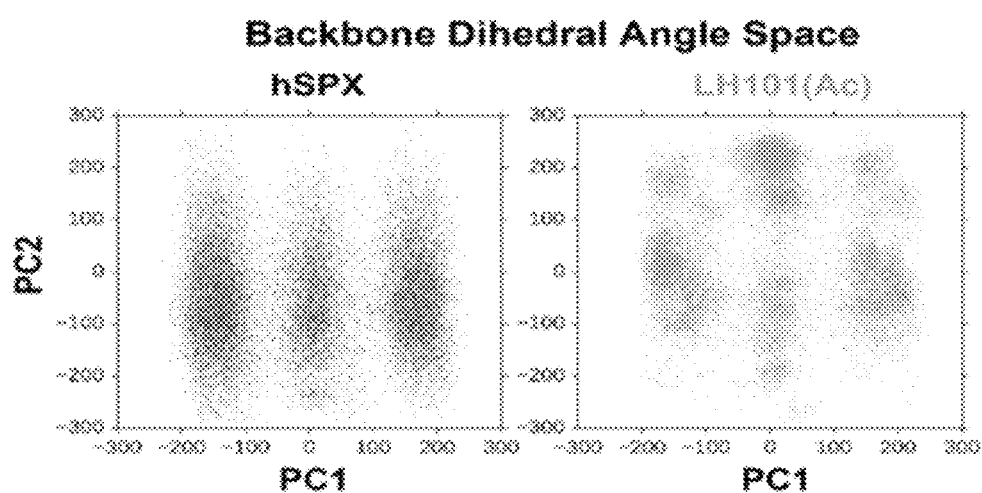

FIG. 4A shows the solution structure of cyclic hSPX analog in water, LH101 (Ac), as suggested by MD simulation and NMR analysis. The backbone dihedral space of hSPX and LH101 (Ac) in MD simulation in water.

Figure 4B:
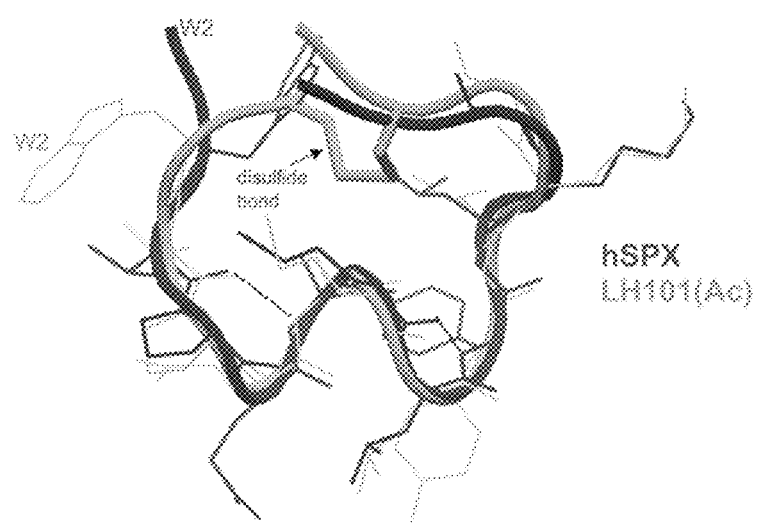

FIG. 4B shows the solution structure of cyclic hSPX analog in water, LH101 (Ac), as suggested by MD simulation and NMR analysis. The dominant solution structure of LH101 (Ac) in water determined by MD simulation and NMR. The disulfide bond was shown as stick (the arrow). It was compared with hSPX βαβ conformation. The hydrogen bonds were depicted in black, dashed line.

Figure 4C:
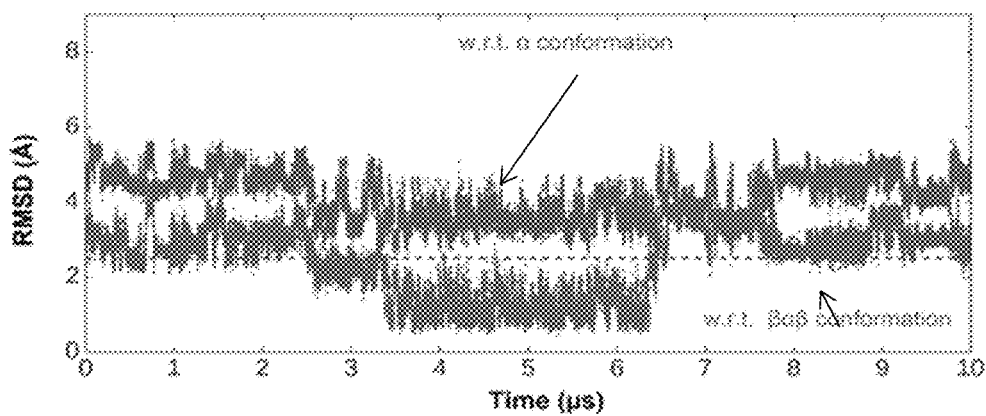

FIG. 4C shows the solution structure of cyclic hSPX analog in water, LH101 (Ac), as suggested by MD simulation and NMR analysis. The folding trajectory of LH101 (Ac) in water in 10-μs MD simulation. The gSPX α conformation and hSPX βαβ conformation were used as reference structure.

Figure 4D:
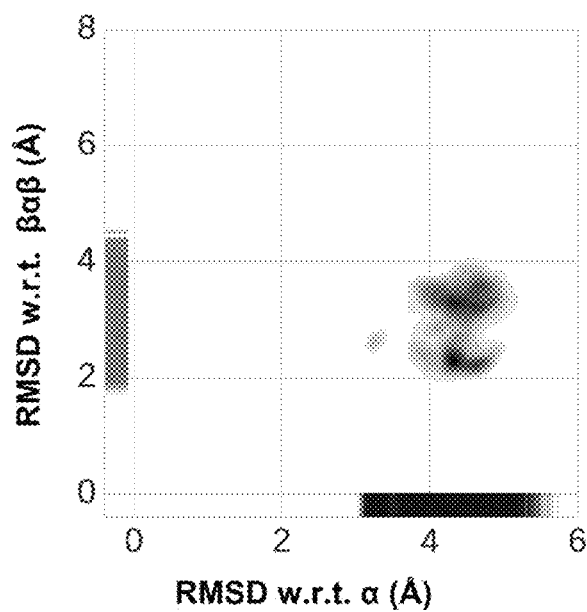

FIG. 4D shows the solution structure of cyclic hSPX analog in water, LH101 (Ac), as suggested by MD simulation and NMR analysis. The conformational space of LH101 (Ac) in water in 10-μs MD simulation.

Figure 4E:
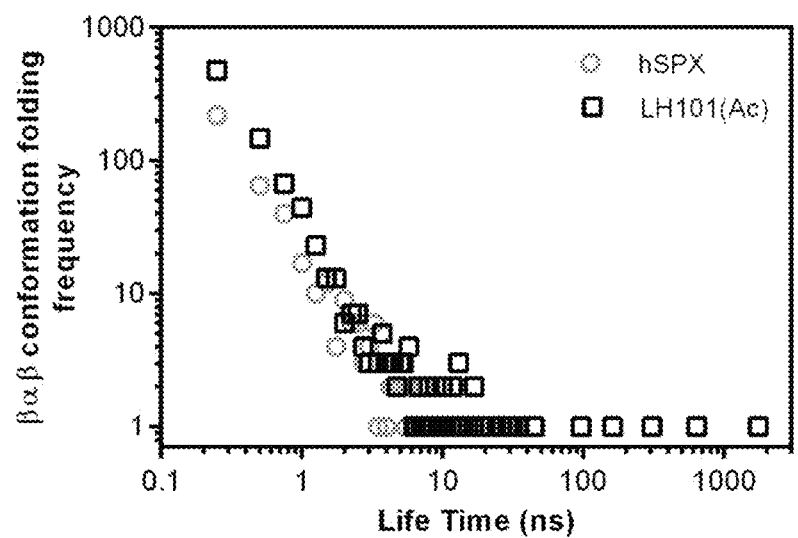

FIG. 4E shows the solution structure of cyclic hSPX analog in water, LH101 (Ac), as suggested by MD simulation and NMR analysis. The βαβ conformation folding kinetics of LH101 (Ac) in water in 10-μs MD simulation. These values were compared with hSPX.

Figure 5A:
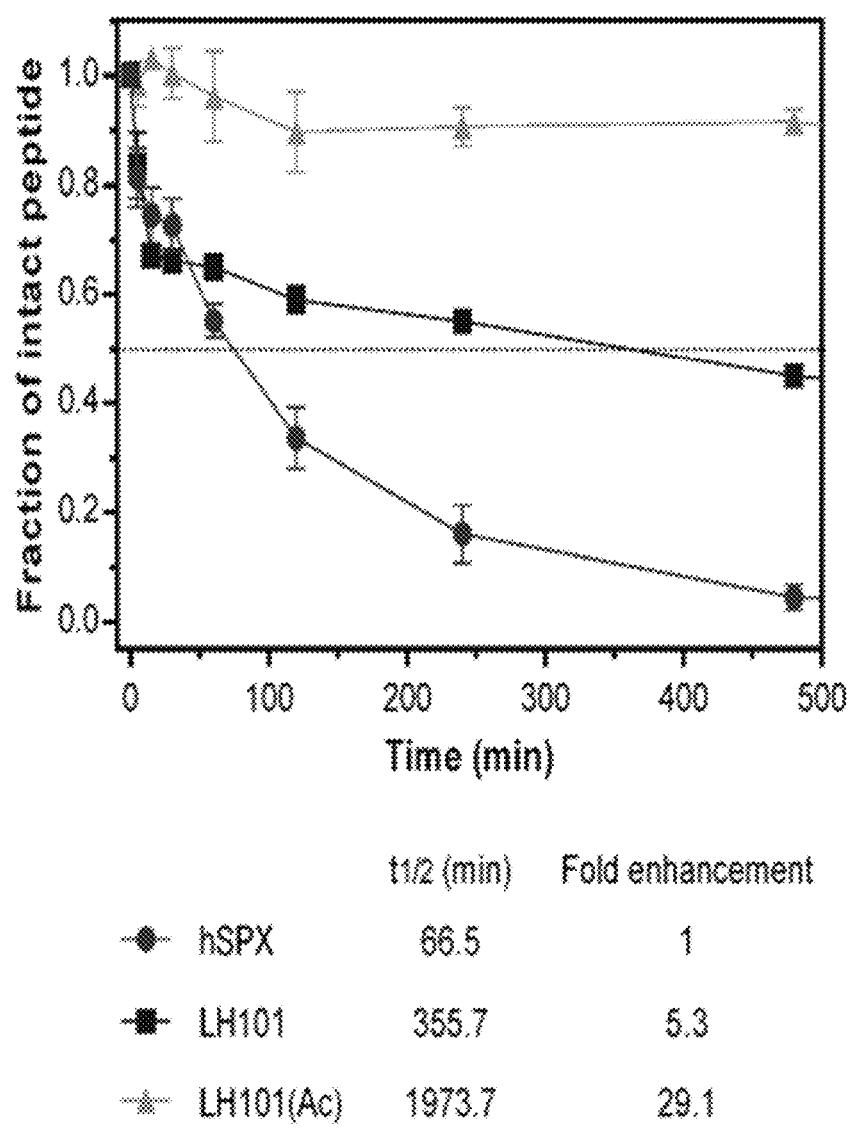

FIG. 5A shows In vitro serum stability testing of cyclic hSPX/hGAL (1-16) analogs. The fraction of intact peptide of hSPX and its cyclic analogs (LH101 and LH101 (Ac)) at multiple time points. The calculated half-life ($t_{1/2}$) and fold enhancement with regard to the wild type counterpart were shown at the bottom.

Figure 5B:
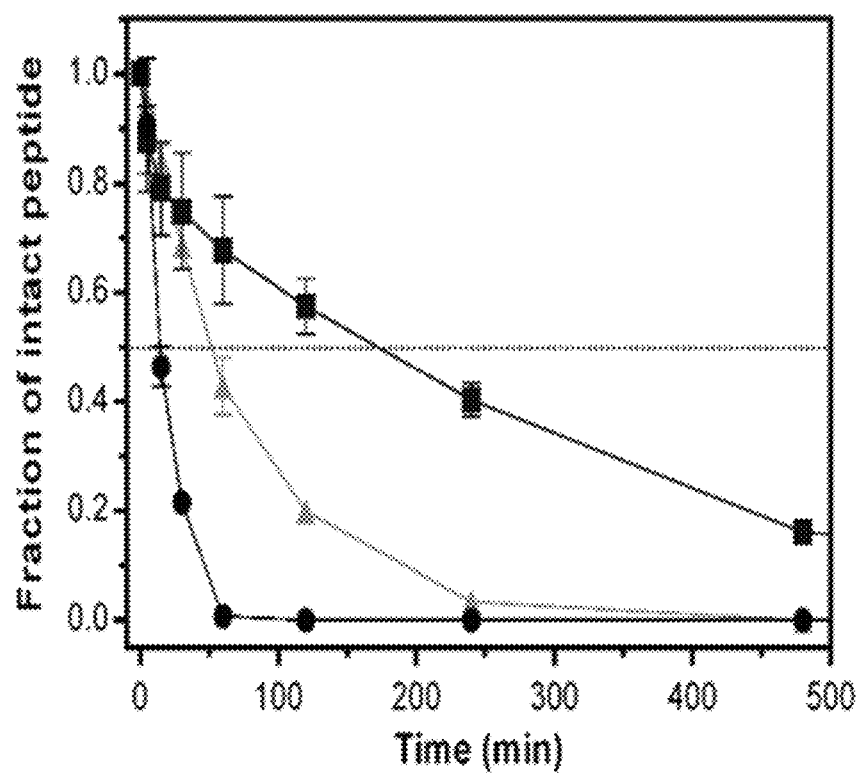

FIG. 5B shows In vitro serum stability testing of cyclic hSPX/hGAL (1-16) analogs. The fraction of intact peptide of hGAL (1-16) and its cyclic analogs (LH201 and LH201 (Ac)) at multiple time points. The calculated half-life ($t_{1/2}$) and fold enhancement with regard to the wild type counterpart were shown at the bottom.

Figure 6A:
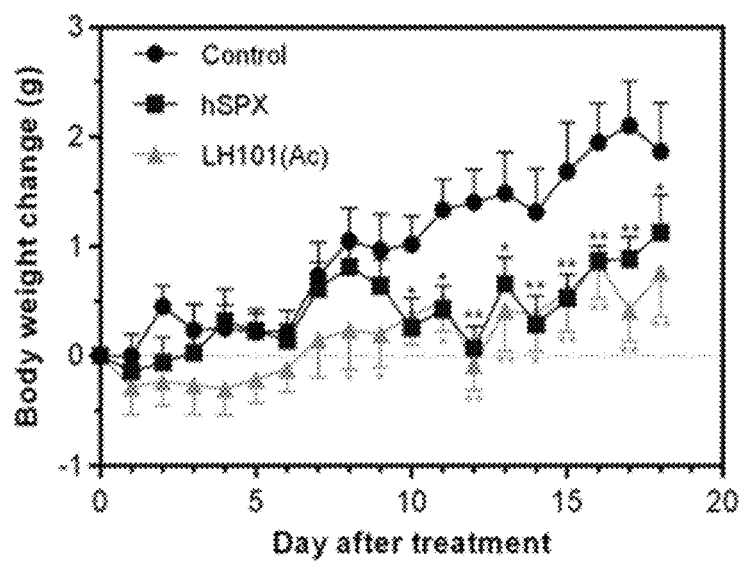

FIG. 6A shows In vivo anti-obesity efficacy testing of cyclic hSPX analog (LH101 (Ac)). The effect of hSPX and LH101 (Ac) treatment on body weight gain in high-fat-diet induced obesity mice (for each group, n=7). The time and treatment effect were analyzed by two-way ANOVA (*, $p<0.05$; **, $p<0.01$).

Figure 6B:
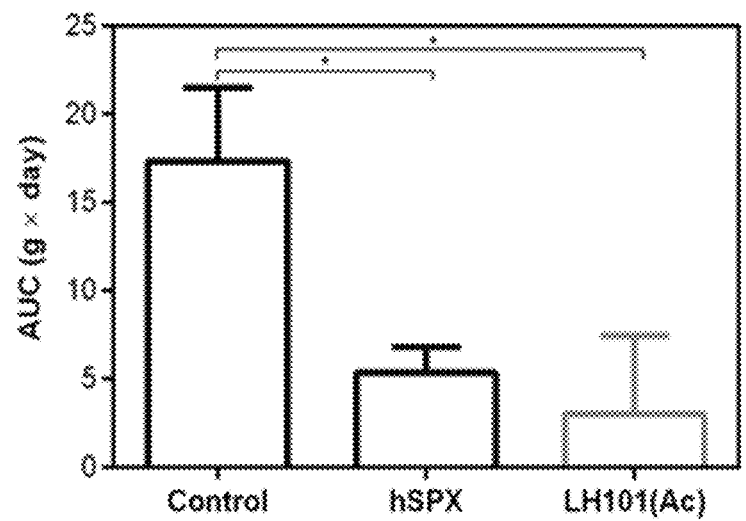

FIG. 6B shows In vivo anti-obesity efficacy testing of cyclic hSPX analog (LH101 (Ac)). The area under curve (AUC) of body weight gain curve as shown in (FIG. 6A). The treatment effect was evaluated by t-test.

Figure 6C:
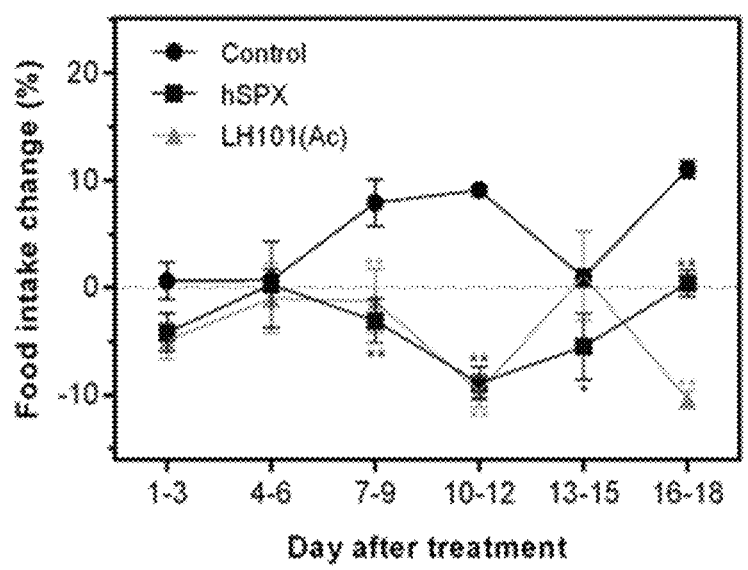

FIG. 6C shows In vivo anti-obesity efficacy testing of cyclic hSPX analog (LH101 (Ac)). The effect on food intake by different treatments. Food intakes were recorded by every three days. The time and treatment effects were analyzed by two-way ANOVA (*, $p<0.05$; **, $p<0.01$).

Figure 7:
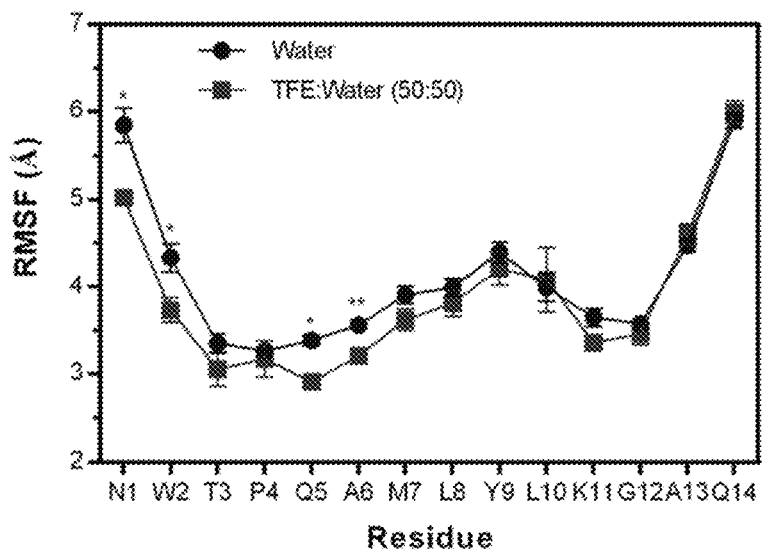

FIG. 7 shows the Cα root-mean-square fluctuation (RMSF) of each residue in hSPX during MD simulations, in water or in TFE:water (50:50) mixture. The results were generated by three independent 10 μs simulations, and represented by mean±S.E.M. For each residue, the solvent effect on RMSF was analyzed by t-test (*, $p<0.05$; **, $p<0.01$).

Figure 8:
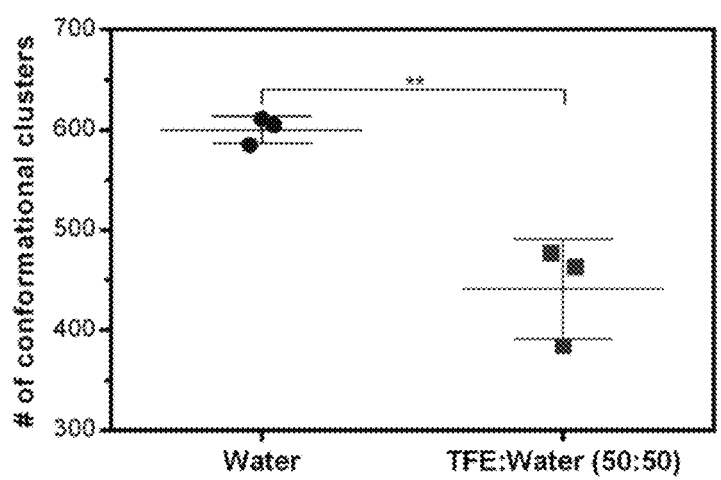

FIG. 8 shows the number of conformational clusters of hSPX during MD simulations, in water or in TFE:water (50:50) mixture. Conformational clustering calculation was based on the main-chain atom root-mean-square distance (RMSD) of hSPX (2-13). The solvent effect was analyzed by t-test (*, $p<0.05$; **, $p<0.01$).

Figure 9:
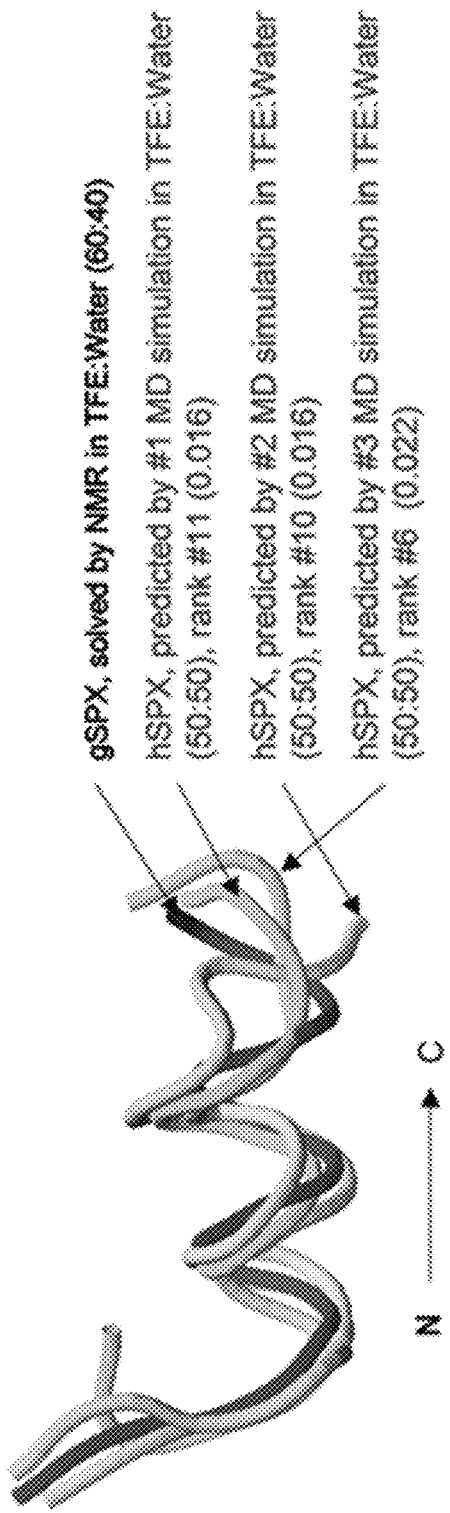

FIG. 9 shows the gSPX α conformation was recaptured by three independent hSPX 10 μs MD simulations in TFE:water (50:50) solutions. For the predicted conformation by MD, the ranking number of the corresponding cluster were labeled. Number in the bracket was the time faction of that conformational cluster.

Figure 10:
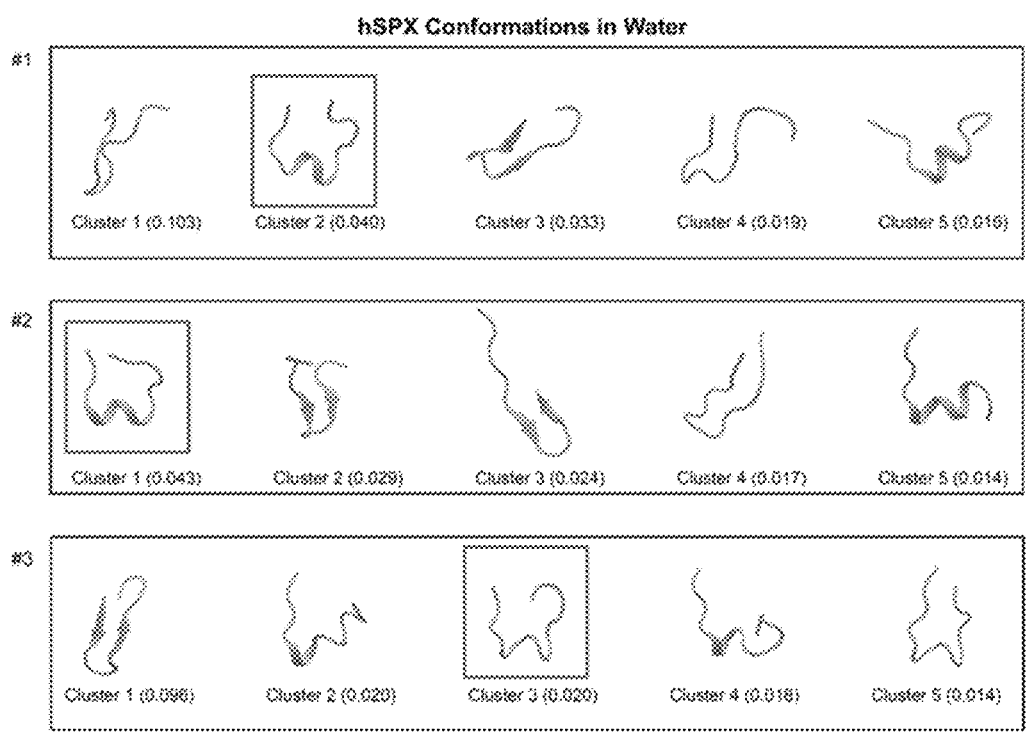

FIG. 10 shows the representative structures of top 5 conformational clusters of hSPX in water during three independent, 10 μs, MD simulations. Conformational clustering calculation was based on the main-chain atom RMSD of hSPX (2-13). For each cluster, the representative structure was demonstrated. Number in the bracket was the time faction of that conformational cluster. The conformation which satisfied the $T^3$.H-$A^6$.HB distance constraint was highlighted by rectangles.

Figure 11:
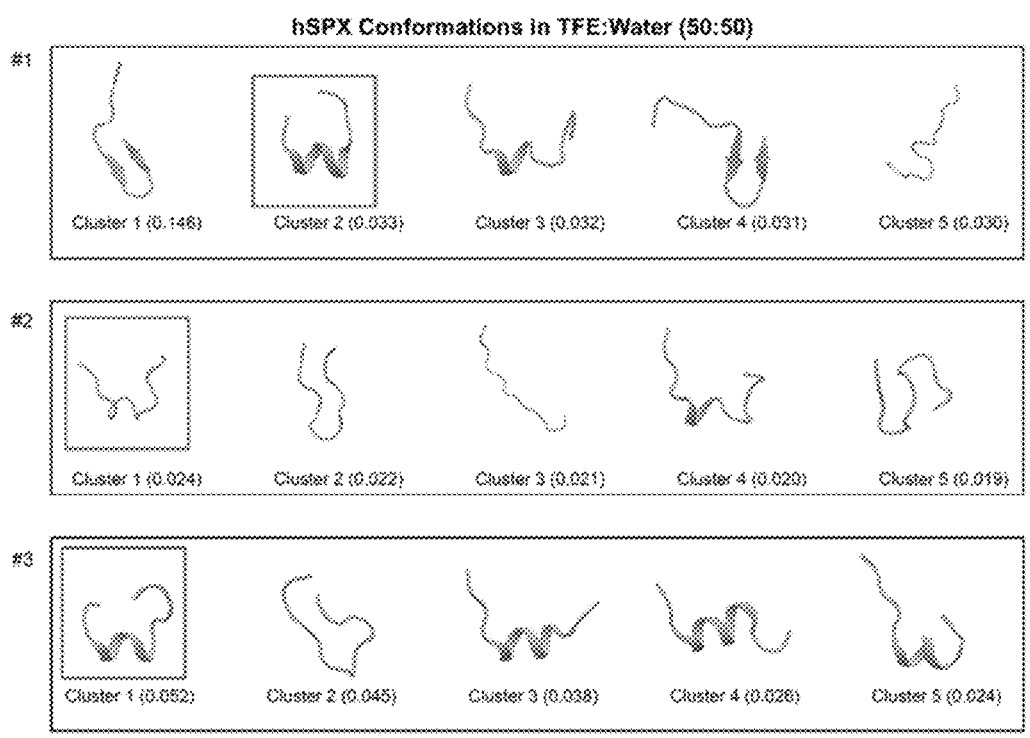

FIG. 11 shows the representative structures of top 5 conformational clusters of hSPX in TFE:water mixture (50:50) during three independent, 10 μs MD simulations. Conformational clustering calculation was based on the main-chain atom RMSD of hSPX (2-13). For each cluster, the representative structure was demonstrated. Number in the bracket was the time faction of that conformational cluster. The conformation which satisfied the $T^3$.H-$A^6$.HB distance constraint was highlighted by rectangles.

Figure 12A:
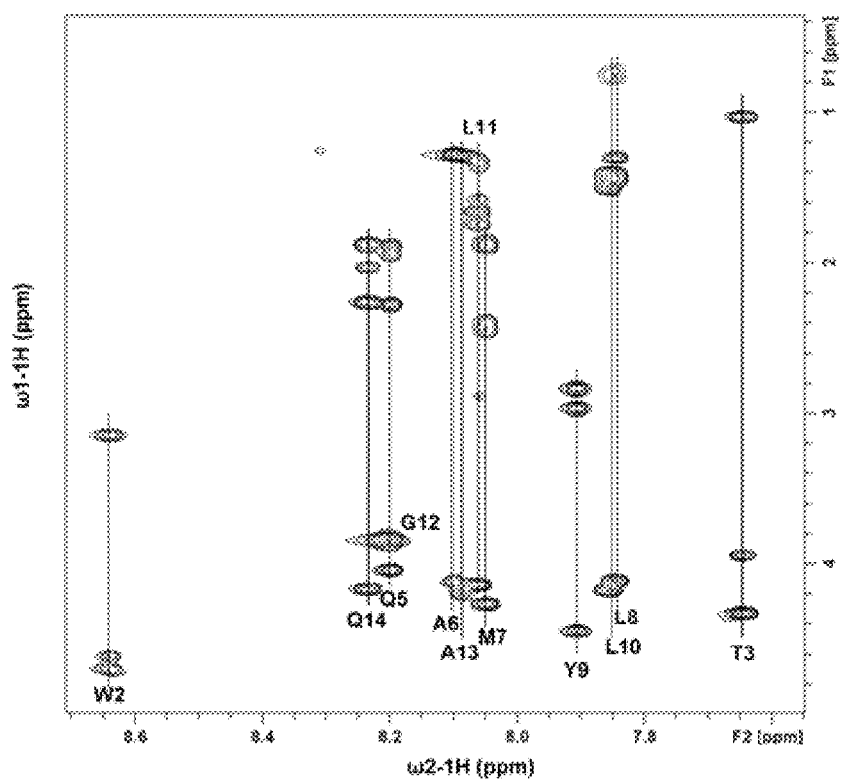

FIG. 12A shows the Identification of amino acid (a.a.) spin systems in hSPX by TOCSY experiments ($H_2O$:$D_2O$ (90:10), 298 K, mixing time: 70 msec). Fingerprint region showing the $C_\alpha$—$N_\alpha H$ $^1H$ NMR cross-peaks of the 2-D TOCSY spectrum of hSPX.

Figure 12B:
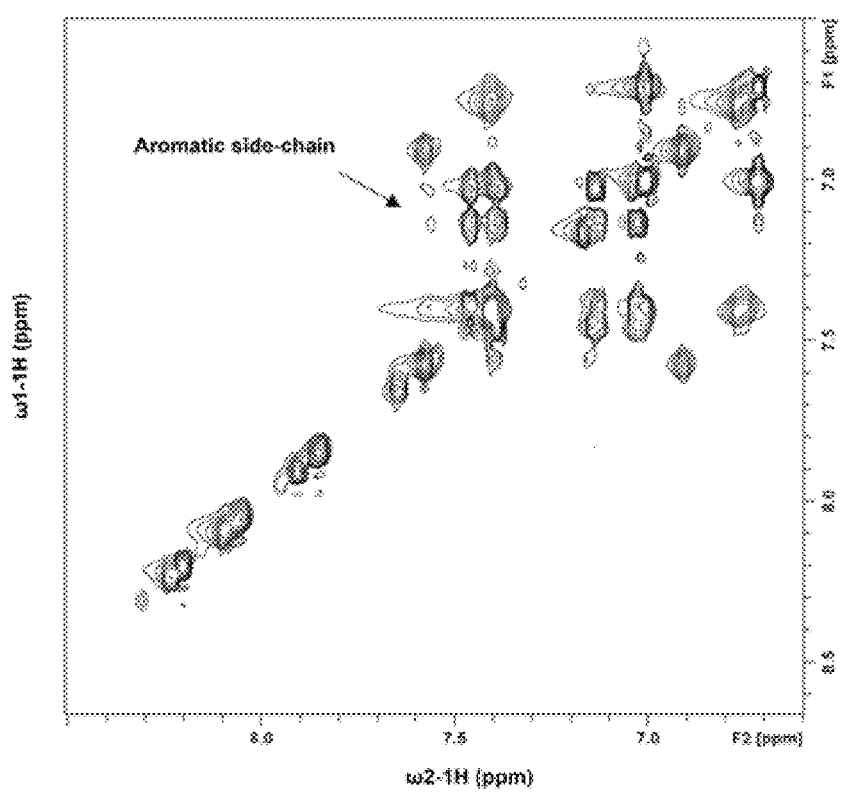

FIG. 12B shows the identification of amino acid (a.a.) spin systems in hSPX by TOCSY experiments ($H_2O$:$D_2O$ (90:10), 298 K, mixing time: 70 msec). NH—NH region $^1H$ NMR cross-peaks of the 2-D TOCSY spectrum of hSPX.

Figure 13A:
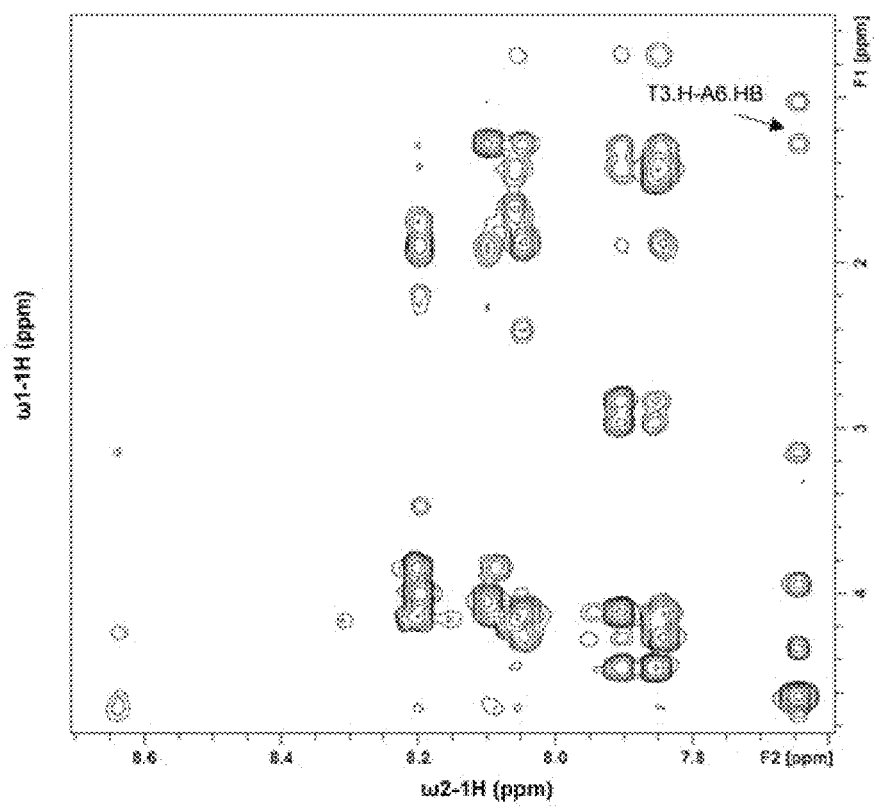

FIG. 13A shows the identification of amino acid (a.a.) distance constraints in hSPX by NOESY experiments ($H_2O$:$D_2O$ (90:10), 298 K, mixing time: 500 msec). Fingerprint region showing the $^1H$ NMR cross-peaks of the 2-D NOESY spectrum of hSPX.

Figure 13B:
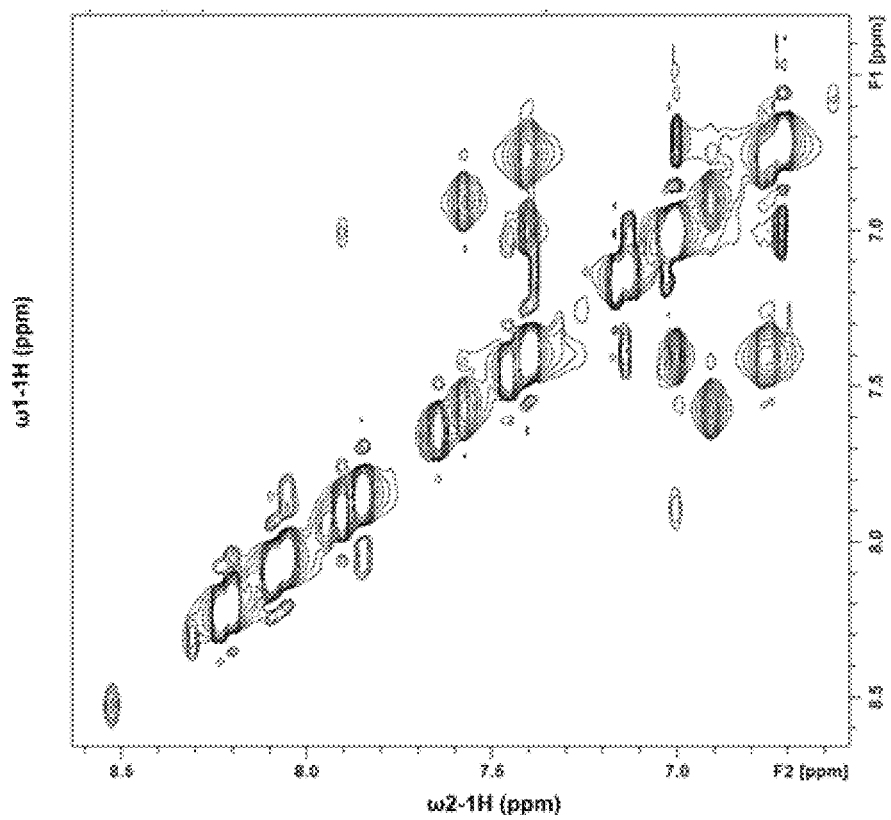

FIG. 13B shows the identification of amino acid (a.a.) distance constraints in hSPX by NOESY experiments ($H_2O$:$D_2O$ (90:10), 298 K, mixing time: 500 msec). NH—NH region showing the $^1H$ NMR cross-peaks of the 2-D NOESY spectrum of hSPX.

Figure 14:
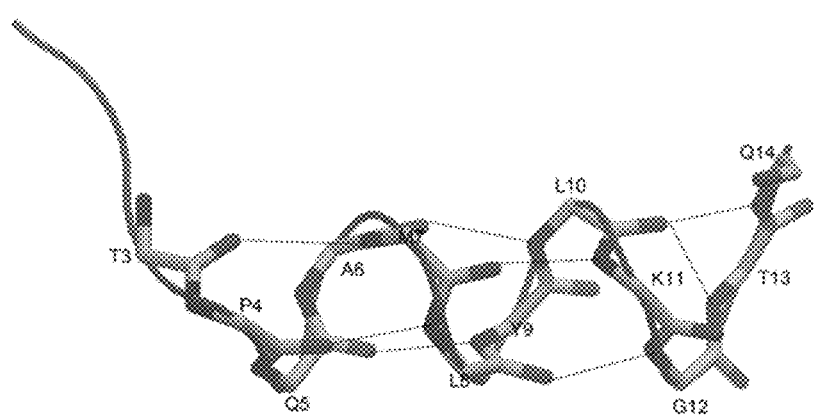

FIG. 14 shows the important intra-molecular interactions that stabilize the α conformation of gSPX solution structure solved by NMR in TFE:water (60:40) solution.

Figure 15:
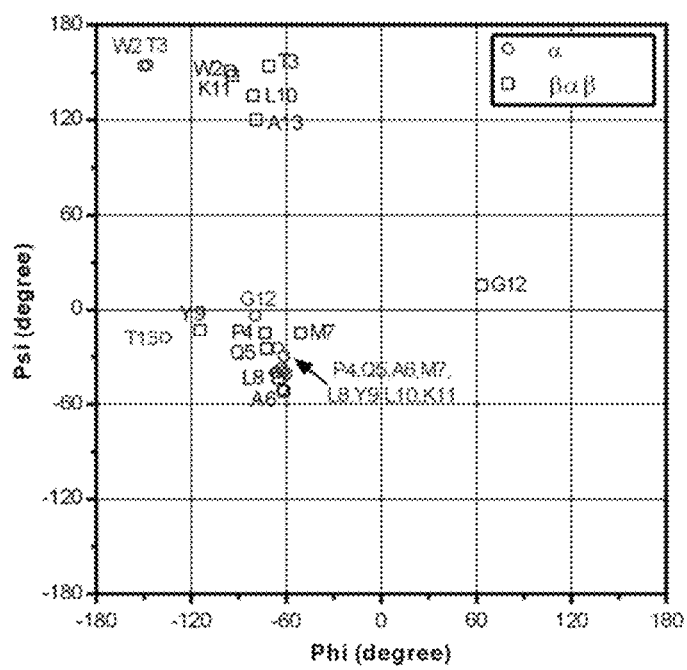

FIG. 15 shows the backbone dihedrals comparison of gSPX α conformation (NMR) and hSPX βαβ conformation (MD+NMR).

Figure 16:
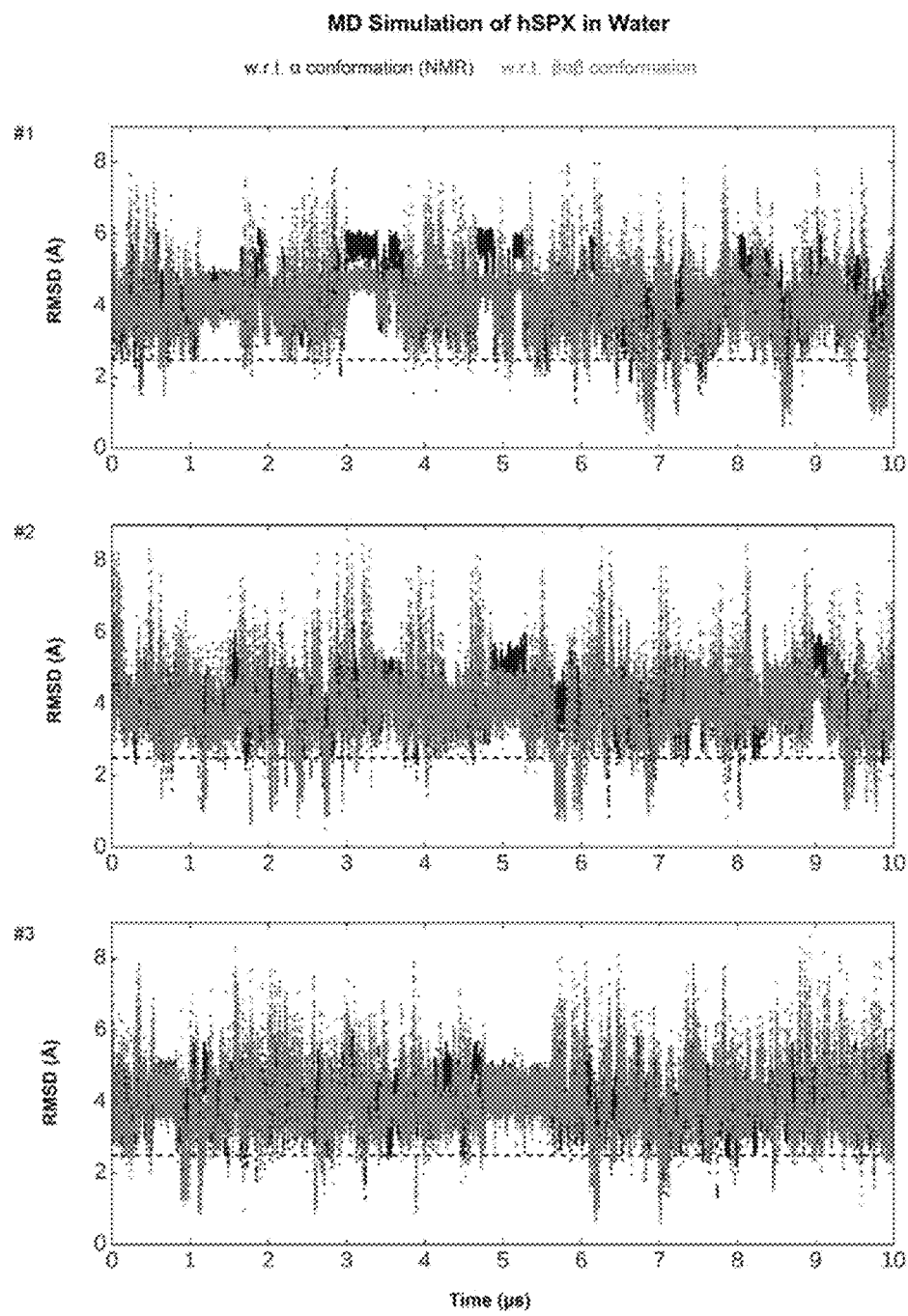
Figure 17:
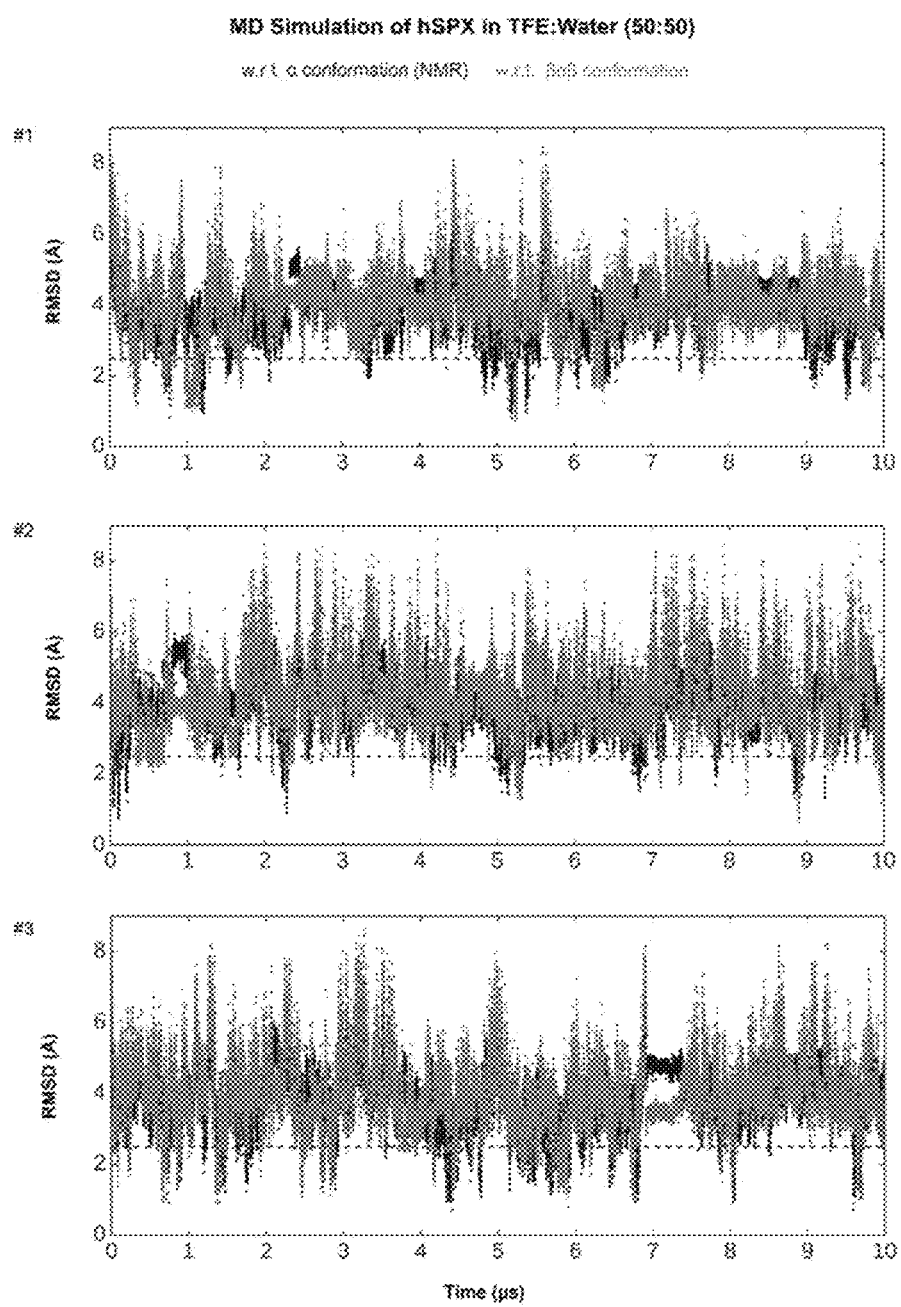
Figure 18A:
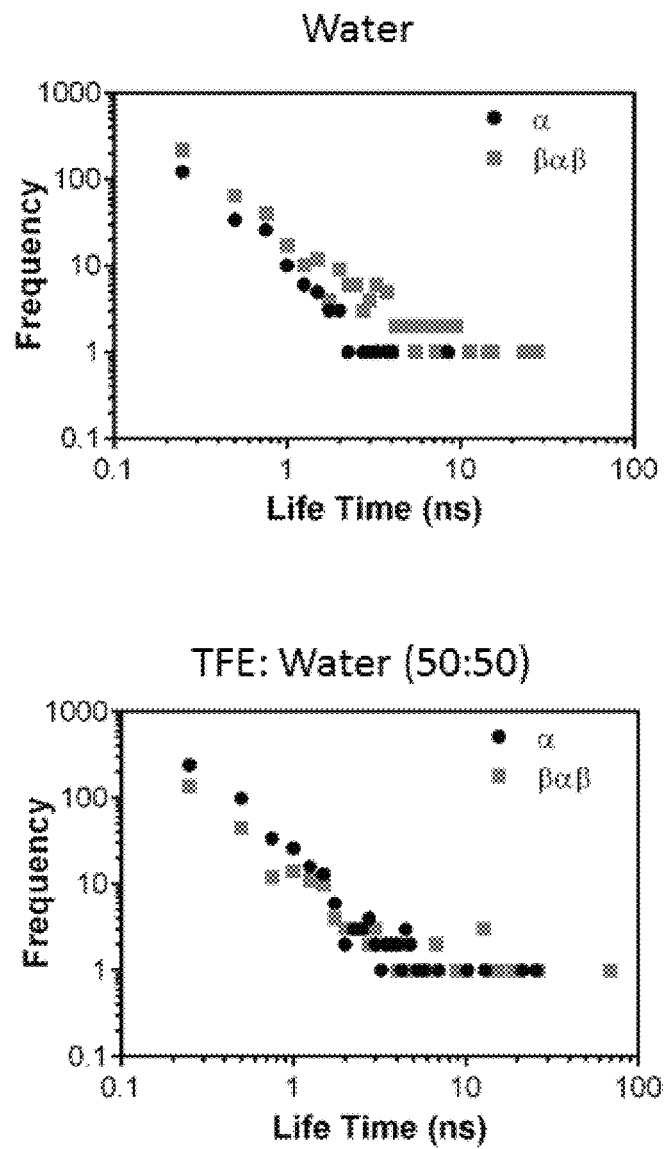
Figure 18B:
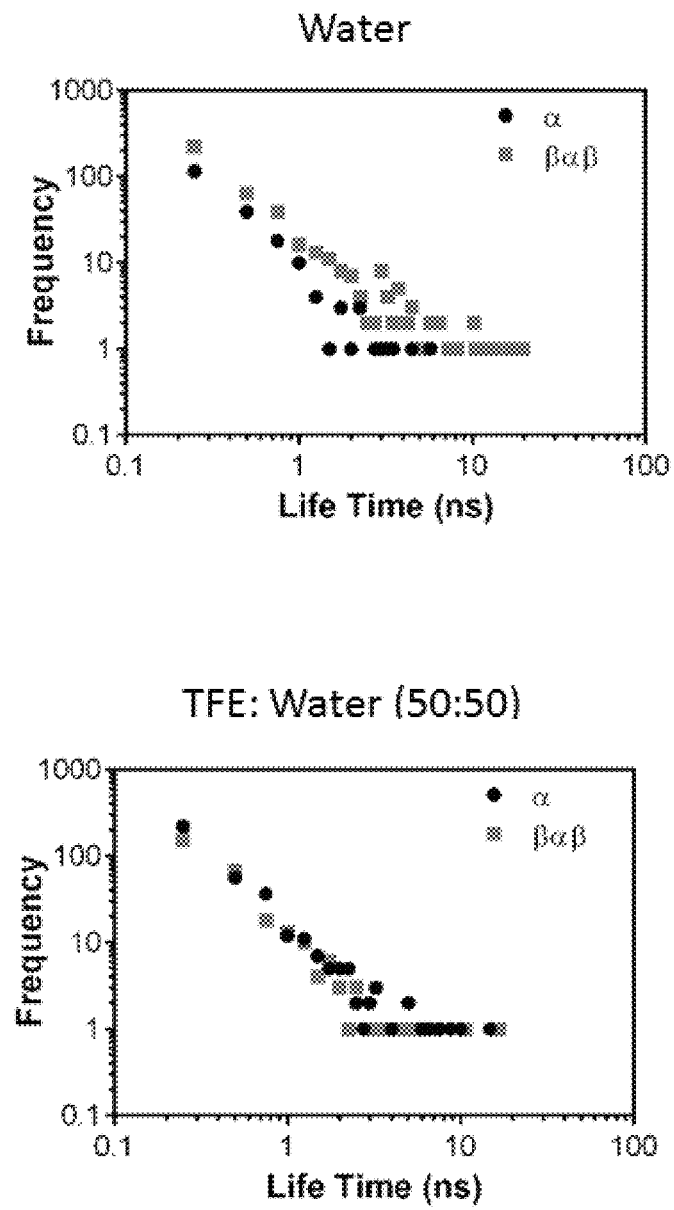
Figure 18C:
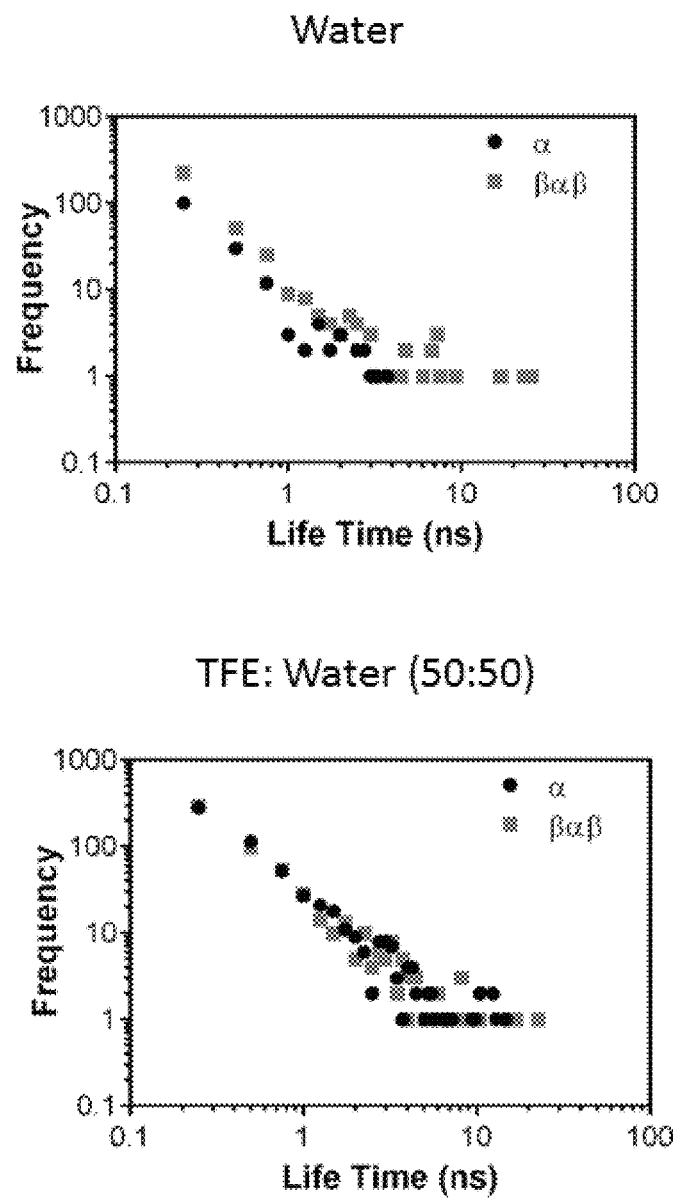

FIG. 16 shows the folding trajectories of hSPX during three independent, 10 μs MD simulations in water. The main-chain atom RMSD of hSPX (2-13) was calculated by comparing with gSPX α conformation and hSPX βαβ conformation.

FIG. 17 shows the folding trajectories of hSPX during three independent, 10 μs MD simulations in TFE:water (50:50). The main-chain atom RMSD of hSPX (2-13) was calculated by comparing with gSPX α conformation and hSPX βαβ conformation.

FIG. 18A shows the life time distribution of two hSPX conformations during the first, 10 μs MD simulations in water and TFE:water (50:50).

FIG. 18B shows the life time distribution of two hSPX conformations during the second, 10 μs MD simulations in water and TFE:water (50:50).

FIG. 18C shows the life time distribution of two hSPX conformations during the third, 10 μs MD simulations in water and TFE:water (50:50).

FIG. 19 shows the identification of hGAL by MALDI-MS spectrum.

FIG. 20 shows the identification of hSPX by MALDI-MS spectrum.

FIG. 21 shows the identification of LH101 by MALDI-MS spectrum.

FIG. 22 shows the identification of LH102 by MALDI-MS spectrum.

FIG. 23 shows the identification of LH101 (Ac) by MALDI-MS spectrum.

FIG. 24 shows the identification of hGAL (1-16) by MALDI-MS spectrum.

FIG. 25 shows the identification of LH201 by MALDI-MS spectrum.

FIG. 26 shows the identification of LH201 (Ac) by MALDI-MS spectrum.

FIG. 27 shows the Ca root-mean-square fluctuation (RMSF) of each residue in cyclic hSPX analog LH101 (Ac) and hSPX during 10 μs MD simulations in water.

FIG. 28 shows the number of conformational clusters of cyclic hSPX analog LH101 (Ac) and hSPX during 10-μs MD simulations in water. Conformational clustering calculation was based on the main-chain atom RMSD of LH101Ac (2-13) or hSPX (2-13).

FIG. 29 shows the representative structures of top 5 conformational clusters of LH101 (Ac) in water during 10 μs MD simulation. Conformational clustering calculation was based on the main-chain atom RMSD of LH101 (Ac) (2-13). For each cluster, the representative structure was demonstrated. Number in the bracket was the time faction of that conformational cluster.

FIG. 30A shows the Identification of a.a. spin systems in LH101 (Ac) by TOCSY experiments ($H_2O$:$D_2O$ (90:10), 298 K, mixing time: 70 msec). Fingerprint region showing the $C_\alpha$—$N_\alpha H$ $^1H$ NMR cross-peaks of the 2-D TOCSY spectrum of LH101 (Ac).

FIG. 30B shows the Identification of a.a. spin systems in LH101 (Ac) by TOCSY experiments ($H_2O$:$D_2O$ (90:10), 298 K, mixing time: 70 msec). NH—NH region $^1H$ NMR cross-peaks of the 2-D TOCSY spectrum of LH101 (Ac).

FIG. 31A shows the identification of a.a. distance constraints in LH101 (Ac) by NOESY experiments ($H_2O$:$D_2O$, 90:10, 298 K, mixing time: 500 msec). Fingerprint region showing the $^1H$ NMR cross-peaks of the 2-D NOESY spectrum of LH101 (Ac).

FIG. 31B shows the identification of a.a. distance constraints in LH101 (Ac) by NOESY experiments ($H_2O$:$D_2O$, 90:10, 298 K, mixing time: 500 msec). NH—NH region showing the $^1H$ NMR cross-peaks of the 2-D NOESY spectrum of LH101 (Ac).

FIG. 32 shows the backbone dihedrals comparison of hSPX βαβ conformation (MD+NMR) and LH101 (Ac) βαβ conformation (MD+NMR).

FIG. 33 shows the representative profile of hSPX degradation in rat serum by RP-HPLC analysis.

FIG. 34 shows the representative profile of cyclic hSPX analog LH101 degradation in rat serum by RP-HPLC analysis.

FIG. 35 shows the representative profile of cyclic hSPX analog LH101 (Ac) degradation in rat serum by RP-HPLC analysis.

FIG. 36 shows the representative profile of hGAL (1-16) degradation products in rat serum by RP-HPLC analysis.

FIG. 37 shows the representative profile of cyclic hGAL (1-16) analog LH201 degradation in rat serum by RP-HPLC analysis.

FIG. 38 shows the representative profile of cyclic hGAL (1-16) analog LH201 (Ac) degradation in rat serum by RP-HPLC analysis.

FIG. 39A shows the serum stability of cyclic analogs of hSPX after 24 hours incubation.

FIG. 39B shows the serum stability of cyclic analogs of hGAL after 24 hours incubation.

FIG. 40 shows the chemical structure of LH201 (Ac).

FIG. 41A shows the MD simulations of hSPX recaptured α-helix and identified another unexpected conformation, the β-hairpin. It represents structures of α- or β-clusters from MD simulation.

Figure 41B:
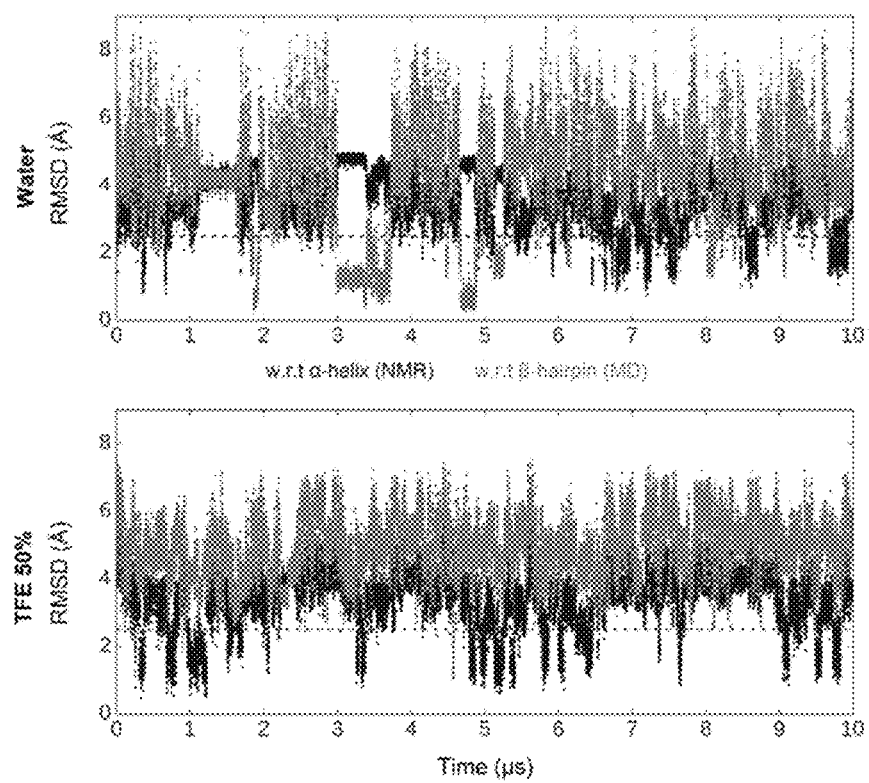

FIG. 41B shows the MD simulations of hSPX recaptured α-helix and identified another conformer, the β-hairpin. It represents folding trajectories of hSPX in water or 50:50 TFE-water solutions in terms of root-mean-square deviation (RMSD) with regard to (w.r.t) the α-helix (NMR) and β-hairpin (MD) conformers.

Figure 41C:
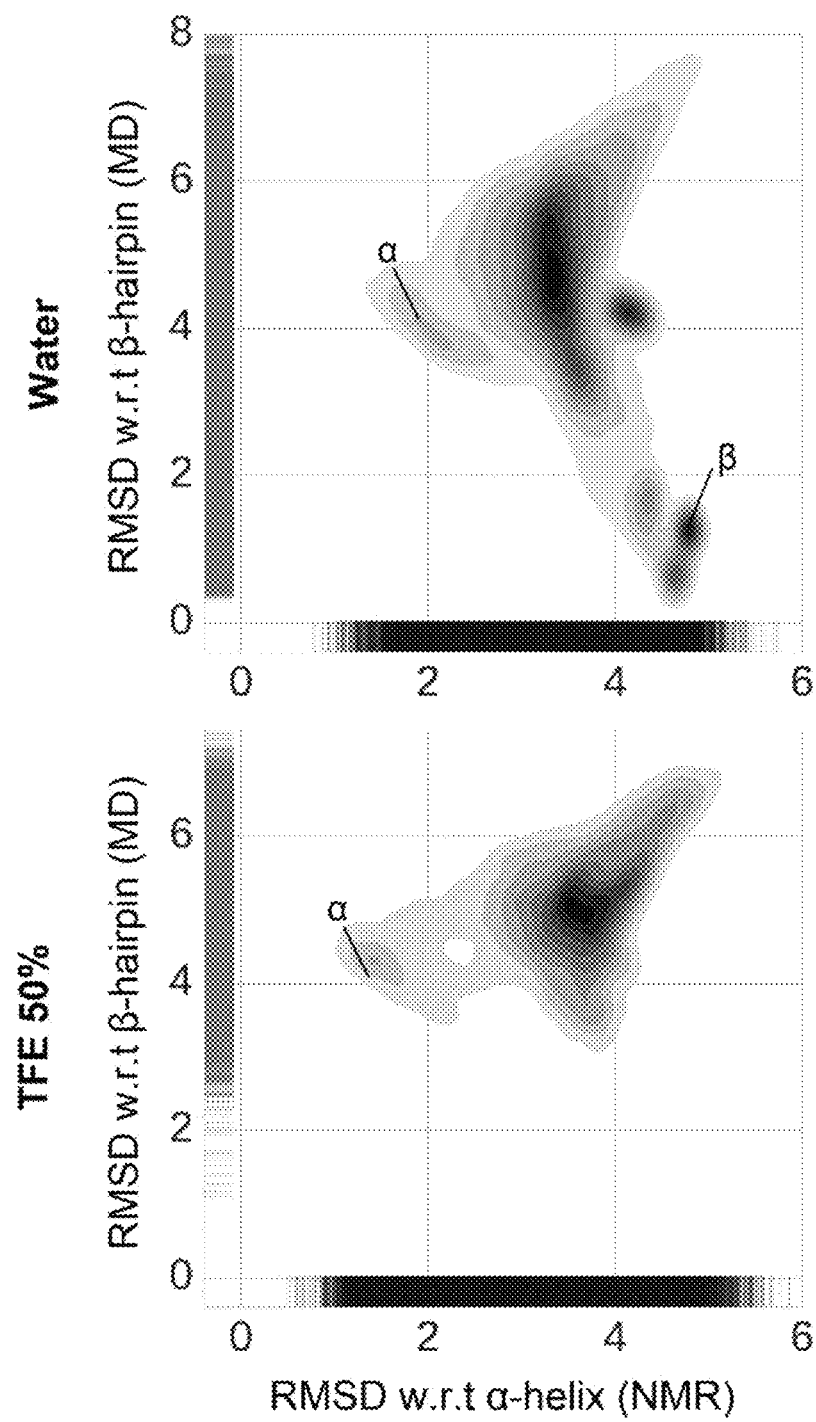

FIG. 41C shows the MD simulations of hSPX recaptured α-helix and identified another conformer, the β-hairpin. It represents conformational space of hSPX in MD simulations. The β conformer was more populated in water, while α conformer was more profound in 50% TFE solution.

FIG. 42 shows the cysteine-scanning of hSPX identified candidate sites for disulfide bonding. Scheme of 14 (C1 to C14) mutant hSPX with single mutation to cysteine at each site.

Figure 43:
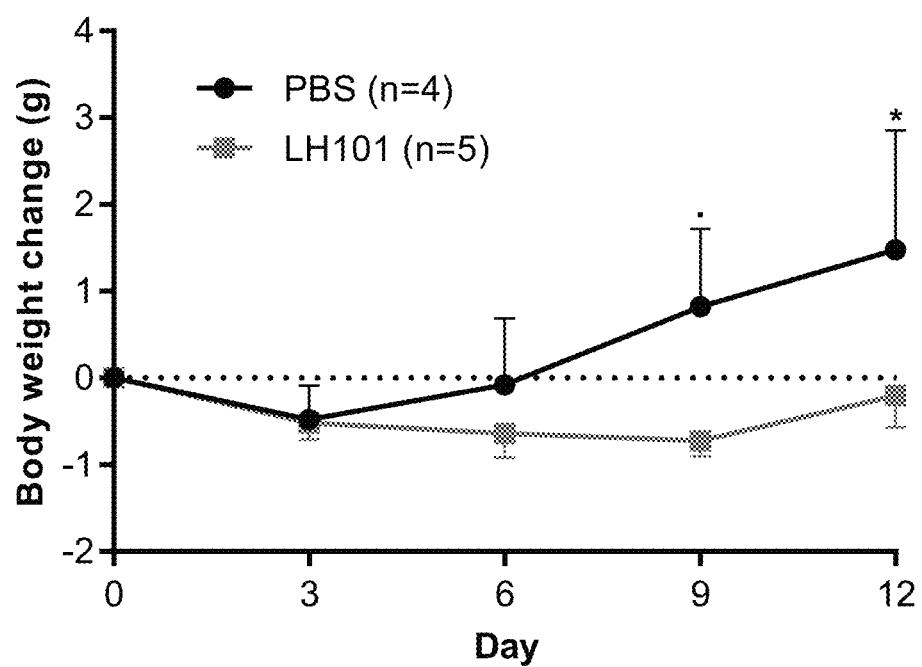

FIG. 43 shows the effect of LH101 on body weight gain in high-fat-diet induced obesity mice compared with phosphate-buffered saline (PBS) treatment.

Figure 44:
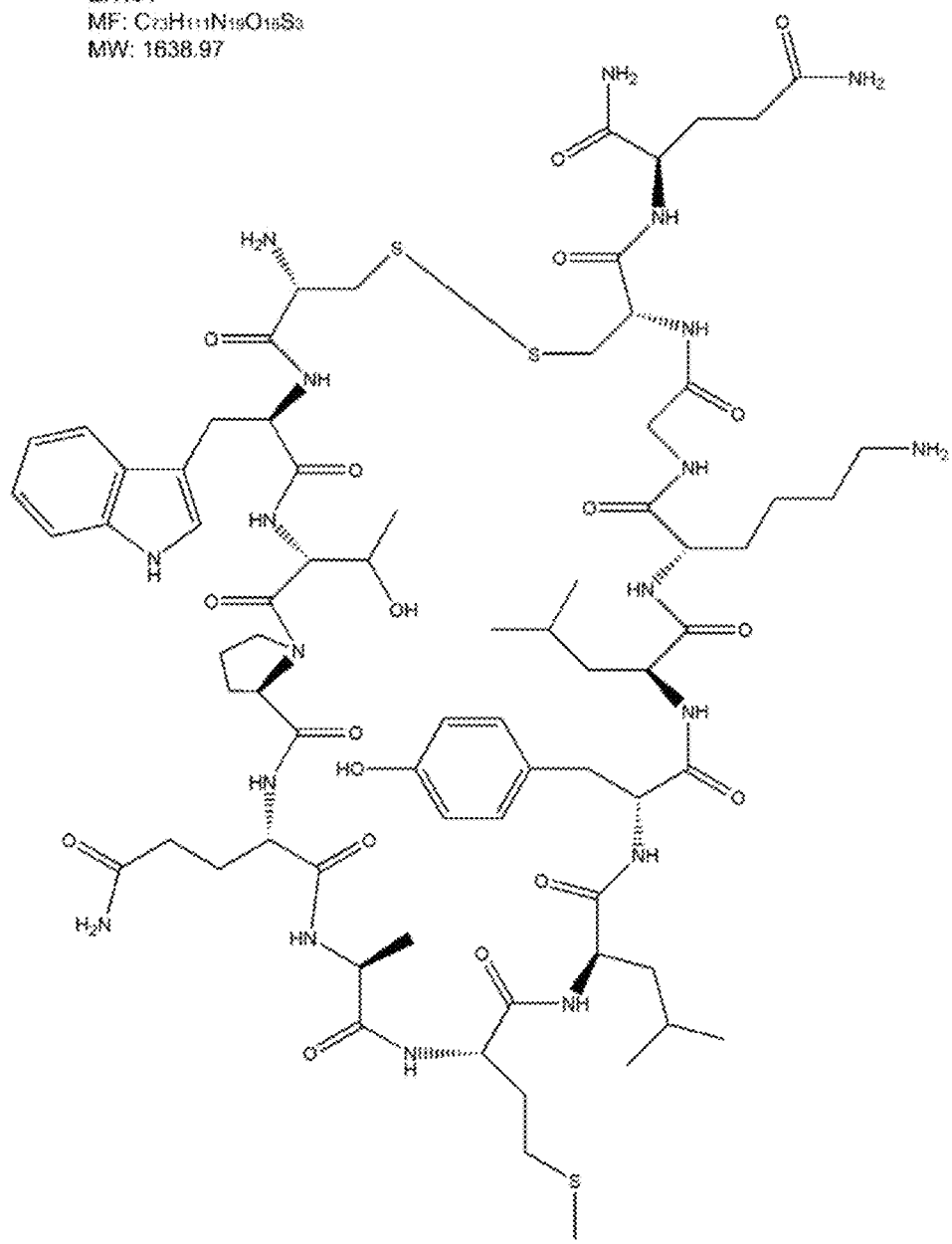

FIG. 44 shows the chemical structure of LH101.

Figure 45:
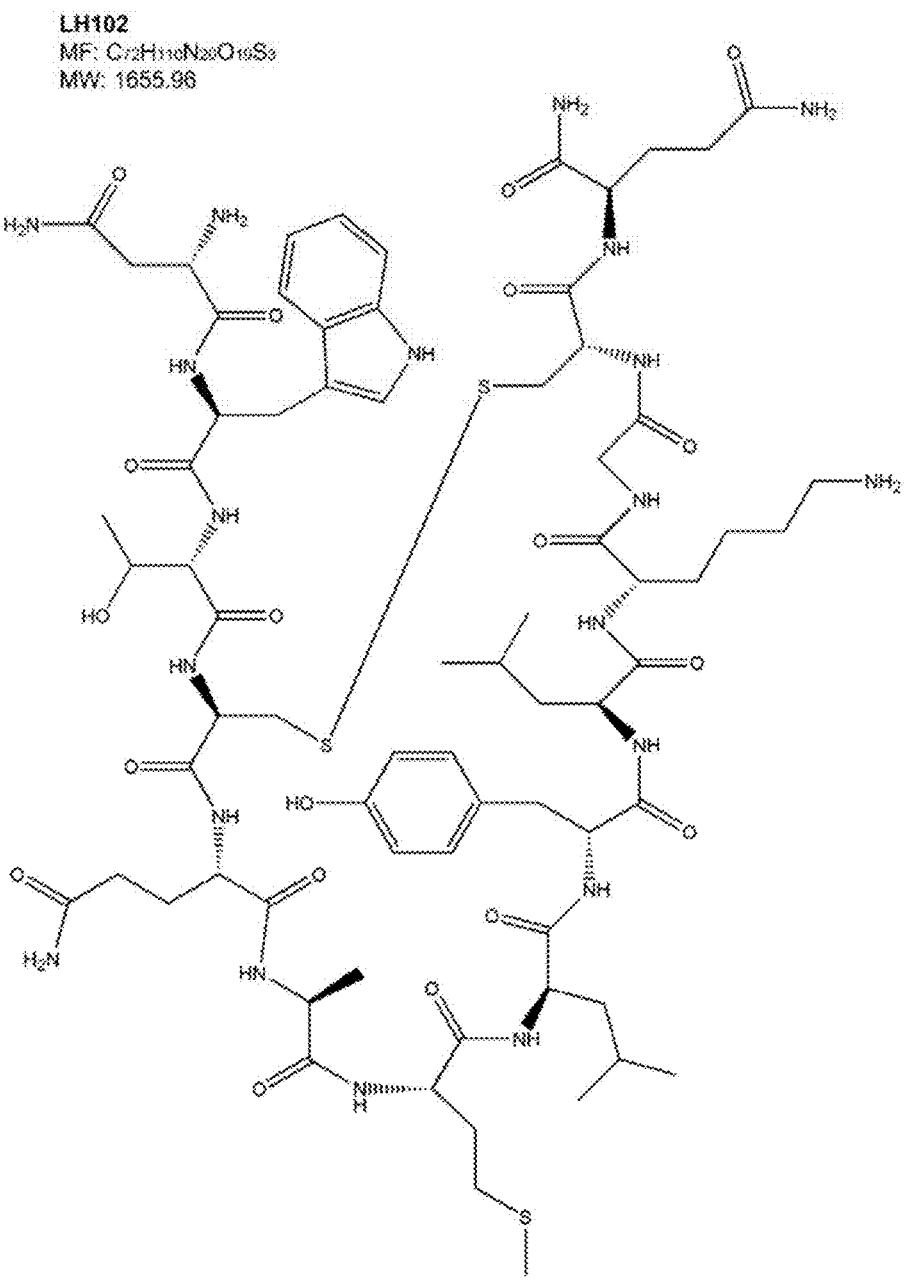

FIG. 45 shows the chemical structure of LH102.

Figure 46:
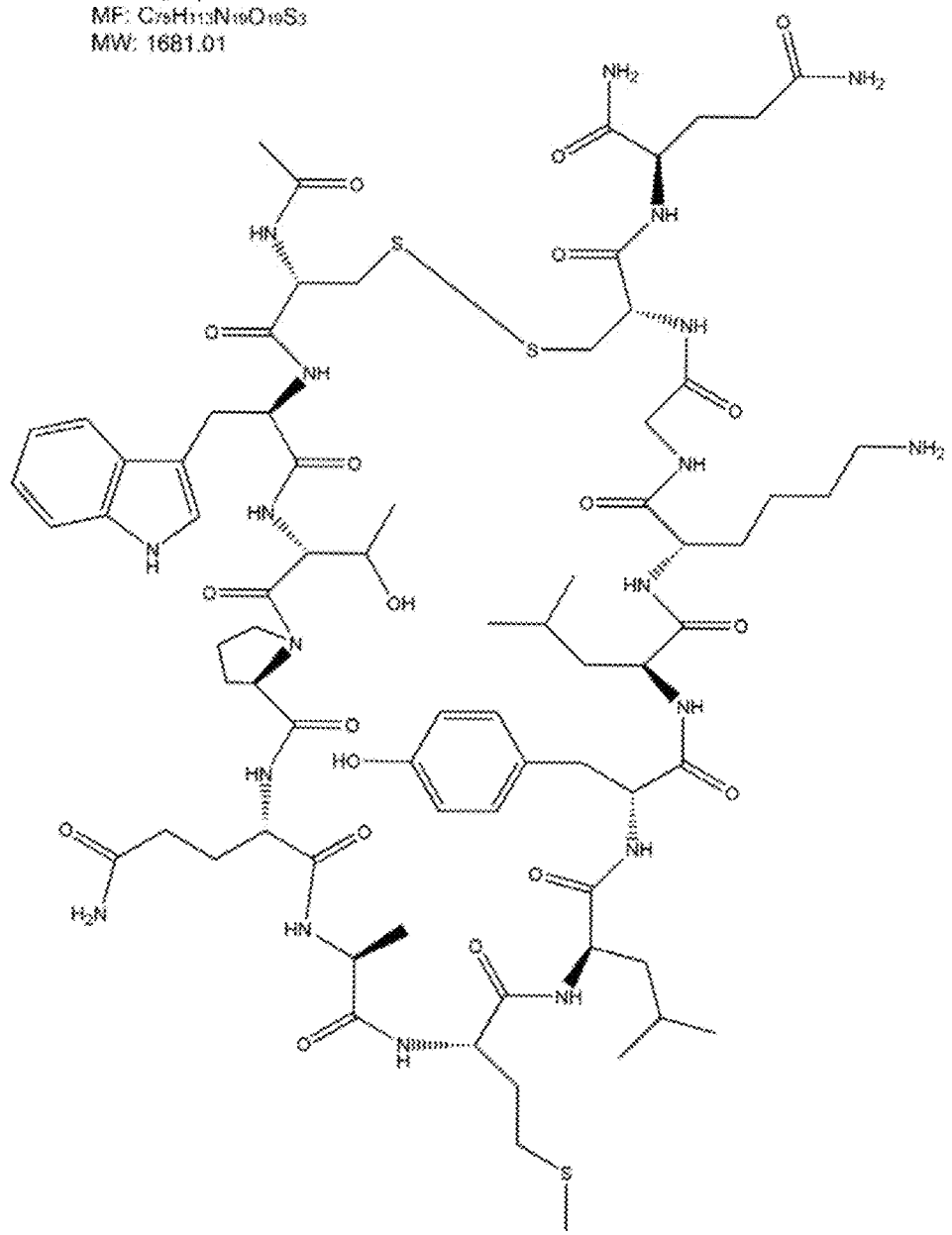

FIG. 46 shows the chemical structure of LH101 (Ac).

Figure 47:
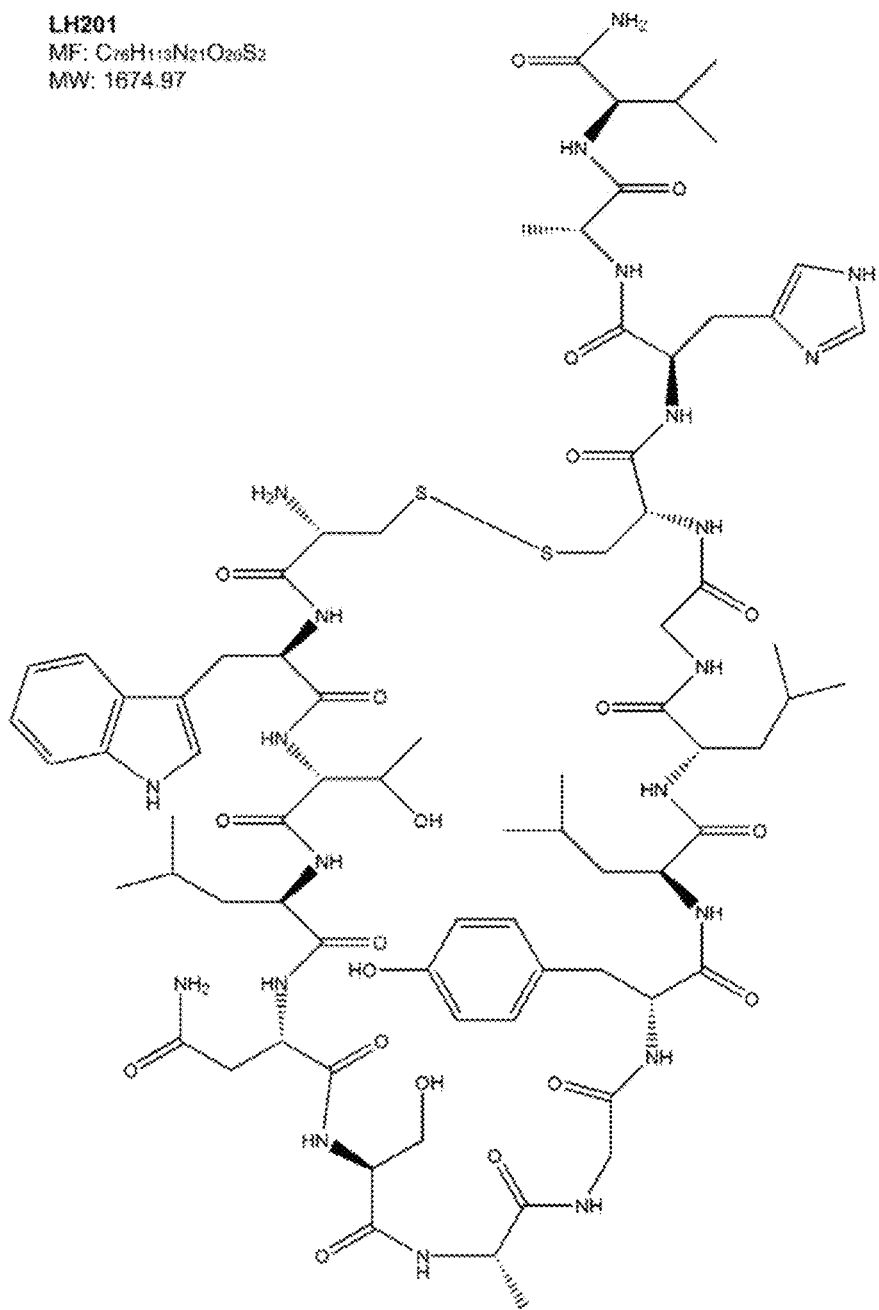

FIG. 47 shows the chemical structure of LH201.

DETAILED DESCRIPTION OF THE INVENTION

The present disclosure is not to be limited in scope by any of the specific embodiments described herein. The following embodiments are presented for exemplification only.

The solution structure of human spexin (hSPX) was investigated by an approach that combines computational and biophysical analysis, which revealed an unexpected β-turn-helix-β-turn βαβ conformation of hSPX that, is different from the previously reported α-helix conformation of goldfish spexin (gSPX). In this conformation, two β turns are connected by a short, nascent a helix, and the N- and C-terminal residues are in extended form and close to each other. Following this finding, cyclic SPX analogs (CSAs) were designed and synthesized, which were expected to adopt the same βαβ conformation as demonstrated by MD simulation and NMR analysis and bear the disulfide bond between the N- and C-terminal residues. These CSAs were proven to be potent activators of GalR2 and GalR3 in serum response element-luciferase (SRE-Luc) assay.

The invention suggested that GalR2 and GalR3 recognize SPX in this conformation. In short, guided by conformational analysis, a novel class of cyclic peptide agonists of GalR2 and GalR3 with improved serum stability and in vivo efficacy were identified.

The investigations of galanin receptors (GalRs) function and the translation of these functions into clinically relevant applications have been hindered by lack of metabolically stable and receptor-specific agonists. Spexin (SPX) is a newly identified neuropeptide which selectively activates GalR2 and GalR3.

In a first aspect of the present disclosure there is provided a cyclic peptide agonist of galanin receptor 2 and galanin receptor 3 comprising a sequence having at least 92.8% homology with SEQ ID NO: 23 or SEQ ID NO: 24; or having at least 93.7% homology with SEQ ID NO: 25 or a therapeutically effective salt thereof, wherein R is hydrogen, alkyl, or acyl with the proviso that SEQ ID NO: 23 must contain cysteine at position one and position thirteen of SEQ ID NO: 23; SEQ ID NO: 24 must contain cysteine at position four and position thirteen of SEQ ID NO: 25; and SEQ ID NO: 25 must contain cysteines at position one and position thirteen of SEQ ID NO: 25.

In certain embodiments the sequence having at least 92.8% homology with SEQ ID NO: 23 or SEQ ID NO: 24; or having at least 93.7% homology with SEQ ID NO: 25 includes a single non-conservative amino acid substitution or a single conservative amino acid substitution.

In certain embodiments, the N-terminal amine of peptides described herein can be represented by the following structure:

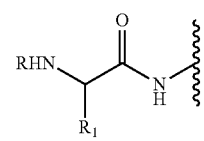

Wherein $R_1$ is an amino acid side chain; —NHR represents the N-terminal amine; and R is hydrogen, alkyl, or acyl.

In certain embodiments, the alkyl can be $(C_1$-$C_{12})$alkyl or $(C_3$-$C_6)$cyclcoalkyl. In other embodiments, the alkyl group can be $(C_1$-$C_{12})$alkyl, $(C_1$-$C_{11})$alkyl, $(C_1$-$C_{10})$alkyl, $(C_1$-$C_9)$alkyl, $(C_1$-$C_8)$alkyl, $(C_1$-$C_7)$alkyl, $(C_1$-$C_6)$alkyl, $(C_1$-$C_5)$alkyl, $(C_1$-$C_4)$alkyl, $(C_1$-$C_3)$alkyl, $(C_3$-$C_5)$cyclcoalkyl, or $(C_3$-$C_4)$cyclcoalkyl.

In certain embodiments, the acyl can be $(C_1$-$C_{12})$alkyl(C=O)— or $(C_3$-$C_6)$cyclcoalkyl(C=O)—. In other embodiments, the alkyl group can be $(C_1$-$C_{12})$alkyl(C=O)—, $(C_1$-$C_{11})$alkyl(C=O)—, $(C_1$-$C_{10})$alkyl(C=O)—, $(C_1$-$C_9)$alkyl(C=O)—, $(C_1$-$C_8)$alkyl(C=O)—, $(C_1$-$C_7)$alkyl(C=O)—, $(C_1$-$C_6)$alkyl(C=O)—, $(C_1$-$C_5)$alkyl(C=O)—, $(C_1$-$C_4)$alkyl(C=O)—, $(C_1$-$C_3)$alkyl(C=O)—, $(C_3$-$C_5)$cyclcoalkyl(C=O)—, or $(C_3$-$C_4)$cyclcoalkyl(C=O)—.

$R_1$ can be the side chain of any naturally occurring amino acid.

In instances where R is hydrogen, the N-terminal amino acid can be covalently attached to an amino terminus modification group, such as PEG (e.g., PEG having a molecular weight of about 1,000, about 3,000, about 5,000, about 10,000, or about 20,000 amu), human serum albumin, or an albumin binding domain.

In a first embodiment of the first aspect of the present disclosure there is provided the peptide wherein said compound is LH101 (SEQ ID NO: 6), LH101 (Ac) (SEQ ID NO: 8), LH102 (SEQ ID NO: 7), LH201 (SEQ ID NO: 10), or LH201 (Ac) (SEQ ID NO: 11) or a therapeutically effective salt thereof.

In a second embodiment of the first aspect of the present invention this is provided the cyclic peptide wherein said compound is comprising of compound LH101 (SEQ ID NO: 6) of molecule formula $C_{73}H_{111}N_{19}O_{18}S_3$ or compound LH101 (Ac) (SEQ ID NO: 8) of molecule formula $C_{75}H_{113}N_{19}O_{19}S_3$ or compound LH102 (SEQ ID NO: 7) of molecule formula $C_{72}H_{110}N_{20}O_{19}S_3$ or compound LH201 of molecule formula $C_{76}H_{113}N_{21}O_{20}S_2$ or compound LH201 (Ac) (SEQ ID NO: 11) of molecule formula $C_{78}H_{115}N_{21}O_{21}S_2$.

The pharmaceutically acceptable salts of the peptides described herein include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the peptides described herein may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.)

Pharmaceutical compositions comprising the peptides disclosed herein may be administered orally, rectally, parenterally, intracisternally, intravaginally, intraperitoneally, topically (as by powders, ointments, drops or transdermal patch), bucally, or as an oral or nasal spray).

Pharmaceutical compositions comprising the peptides disclosed herein can comprise a pharmaceutically acceptable carrier. A "pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

For parenteral administration, the pharmaceutical composition is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation.

Generally, the formulations are prepared by contacting the components of the pharmaceutical composition uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non aqueous vehicles such as fixed oils and ethyl oleate are also useful herein, as well as liposomes. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as poly-sorbates, poloxamers, or PEG.

The components of the pharmaceutical composition to be used for therapeutic administration must be sterile. Sterility is readily accomplished by filtration through sterile filtration membranes (e.g., 0.2 micron membranes). Therapeutic components of the pharmaceutical composition generally are placed into a container having a sterile access port, for example, an intravenous solution bag or vial having a stopper pierceable by a hypodermic injection needle.

The components of the pharmaceutical composition ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized compound(s) using bacteriostatic Water-for-Injection.

The investigations of galanin receptors (GalRs) function and the translation of these functions into clinically relevant applications have been hindered by lack of metabolically stable and receptor-specific agonists. Spexin (SPX) is a newly identified neuropeptide which selectively activates GalR2 and GalR3. To gain insights into structural basis of how spexin is recognized by GalR2 and GalR3 and to develop novel agonists, human spexin solution structure was investigated using a computational approach. All-atom, unbiased, and microsecond molecular dynamics (MD) simulations captured the α-helix conformation, but surprisingly, an unknown β-hairpin conformation was also observed. The β-fold was more stable in water, while α-fold was more profound in hydrophobic solutions. To verify if β-hairpin is biologically active, a series of cyclic peptides were designed, synthesized, and tested. Cysteine-scanning mutagenesis suggested that residue 1, 4, and 13 in spexin were candidate sites for disulfide bonding (FIG. 2B). The novel cyclic peptide agonists of galanin receptor 2 and galanin receptor 3, were further investigated by molecular dynamics (MD) simulations and NMR analysis, which suggested that human spexin (hSPX) adopts a β-turn-helix-β-turn (βαβ) conformation in solution, which was unexpected based on a previously reported α-helix conformation for goldfish spexin (gSPX). Consistent with this conformation, cyclic analogs of hSPX with a disulfide bond between residue 1 and 13, LH101 (CWTPQAMLYLKGCQ-NH$_2$ (SEQ ID NO: 6)), activated both GalR2 (EC$_{50}$=1.19 µM) and GalR3 (EC$_{50}$=1.56 µM) with potency comparable to wild type, and that the acetylation at the N-terminal, LH101(Ac) (Ac-CWTPQAMLYLKGCQ-NH$_2$ (SEQ ID NO: 8)) raises the potency EC$_{50}$=0.38 µM on GalR2 and EC$_{50}$=0.39 µM on GalR3. MD and NMR results confirmed that the βαβ conformation was the major form adopted by LH101 (Ac). Moreover, cyclic peptide LH201 (CWTLNSAGYLLG CHAV-NH$_2$(SEQ ID NO: 10)) derived from human galanin (1-16), was found to be a selective agonist of GalR2 (EC50=0.12 µM) at nanomolar dose. The serum half-lives of LH101 ($t_{1/2}$=355.7 min) and LH101 (Ac) (SEQ ID NO: 8) ($t_{1/2}$=1973.7 min) were significantly longer and more stable than the wild type ($t_{1/2}$=66.5 min), and LH101 and LH101

(Ac) demonstrate better efficacy than the wild type in body weight gain control of high-fat-diet (HFD) induced obese mice. In high-fat-diet obesity mice model, LH101 and LH101 (Ac) significantly suppressed the body weight gain compared with control group injected with phosphate-buffered saline (PBS). These results supported the notion that β-hairpin might be an active conformation of spexin or galanin recognized by GalR2 and GalR3. More importantly, a novel class of GalR2 and GalR3 cyclic agonists was discovered. LH101, LH102 and LH101 (Ac) are potent spexin analogs with prolonged action, which hold the potential to be developed as novel therapies for spexin-deficient disorders, such as obesity.

Spexin-deficient disorders include those diseases and/or disorders that can be treated by agonizing GalR2 and/or GalR3.

Diseases and/or disorders that can be treated by agonizing GalR2 and/or GalR3 include, but are not limited to attention deficit hyperactivity disorder (ADHD), bipolar disorder, body dysmorphic disorder, bulimia nervosa eating disorder, cataplexy, dysthymia, anxiety disorders, irritable bowel syndrome (IBS), impulse control disorders, pathological gambling problem, kleptomania, migraines, major depressive disorder, narcolepsy, obsessive-compulsive disorder (OCD), chronic pain, drug abuse, addiction, Alzheimer's disease, pain, seizures, learning and memory, anxiety, overeating, and obesity and the like. Additional diseases and/or disorders that can be treated by agonizing GalR2 and/or GalR3 are recited in U.S. Pat. No. 9,057,726, which is incorporated herein by reference Results Folding Simulations of hSPX Captured α-Helix and β-Hairpin Conformation To understand the folding process of hSPX, 10-μs MD simulations were performed in pure water and water-TFE (50:50) mixture solutions, which mimics the Nuclear Magnetic Resonance (NMR) solution conditions as well as cell membrane environment. With 14 amino acids, this short peptide was extremely flexible in solution. However, conformation clustering results indicated that it folded into several major conformations. Similar with goldfish spexin solved by NMR, the largest conformation cluster of hSPX in 50% TFE solution was α-helix (FIG. 41A). MD simulations recaptured major features suggested by NMR-extended in the first four residues but helixed in the remaining ones. However, this computation-predicted α-helix conformer was slightly different from the NMR-solved one: the last three residues were in distorted α-helix, sometimes even random coiled (FIG. 41A), which suggested that C-terminal of hSPX may not be that rigid as indicated by NMR models. In parallel, the hSPX folding in pure water was studied. Unexpectedly, conformation clustering results suggested the most popular conformer of hSPX was a typical β-hairpin (FIG. 41A) in aqueous solution. From Asn1 to Ala13, the first 13 amino acids of hSPX formed antiparallel β sheets with five residues at each strand, while Ala6, Met7, and Leu8 constituted β-turn to link both sheet. This β conformer was rare but more stable—sometimes even can last for hundreds of nanoseconds (FIG. 41B). In contrast, α conformer can be frequently reached, but only last for several nanoseconds (FIG. 41B). Moreover, the β conformer was more popular in water, while the α conformer was more prominent in 50% TFE solution (FIG. 41C). Although in different solution environment, it was surprising that one such short peptide can adopt two distinct conformations. One important question is: could the β-hairpin be a biologically active conformation of hSPX recognized by GalR2 and GalR3? To answer this crucial question, disulfide bonding was used to staple hSPX.

MD Simulations and NMR Analysis Suggested a βαβ hSPX Conformation

Experimental and theoretical studies have indicated that α-helix is the primary conformation of hGAL N-terminal fragment. The structure of goldfish spexin (gSPX) in solution has been solved by NMR, where the α-helix spans the distance from $Q^5$ to $Q^{14}$. Circular dichroism (CD) experiments have indicated that gSPX in water has α-helix, and that increasing the 2,2,2-trifluoroethanol (TFE) concentration also increases the α-helix content. hSPX is expected to have the same α-helix conformation, which may be stabilized by TFE. To verify this, three independent, all-atom MD simulations of hSPX (10 μs each) in pure water or in TFE: water (50:50) solutions at 298 K were performed.

With 14 amino acids, hSPX was flexible in both water and TFE:water (50:50) during MD simulations (FIG. 7). The Cα atom root-mean-square fluctuation (RMSF) analysis suggested that $N^1$ and $Q^{14}$ were the most flexible residues, and $N^1$, $W^2$, $Q^5$, and $A^6$ can be stabilized by adding TFE into water (FIG. 7). Conformational clustering calculation was performed based on the main-chain atom of hSPX with a hierarchical agglomerative approach (minimum distance≤2.5 Å), and the conformational clusters were ranked according to the fraction of total life time. The number of clusters of hSPX in TFE:water (50:50) as an indicator of conformation diversity was significantly less ($p<0.01$) than that of hSPX in water (FIG. 8 and Table 1), consistent with the notion of TFE is a structural stabilizing solvent.

TABLE 1

Number of conformation clusters of hSPX in MD simulations.

| MD simulation | Water | TFE:Water (50:50) |
| --- | --- | --- |
| # 1 | 611 | 384 |
| # 2 | 605 | 463 |
| # 3 | 585 | 477 |

It was expected that the α-helix conformation of gSPX was of the high ranking (more populated) clusters; however, this is not the case for hSPX, neither in water nor in TFE:water (50:50). The α-helix conformation was hardly found in water; while in TFE:water (50:50), it was ranked at 11, 10 and 6 (FIG. 9), respectively. The top-ranking conformational clusters, unexpectedly, represent diverse conformers containing (3 turns (FIGS. 10 and 11).

NMR analysis was then performed for hSPX in water at 298 K. With 2D $^1$H—$^1$H Total Correlated SpectroscopY (TOCSY) experiments, the hydrogen atom chemical shifts of most hSPX residues (except $N^1$) were successfully assigned (FIGS. 12A-12B, Table 2). Meanwhile, the 2D $^1$H—$^1$H Nuclear Overhauser Effect Spectroscopy (NOESY) experiments were also performed to detect if there were any distance constraints between these hydrogen atoms (FIGS. 13A and 13B). Although almost all identified NOE signals appeared to result from intra-residue or neighboring-residue hydrogen atoms, a strong NOE formed between $T^3$.H and $A^6$.HB was identified (FIG. 1A). The volume of $T^3$.H-$A^6$.HB NOE ($2.0 \times 10^6$) was of the same order as $T^3$.H-$T^3$.HG ($2.3 \times 10^6$), suggesting that the distance between $T^3$.H and $A^6$.HB was less than 5 Å. Among the top 5 conformational clusters generated by MD, one of them was found to satisfy this NOE constraint (Tables 3 and 5), which was repeatedly seen in simulations in water (ranking 2, 1, and 3, FIG. 10 and Table 3) and in TFE:water (50:50) (ranking 2, 1, and 1, FIG. 11 and Table 4).

TABLE 2

$^1$H assignment and chemical shifts for hSPX in aqueous solution at 298K.

| Residue | NH | αH | βH | γH | δH | Others |
|---|---|---|---|---|---|---|
| N1 | | | | | | |
| W2 | 8.646 | 4.621 | 3.262, 3.151 | | 7.173 | 10.029, 7.459 7.398, 7.034 7.140 |
| T3 | 7.654 | 4.332 | 3.945 | 1.035 | | |
| P4 | | 3.996 | 2.187 | 1.852, 1.785 | 3.475, 3.331 | |
| Q5 | 8.205 | 4.048 | 1.954, 1.888 | 2.280 | | |
| A6 | 8.105 | 4.118 | 1.284 | | | |
| M7 | 8.053 | 4.270 | 1.889 | 2.447, 2.407 | | |
| L8 | 7.848 | 4.115 | 1.428 | 1.309 | 0.779, 0.714 | |
| Y9 | 7.911 | 4.451 | 2.972, 2.837 | | | HD*, 7.011 HE*, 6.724 |
| L10 | 7.859 | 4.180 | 1.502, 1.429 | 1.408 | 0.780, 0.740 | |
| K11 | 8.066 | 4.142 | 1.749, 1.675 | 1.329 | 1.578 | EH, 2.891 ζNH$_3^+$, 7.442 |
| G12 | 8.209 | 3.845 | | | | |
| A13 | 8.093 | 4.201 | 1.290 | | | |
| Q14 | 8.240 | 4.172 | 2.036, 1.881 | 2.267 | | |

TABLE 3

The distances between T$^3$.H and A$^6$.HB in top 5 conformational clusters of hSPX in water during MD simulations.

| Conformational cluster | T$^3$.H-A$^6$.HB distance (Å) | | |
|---|---|---|---|
| | #1 | #2 | #3 |
| Top 1 | 12.17, 12.65, 13.41 | 2.53, 2.50, 3.90 | 5.17, 6.73, 6.79 |
| Top 2 | 3.87, 3.99, 4.85 | 11.25, 11.82, 12.77 | 10.42, 11.29, 11.44 |
| Top 3 | 6.20, 6.51, 7.18 | 11.21, 11.35, 12.64 | 3.48, 3.63, 4.67 |
| Top 4 | 5.71, 5.93, 6.78 | 9.87, 10.12, 10.62 | 9.70, 10.96, 11.24 |
| Top 5 | 10.36, 11.41, 11.43 | 9.98, 10.68, 11.50 | 10.06, 10.65, 11.47 |

TABLE 4

The distances between T$^3$.H and A$^6$.HB in representative conformation for top 5 conformational clusters of hSPX in TFE:water (50:50) during MD simulations.

| Conformational cluster | T$^3$.H-A$^6$.HB distance (Å) | | |
|---|---|---|---|
| | #1 | #2 | #3 |
| Top 1 | 11.42, 11.58, 12.53 | 2.13, 3.25, 3.74 | 3.27, 3.95, 4.81 |
| Top 2 | 2.64, 3.75, 4.26 | 10.31, 11.68, 11.71 | 11.72, 12.45, 13.09 |
| Top 3 | 9.80, 11.04, 11.22 | 10.35, 10.96, 11.84 | 9.80, 11.20, 11.11 |
| Top 4 | 11.50, 12.51, 12.99 | 9.32, 10.40, 11.02 | 2.36, 2.60, 3.67 |
| Top 5 | 10.28, 10.38, 11.67 | 6.21, 6.56, 6.93 | 11.61, 11.68, 12.89 |

The overall main-chain atom root-mean-square deviation (RMSD) between this new conformation and gSPX α-helix conformation was 6.53 Å, which share local structural similarity from T$^3$ to Y$^9$ (FIG. 1B and Table 5). Different from the gSPX α-helix conformation (FIG. 14), this new conformation was stabilized by two i–i+3 backbone hydrogen bonds: $T^3$.O-$A^6$.H and $A^6$.O—$Y^9$.H (FIG. 1C). Meanwhile the hydrogen bond between $A^6$.O-$L^{10}$.H can also be observed (FIG. 1C). The backbone dihedral angle analysis suggests that the dihedrals of $P^4$ to $L^8$ are in the α-helix region, while that of $W^2$, $T^3$, $L^{10}$, $K^{11}$, and $A^{13}$ are in the extended region (FIG. 15, Table 6). In other words, this new conformation is characterized by two β turns ($T^3$ to $A^6$ and $A^6$ to $Y^9$) connected by a short, nascent helix ($P^4$ to $L^8$). To distinguish this from the gSPX α conformation, we named the new one "βαβ conformation". An important feature of the βαβ conformation is that the N- and C-terminal residues are close to each other, which is stabilized by the hydrophobic stacking between $W^2$ and $L^{10}$ side chains (FIG. 1C).

TABLE 5

The main-chain atom RMSD between hSPX βαβ conformation (MD + NMR) and gSPX α conformation (NMR).

| Residue | RMSD (Å) |
|---|---|
| N1 | 4.94 |
| W2 | 3.15 |
| T3 | 0.59 |
| P4 | 0.39 |
| Q5 | 0.33 |
| A6 | 0.27 |
| M7 | 0.32 |
| L8 | 1.11 |
| Y9 | 2.02 |
| L10 | 2.85 |
| K11 | 7.14 |
| G12 | 12.05 |
| A13/T13[1] | 12.44 |
| Q14 | 14.05 |
| Overall | 6.53 |

[1]The $13^{th}$ residue in hSPX is Ala, while it is Thr in gSPX.

TABLE 6

The backbone dihedrals of α conformation (gSPX, NMR) and βαβ conformation (hSPX, MD + NMR).

| Residue | α Phi (degree) | α Psi (degree) | βαβ Phi (degree) | βαβ Psi (degree) |
|---|---|---|---|---|
| W2 | −150.1 | 154.3 | −95.6 | 151.0 |
| T3 | −148.1 | 154.7 | −71.3 | 153.9 |
| P4 | −65.4 | −24.4 | −73.3 | −14.7 |
| Q5 | −60.2 | −40.7 | −72.6 | −24.7 |
| A6 | −62.1 | −39.7 | −61.8 | −51.7 |
| M7 | −67.1 | −39.8 | −51.0 | −14.7 |
| L8 | −63.0 | −37.6 | −64.9 | −43.2 |

TABLE 6-continued The backbone dihedrals of α conformation (gSPX, NMR) and βαβ conformation (hSPX, MD + NMR).

| Residue | α | | βαβ | |
|---|---|---|---|---|
| | Phi (degree) | Psi (degree) | Phi (degree) | Psi (degree) |
| T9 | −66.3 | −40.2 | −114.6 | −13.0 |
| L10 | −62.5 | −50.6 | −81.2 | 135.4 |
| K11 | −61.6 | −29.8 | −94.0 | 147.8 |
| G12 | −79.7 | −3.5 | 63.3 | 15.7 |
| A13/T13[1] | −136.4 | −17.5 | −79.1 | 120.2 |

[1] The 13th residue in hSPX is Ala, while it is Thr in gSPX.

The folding kinetics of hSPX α and βαβ conformations were also investigated using MD simulation data (FIGS. 16-17, 18A-18C, Table 7). The folding rate (defined by the number of folding events during a certain time window) of the α conformation in water was $19.4\pm2.7$ $\mu s^{-1}$, which was significantly lower than that of βαβ conformation in water ($41.1\pm4.4$ $\mu s^{-1}$, p<0.01) (FIG. 1D). Interestingly, in TFE: water (50:50), the folding rate of α conformation was dramatically increased to $48.0\pm10.9$ $\mu s^{-1}$ (p<0.05), while there was no change in that of the βαβ conformation ($38.4\pm17.6$ $\mu s^{-1}$) (FIG. 1D). The average life time of α conformation in water was $0.58\pm0.03$ ns, which was also increased in TFE:water (50:50) ($0.83\pm0.13$ ns, p<0.05) (FIG. 1E). In contrast, the average life time of βαβ conformation in water was $1.16\pm0.21$ ns, significantly higher than that of α conformation (p<0.01), but no change was found in TFE:water (50:50) ($1.14\pm0.47$) (FIG. 1E). Collectively, the fraction of total life time of α conformation was increased from $1.1\pm0.2\%$ to $4.8\pm1.3\%$; while for βαβ conformation, it remained ($4.1\pm1.5\%$ and $4.2\pm1.8\%$, in water and TFE:water (50:50)) (FIG. 1F). The folding kinetics data suggest that TFE enhances the helix structure, which is in line with many studies.

TABLE 7

Statistics of folding events for α- and βαβ conformations of hSPX in 10 μs MD simulations.

| Solvent | MD run | α | | | | βαβ | | | |
|---|---|---|---|---|---|---|---|---|---|
| | | # of folding events | Average life time (ns) | Maximum life time (ns) | Accumulated life time (ns) | # of folding events | Average life time (ns) | Maximum life time (ns) | Accumulated life time (ns) |
| Water | #1 | 217 | 0.60 | 8.50 | 131.00 | 433 | 1.19 | 27.75 | 515.50 |
| | #2 | 200 | 0.58 | 5.75 | 115.00 | 439 | 1.35 | 19.50 | 591.50 |
| | #3 | 164 | 0.55 | 3.75 | 90.75 | 360 | 0.93 | 25.50 | 336.25 |
| TFE: Water (50:50) | #1 | 469 | 0.83 | 25.75 | 388.00 | 272 | 1.66 | 69.25 | 450.75 |
| | #2 | 377 | 0.71 | 14.75 | 268.50 | 292 | 0.76 | 16.75 | 221.50 |
| | #3 | 594 | 0.96 | 14.75 | 572.75 | 587 | 1.00 | 22.75 | 586.00 |

It is concluded that hSPX commonly adopts the βαβ conformation in solution, but the question remained as to whether the conformation is the biologically active conformation recognized by GalR2 and GalR3? To answer this crucial question, cyclic peptides stapled by a disulfide bond were prepared. The flexibility of hSPX could be reduced by cyclic arrangement, and it will be easier to understand the conformation-activity relationships.

Cyclic Analogs of hSPX Retain the Activation Profile on GalR2 and GalR3

Figure 19:
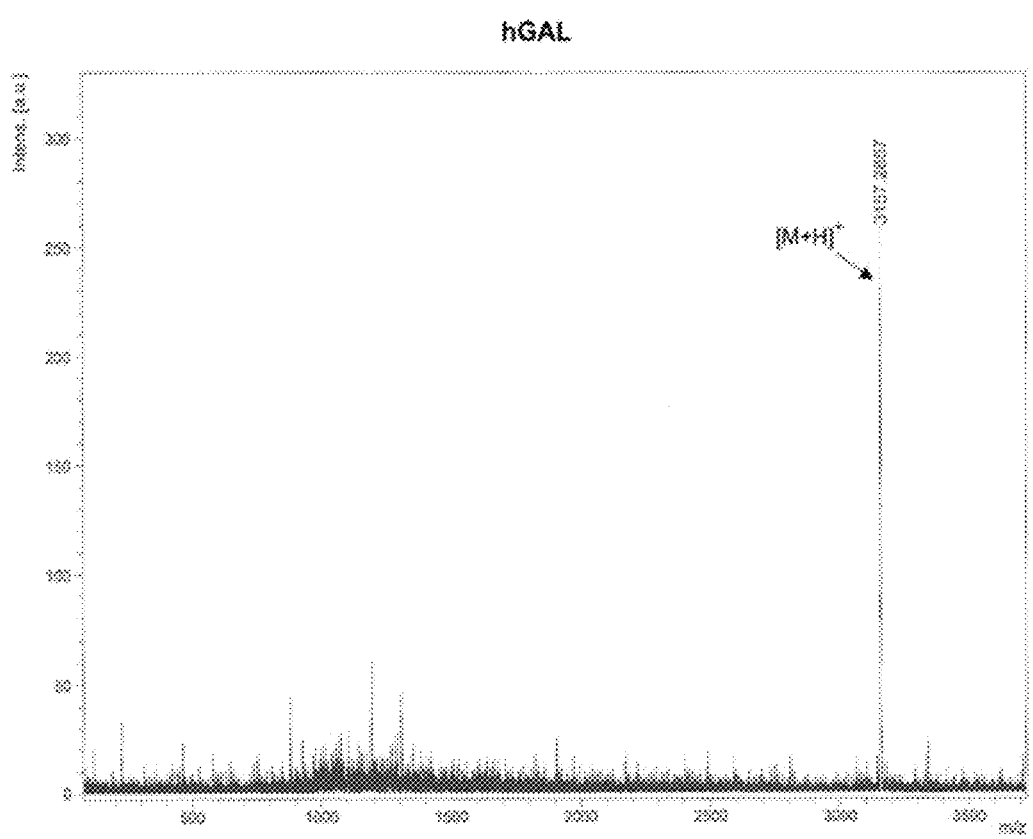
Figure 20:
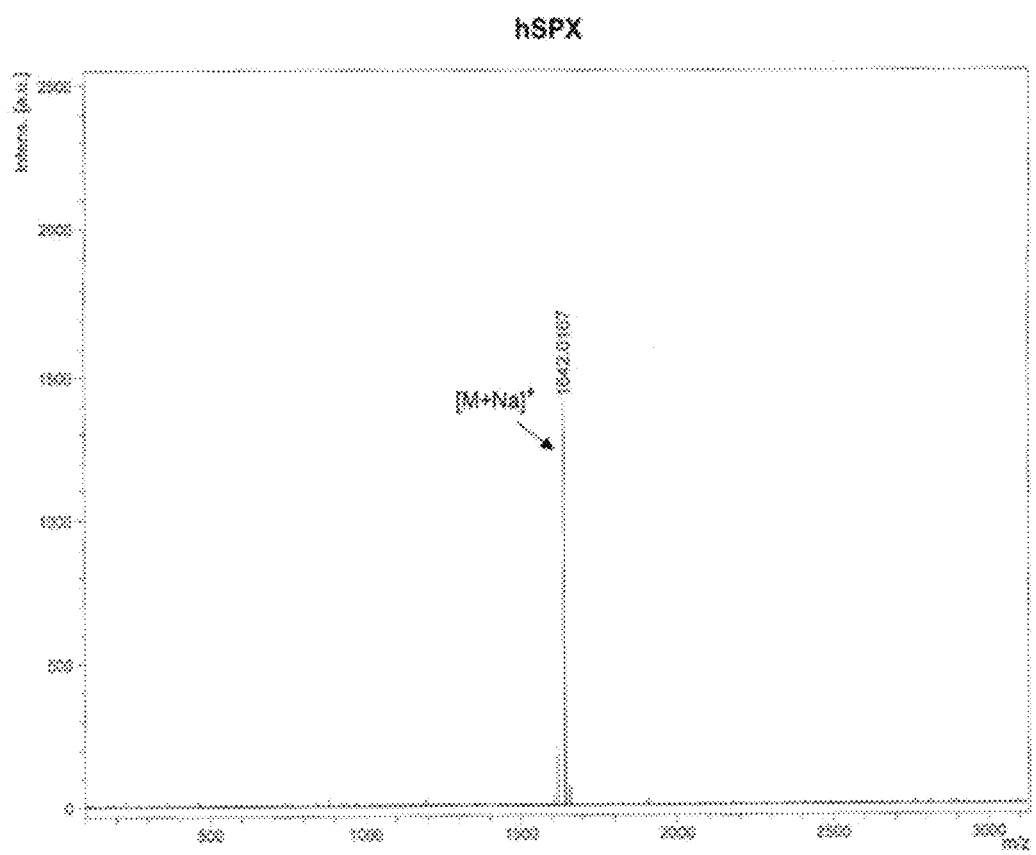

It was the aim to make a cyclic form of hSPX that did not lose bioactivity with disulfide bonding constraints. To do this, it was important to know which sites can tolerate cysteine substitutions. Cysteine-scanning mutagenesis was performed from position 1 to position 14 for hSPX. Fourteen hSPX mutants were designed and synthesized. The bioactivities of these mutants against GalR2 and GalR3 were measured by SRE-Luc assay at single dose (1 μM, 6 hours) treatment in HEK293 cells transiently transfected with GalRs and $G_{qi}$ plasmids, while hGAL and hSPX were utilized as positive controls (FIGS. 19-20). The results showed that, cysteine mutations at 1 (SEQ ID NO: 3), 4 (SEQ ID NO: 4), and 13 (SEQ ID NO: 5) had minimum effects on receptor activation of GalR2 and GalR3. For mutations at 7, 8, and 11, cysteine substitution led to mild loss of activity; while cysteine replacements at 2, 3, 5, 6, 9, 10, 12, and 14 (C2, C3, C5, C6, C9, C10, C12 and C14) severely impaired bioactivity, suggesting that these residues may have direct interactions with binding pocket upon receptor activation (FIG. 2A). The full-dose experiments confirmed that cysteine mutations at 1, 4, and 13 (C1, C4 and C13) had little effect on the potency of GalR2/GalR3, in terms of $EC_{50}$ (FIG. 2B, Table 8).

In certain embodiments, variants of SEQ ID NO: 23 or SEQ ID NO: 24 having at least 92.8% homology do not include a cysteine at any of positions 2, 3, 5, 6, 9, 10, 12, and 14.

TABLE 8

Receptor activation potency of peptide ligands toward galanin receptors.

| | | hGalR1 | | hGalR2 | | hGalR3 | |
|---|---|---|---|---|---|---|---|
| Ligand | Sequence | $EC_{50}$ (μM) | $E_{max}$[1] | $EC_{50}$ (μM) | $E_{max}$[2] | $EC_{50}$ (μM) | $E_{max}$[2] |
| hGAL | GWTLNSAGYLL GPHAVGNHRSF SDKNGLTS-$NH_2$ (SEQ ID NO: 1) | 0.72 | 1.00 | 0.094 | 0.94 | >10 | 0.68 |

TABLE 8-continued

Receptor activation potency of peptide ligands toward galanin receptors.

| | | hGalR1 | | hGalR2 | | hGalR3 | |
|---|---|---|---|---|---|---|---|
| Ligand | Sequence | $EC_{50}$ (μM) | $E_{max}$[1] | $EC_{50}$ (μM) | $E_{max}$[2] | $EC_{50}$ (μM) | $E_{max}$[2] |
| hSPX | NWTPQAMLYLK GAQ-$NH_2$ (SEQ ID NO: 2) | N.M. | N.M. | 0.22 | 1.00 | 0.45 | 1.00 |

TABLE 8-continued

Receptor activation potency of peptide ligands toward galanin receptors.

| Ligand | Sequence | hGalR1 EC$_{50}$ (μM) | E$_{max}$[1] | hGalR2 EC$_{50}$ (μM) | E$_{max}$[2] | hGalR3 EC$_{50}$ (μM) | E$_{max}$[2] |
|---|---|---|---|---|---|---|---|
| hSPX (C1) | CWTPQAMLYLK GAQ-NH$_2$ (SEQ ID NO: 3) | N.M. | N.M. | 0.51 | 1.05 | 0.36 | 1.00 |
| hSPX (C4) | NWTCQAMLYLK GAQ-NH$_2$ (SEQ ID NO: 4) | N.M. | N.M. | 0.47 | 0.98 | 0.77 | 0.91 |
| hSPX (C13) | NWTPQAMLYLK GCQ-NH$_2$ (SEQ ID NO: 5) | N.M. | N.M. | 0.37 | 0.87 | 0.63 | 0.88 |
| LH101 | CWTPQAMLYLK GCQ-NH$_2$ (SEQ ID NO: 6) | N.M. | N.M. | 1.19 | 1.09 | 1.56 | 1.04 |
| LH102 | NWTCQAMLYLK GCQ-NH$_2$ (SEQ ID NO: 7) | N.M. | N.M. | 1.43 | 1.08 | 1.50 | 0.87 |
| LH101 (Ac) | Ac-CWTPQAML YLKGCQ-NH$_2$ (SEQ ID NO: 8) | N.M. | N.M. | 0.38 | 0.97 | 0.39 | 1.00 |
| hGAL (1-16) | GWTLNSAGYLL GPHAV-NH$_2$ (SEQ ID NO: 9) | ~5.00 | 0.94 | 0.22 | 1.02 | >10 | 0.45 |
| LH201 | CWTLNSAGYLL GCHAV-NH$_2$ (SEQ ID NO: 10) | >10 | 0.35 | 0.12 | 1.00 | >10 | 0.55 |
| LH201 (Ac) | Ac-CWTLNSAG YLLGCHAV-NH$_2$ (SEQ ID NO: 11) | N.M. | 0.22 | 0.48 | 1.16 | N.M. | 0.20 |

[1]Relative to hGAL E$_{max}$;
[2]Relative to hSPX E$_{max}$;
N.M., not measurable.

Figure 21:
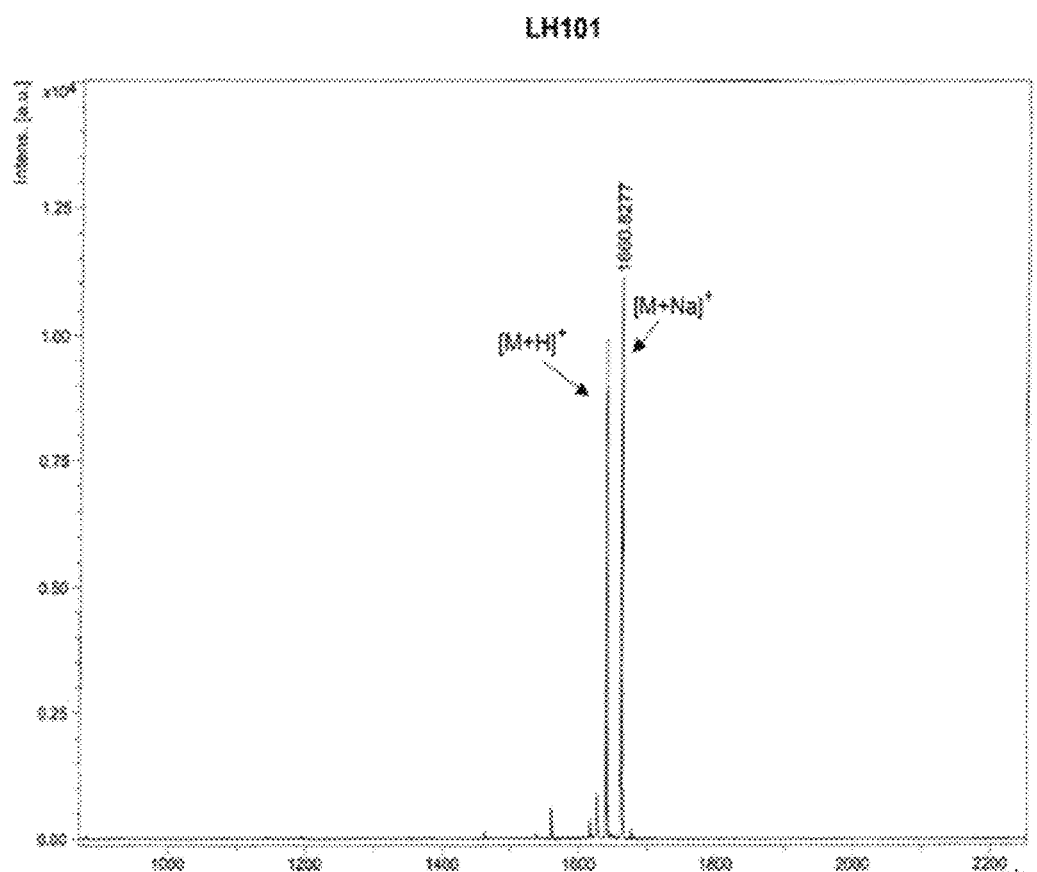
Figure 22:
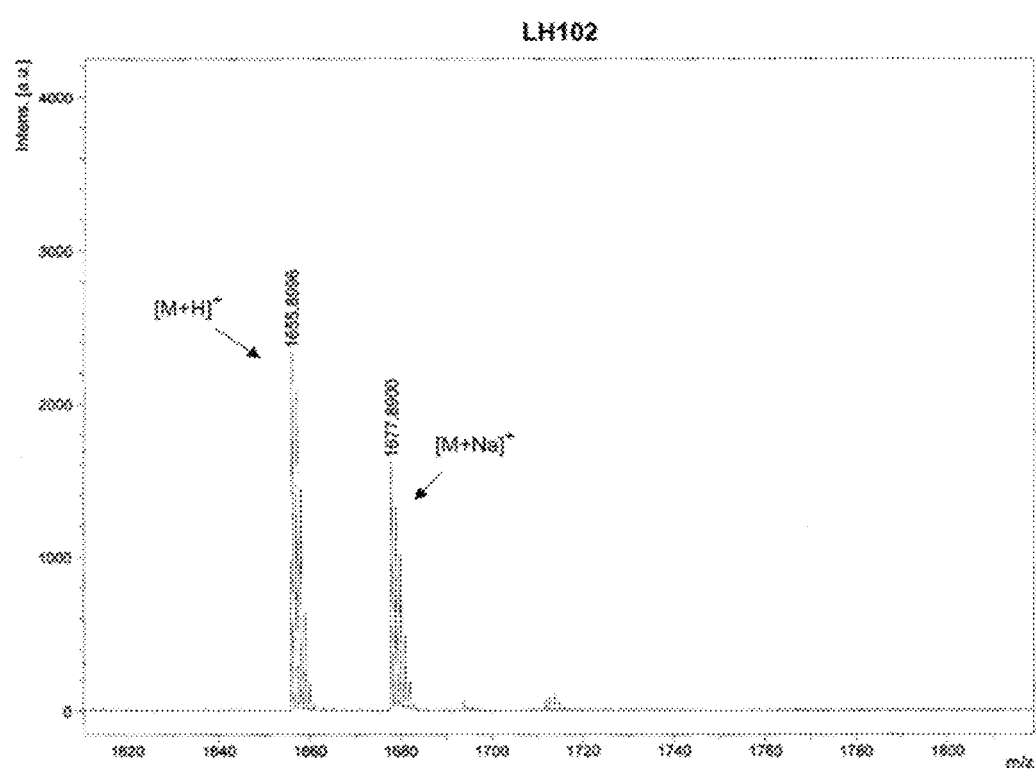
Figure 23:
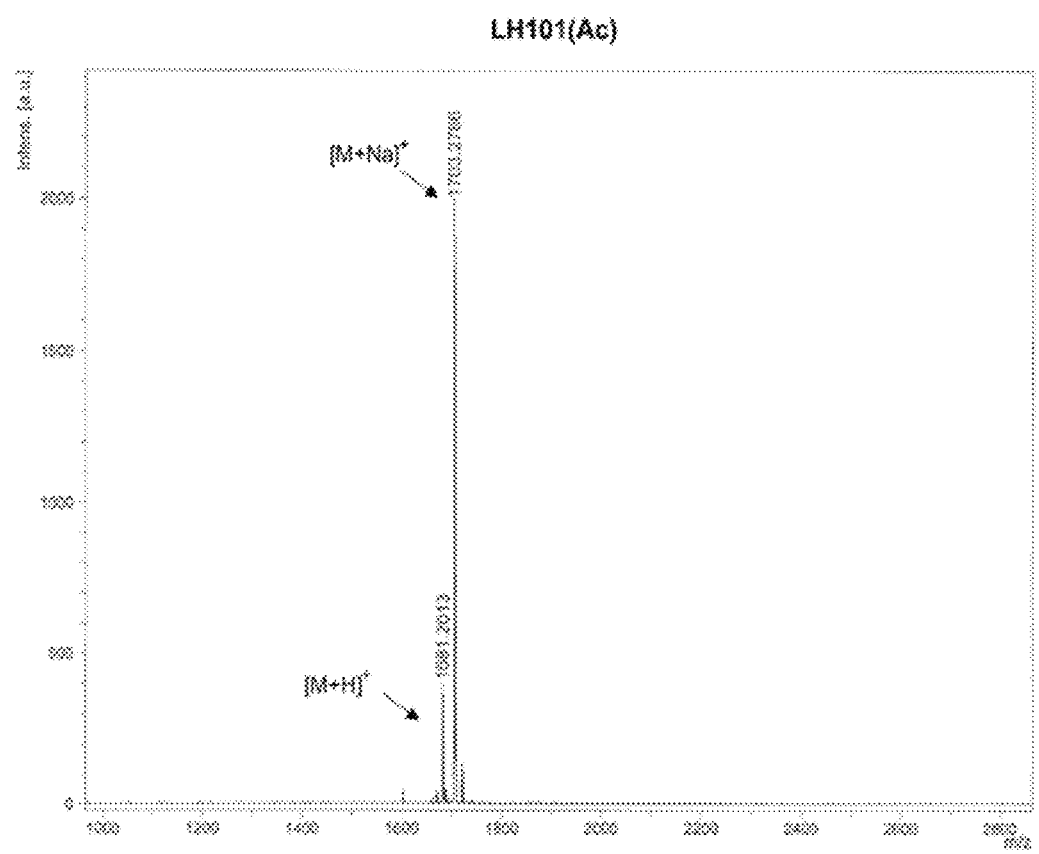

Based on the βαβ conformation suggested by MD and NMR, as well as the results of cysteine-scanning experiment, N$^1$/A$^{13}$ or P$^4$/A$^{13}$ were replaced in hSPX with cysteines and connected by disulfide bonds, resulting in two cyclic peptides: LH101 (CWTPQAMLYLKGCQ-NH$_2$ (SEQ ID NO: 6)) (FIG. 44) and LH102 (NWT CQAMLYLKGCQ-NH$_2$ (SEQ ID NO: 7)) (FIGS. 21-22 and 45), both of which were stapled by disulfide bonding (FIG. 3A). In SRE-Luc assay, the potency of LH101 (EC$_{50}$=1.19/1.56 μM) was comparable to that of hSPX (EC$_{50}$=0.22/0.45 μM) toward both GalR2 and GalR 3 (FIG. 3B, Table 8), suggesting that linking between residue 1 and 13 does not affect receptor activation. In parallel, the disulfide bonding between 4 and 13 impaired maximum activation (E$_{max}$) of LH102 on GalR3 (FIG. 3B, Table 8). LH101 was chosen for further modifications. The N-terminal acetylation form, LH101 (Ac) (FIGS. 46 and 23) restored almost full potency (EC$_{50}$=0.38/0.39 μM) on GalR2 and GalR3 (FIG. 3B, Table 8). In this regard, LH101, LH102 and LH101 (Ac) are potent, cyclic analogs of hSPX. These peptides represent the first attempt to prepare a cyclic analog of SPX with biological activity, and named "cyclic spexin analogs (CSAs)".

Thus, provided herein are peptides capable of agonizing both hGalR2 and hGalR3. In certain embodiments, the peptides provided herein have little (e.g., EC50≥5 μM or ≥10 μM) or substantially no hGalR1 agonist activity.

In other embodiments, the peptides provided herein are capable of selectively agonizing one of hGalR2 or hGalR3. In certain embodiments, the peptide provided herein is a selective agonist of hGalR2 having about 1.5×, about 2×, about 3×, about 4×, about 5×, about 6×, about 8×, about 9×, about 10×, about 20×, about 30×, about 40×, or lower EC$_{50}$ for hGalR2 than hGalR3. In certain embodiments, the peptide provided herein is a selective agonist of hGalR3 having about 1.5×, about 2×, about 3×, about 4×, about 5×, about 6×, about 8×, about 9×, about 10×, about 20×, about 30×, about 40×, or lower EC$_{50}$ for hGalR3 than hGalR2.

In certain embodiments, the peptides provided herein have little (e.g., EC50≥10 μM) or substantially no hGalR3 agonist activity.

Figure 24:
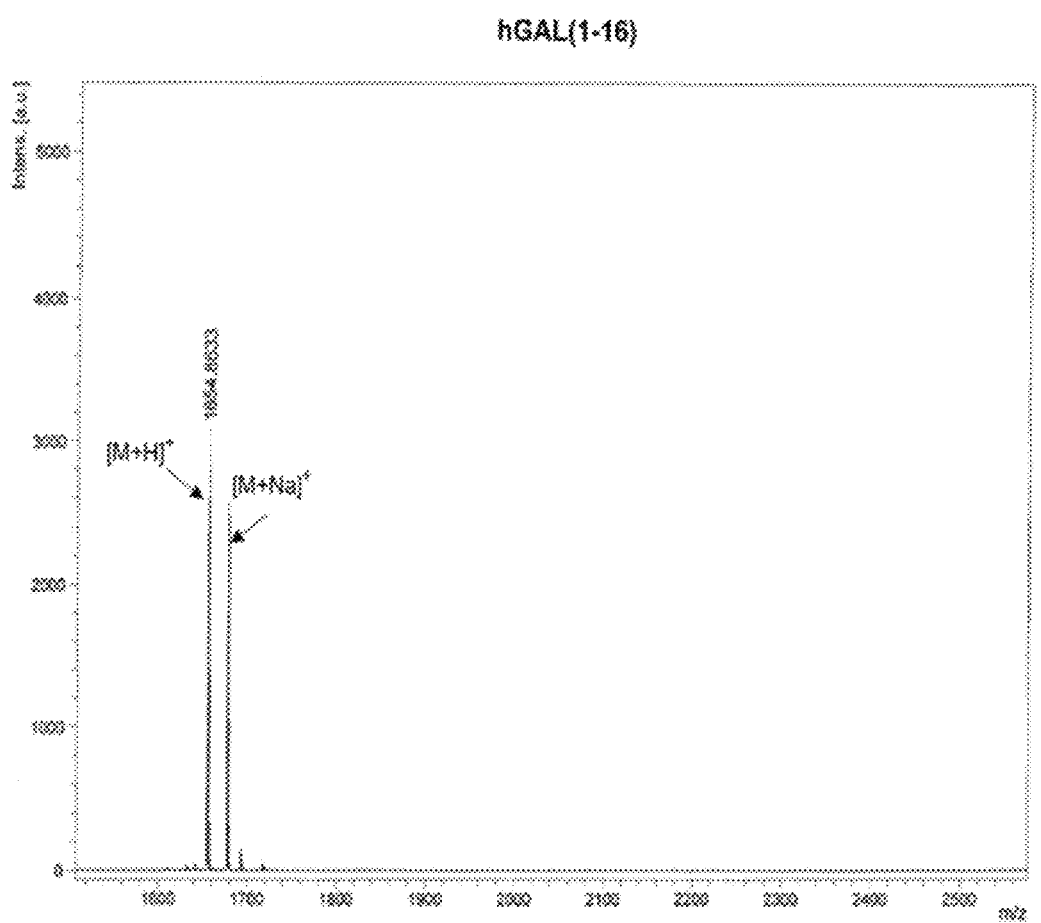
Figure 25:
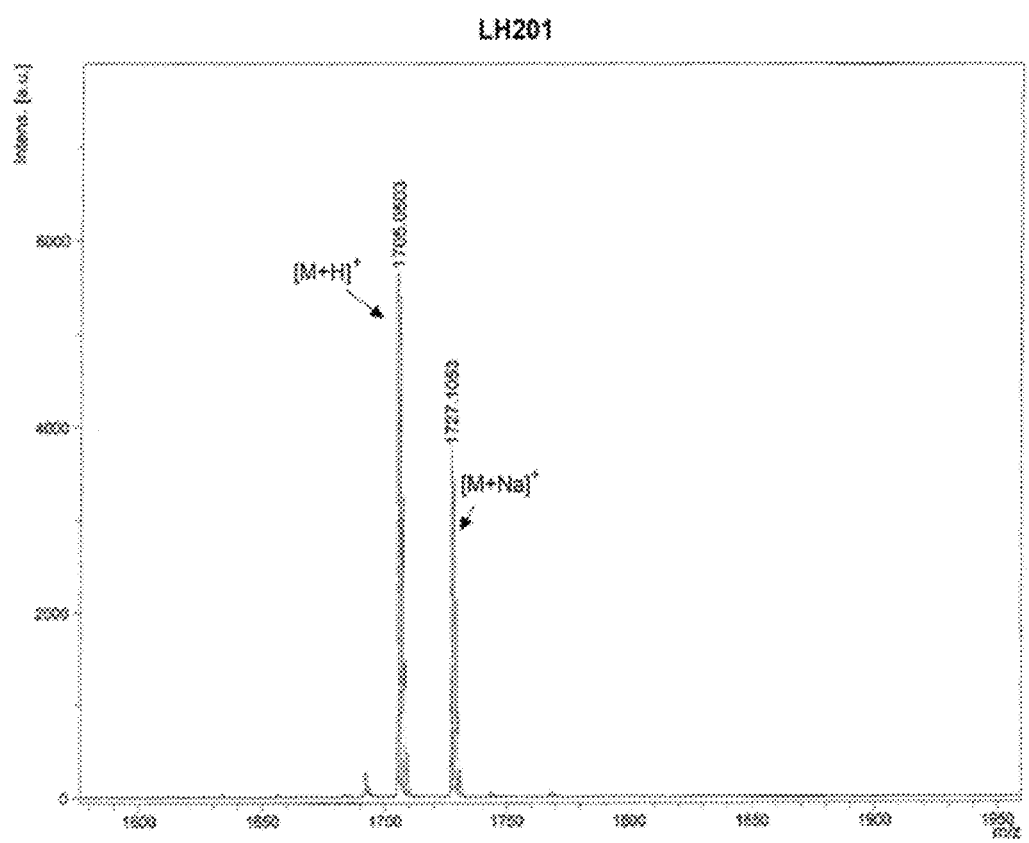
Figure 26:
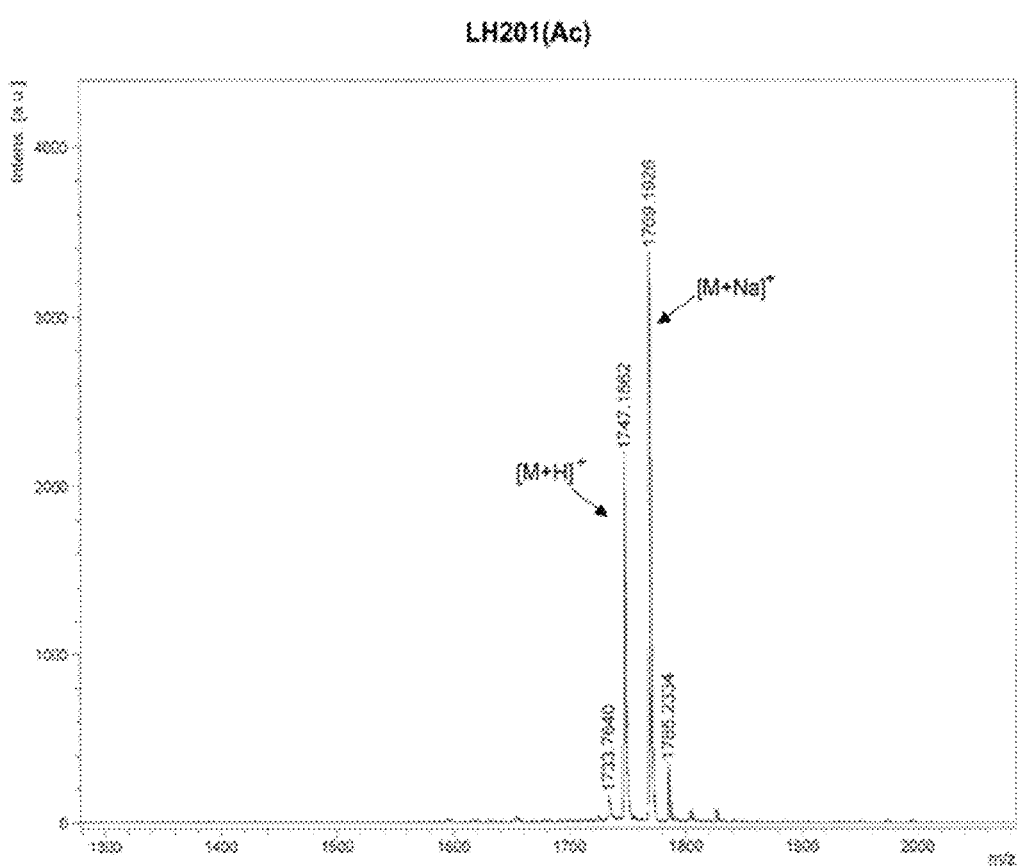
Figure 40:
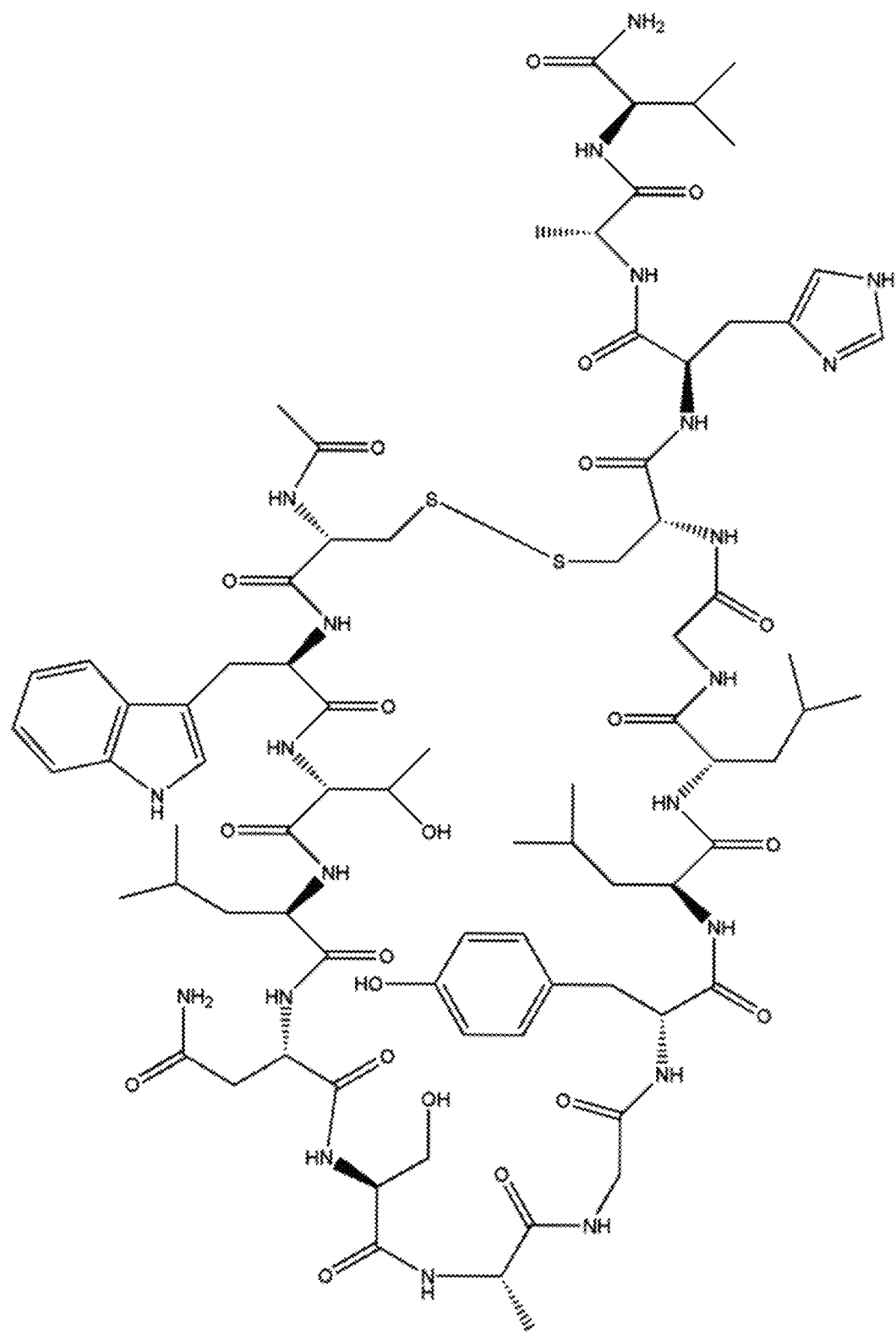

Previous studies have suggested that the hGAL N-terminal fragment, hGAL (1-16) (FIGS. 3A and 24), is similarly active to GAL receptors as full-length hGAL. LH201 ( CWTLNSAGYLLGCHAV-NH$_2$ (SEQ ID NO: 10)) (FIG. 47) was synthesized, in which G$^1$ and P$^{13}$ of hGAL (1-16) were replaced by cysteines, and a disulfide bond was made (FIGS. 3A and 25). Interestingly, LH201 was observed to be a GalR2-specific agonist and lost all activity on GalR1, but kept full activity on GalR2, and was also higher than hGAL (1-16) itself (EC$_{50}$ 0.12 μM vs 0.22 μM). LH201 was only able to activate GalR3 at high doses, but when it did, it was a little stronger than hGAL (1-16) (FIG. 3C, Table 8). In this regard, LH201 is a selective, sub-micromolar cyclic agonist of GalR2. The N-terminal acetylated form of LH201 (FIGS. 3A and 26) was also prepared. No activity toward GalR1 and GalR3 was observed with LH201 (Ac) even at very high concentration (FIG. 3C, Table 8). LH201 (Ac) (FIG. 40) activated GalR2 with EC$_{50}$=0.48 μM, which was less potent than LH201, indicating that the N-terminal acetylation may have different effects on bioactivity in cyclic analogs of hSPX and hGAL(1-16) (FIG. 3C, Table 8).

The in vitro bioactivity data suggested that the CSAs (LH101 and LH101 (Ac)), can potently activate GalR2 and GalR3, and that the same cyclic form could also be adopted by hGAL(1-16). It was interesting that in LH101 and LH101(Ac), the N- and C-terminal residues were linked by disulfide bond and close to each other—which was consistent with the hSPX βαβ conformation.

LH101(Ac) Adopts the βαβ Conformation in Water

Figure 27:
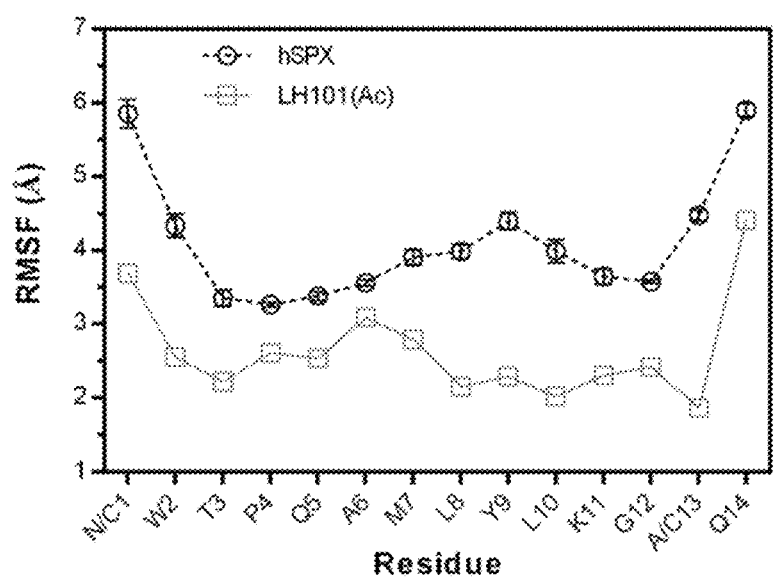
Figure 28:
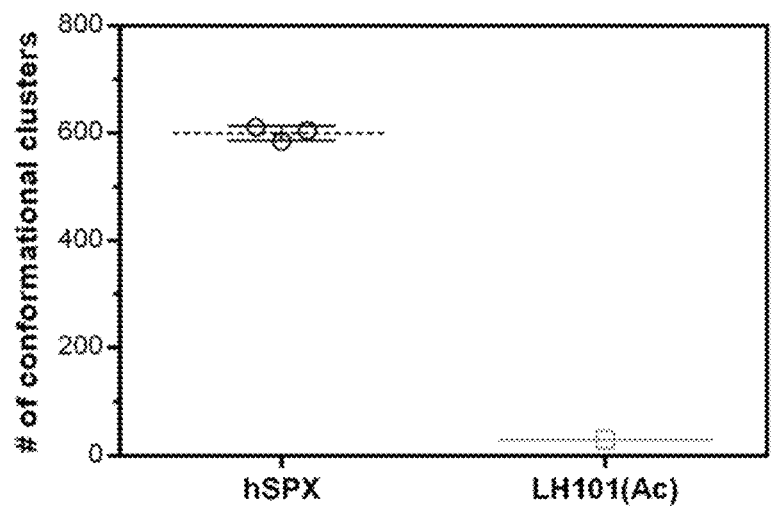
Figure 29:
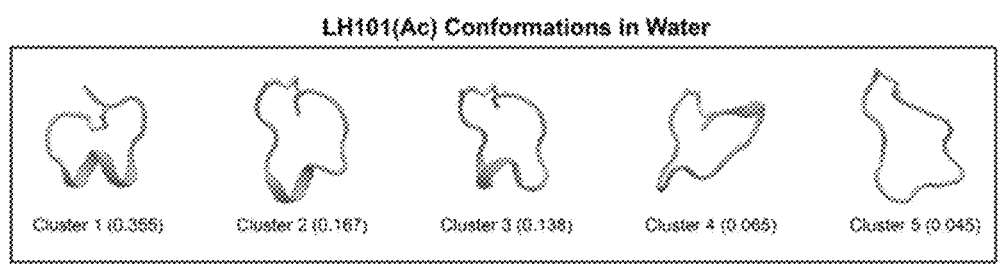

MD simulation and NMR analysis were used to elucidate the structure of LH101 (Ac) in water. The Cα atom RMSF of LH101 (Ac) in MD simulations were much reduced (FIG. 27), suggesting less flexibility of LH101 (Ac) compared with hSPX. The principal component analysis (PCA) of backbone dihedral angle also indicated that LH101 (Ac) had confined conformational space (FIG. 4A). Consistent with this observation, the number of conformational clusters of LH101 (Ac) was 30, much less than that of hSPX in water (600±14) (FIG. 28). As expected, the top ranking cluster of LH101 (Ac) was the βαβ conformation, which occupied up to 35.5% of total simulation time (FIG. 29). Meanwhile, other conformations with substantial life time could also be observed (FIG. 29).

Figure 30A:
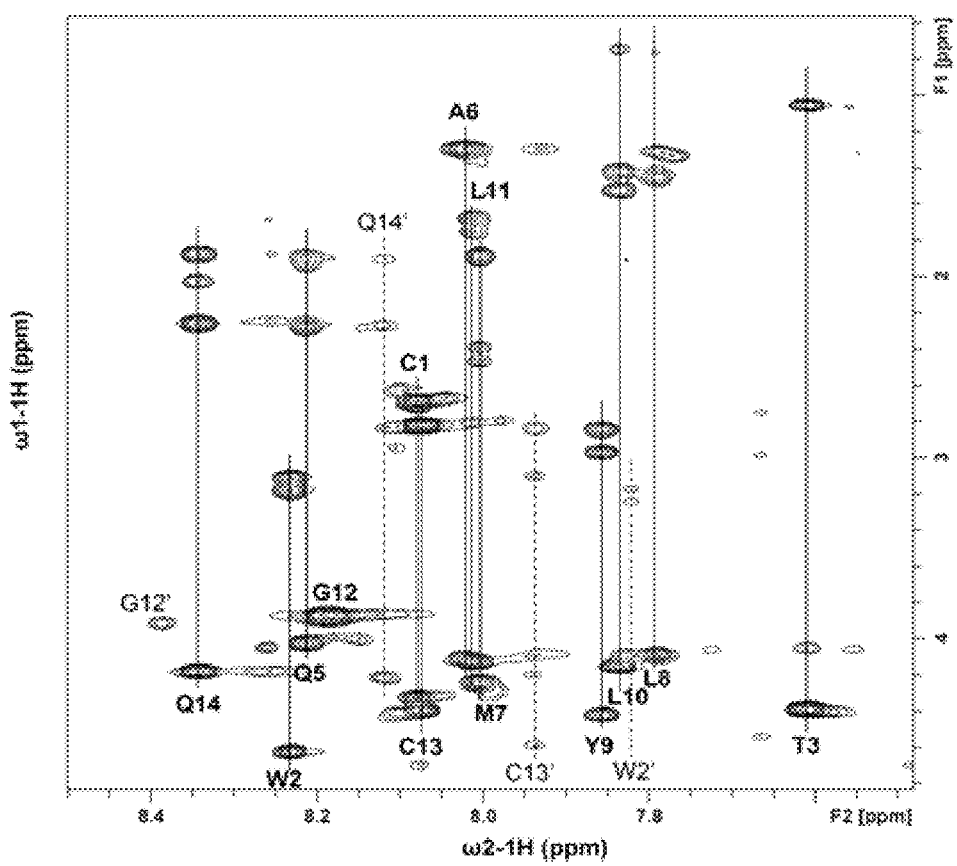
Figure 30B:
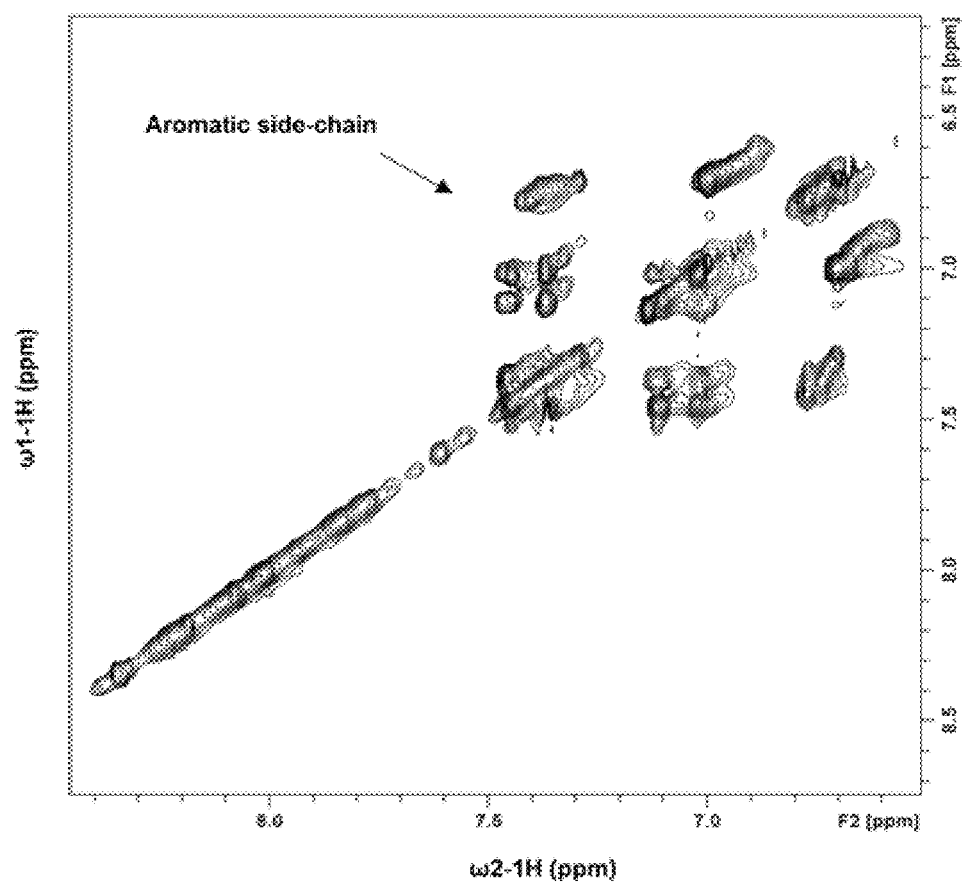
Figure 31A:
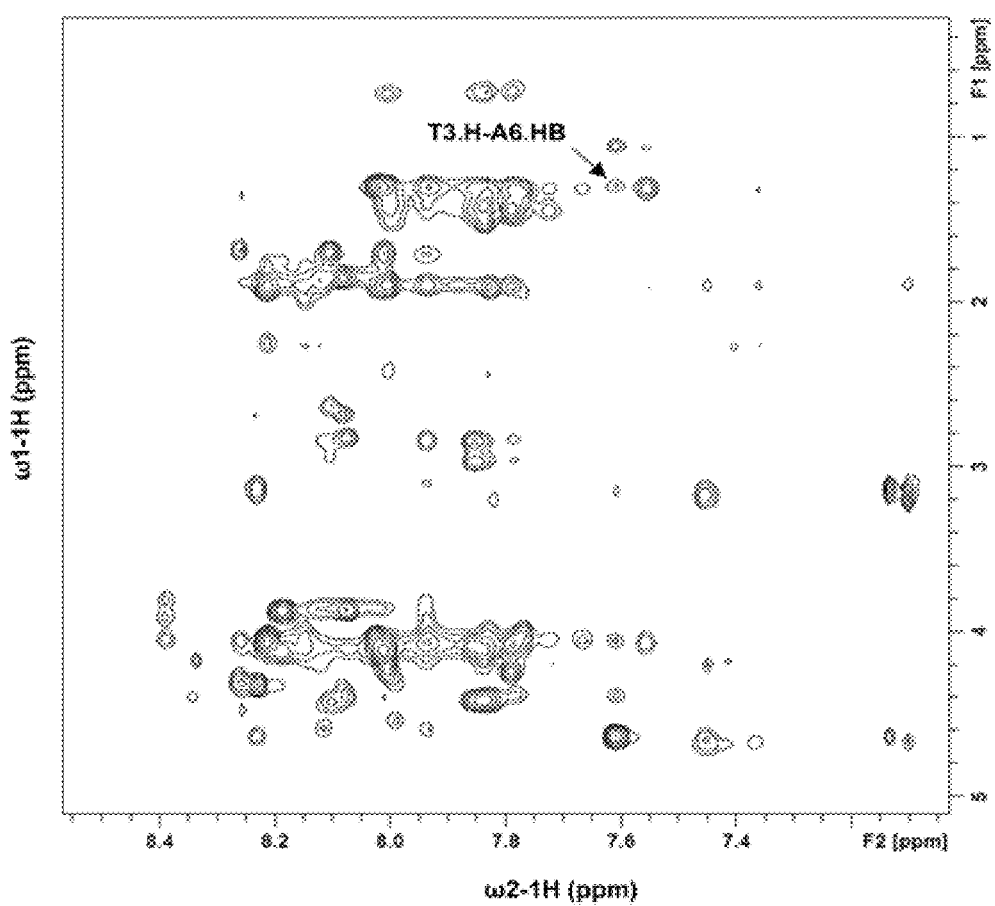
Figure 31B:
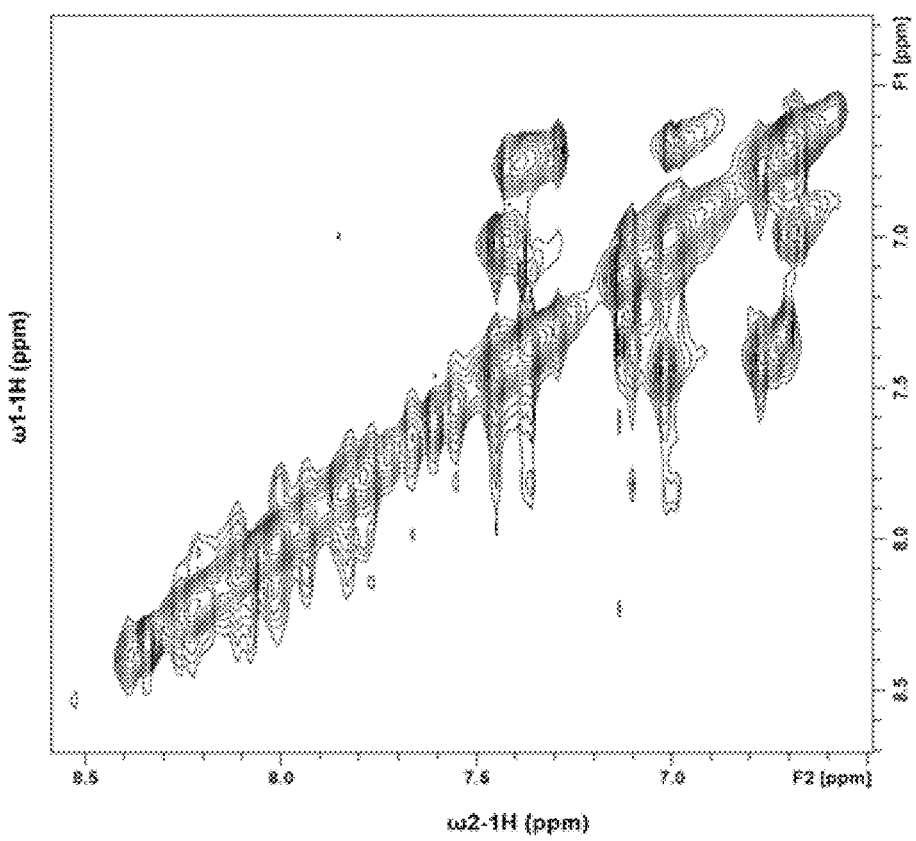

$^1$H—$^1$H 2D-TOCSY and NOESY experiments for LH101 (Ac) were conducted. Most hydrogen atom chemical shifts of all 14 residues in LH101 (Ac) could be assigned (FIGS. 30A and 30B, Table 9). For some of them, alternative chemical shifts were also identified (FIGS. 30A and 30B, Table 9), suggesting that multiple significant conformers may exist. Since the structure of LH101 (Ac) in solution cannot be directly determined, the existence of distinctive identifiable NOEs was investigated. Interestingly, as with hSPX, the NOE between $T^3.H\text{-}A^6.HB$ was indeed found (FIGS. 31A and 31B). The volume of this NOE was $3.6\times10^6$, which was close to that of $T^3.H\text{-}T^3.HG$ ($4.1\times10^6$), suggesting the distance constraint between $T^3.H$ and $A^6.HB$ was also retained in LH101(Ac). Among the top ranking conformational clusters in MD simulation, the βαβ conformation was the only one that satisfied such constraint (Table 10); it was thus inferred that LH101 (Ac) adopts the βαβ conformation in water.

TABLE 9

$^1H$ assignment and chemical shift for LH101 (Ac) in aqueous solution at 298K.

| Residue | NH | αH | βH | γH | δH | Others |
|---|---|---|---|---|---|---|
| C1 | 8.084 | 4.329 | 2.694 | | | |
| W2 | 8.238 (7.827)[1] | 4.629 (4.662) | 3.185, 3.115 (3.247, 3.178) | | 7.138 | 10.015, 7.453, 7.373, 7.113, 7.027 |
| T3 | 7.613 (7.369) | 4.394 (4.535) | 4.056 (4.225) | 1.058 (0.968) | | |
| P4 | | 4.077 | 2.193 | 1.913, 1.759 | 3.535, 3.493 | |
| Q5 | 8.219 | 4.031 | 1.902 | 2.285 | | |
| A6 | 8.028 | 4.102 | 1.298 | | | |
| M7 | 8.009 | 4.249 | 1.894 | 2.472, 2.396 | | |
| L8 | 7.796 | 4.092 | 1.458 | 1.321 | 0.768, 0.710 | |
| Y9 | 7.862 | 4.425 | 2.973, 2.847 | | | HD*, 6.999 HE*, 6.704 |
| L10 | 7.841 | 4.157 | 1.531, 1.424 | 1.313 | 0.749 | |
| K11 | 8.018 | 4.136 | 1.756, 1.684 | 1.338 | 1.567 | EH, 2.875 ζNH$_3^+$, 7.436 |
| G12 | 8.188 (8.393) | 3.875 (3.918) | | | | |
| C13 | 8.080 (7.943) | 4.400 (4.593) | 2.826 (3.105, 2.843) | | | |
| Q14 | 8.349 (8.125) | 4.186 (4.222) | 2.033, 1.880 (2.031, 1.909) | 2.266 (2.275) | | |

[1]The number in bracket represented the minor chemical shifts of that residue in $^1H$ assignment.

TABLE 10

The distances between $T^3.H$ and $A^6.HB$ in representative conformation for top 5 conformational clusters of LH101 in water during MD simulations.

| Conformational cluster | $T^3.H\text{-}A^6.HB$ distance (Å) #1 |
|---|---|
| Top 1 | 4.16, 4.51, 5.41 |
| Top 2 | 9.66, 10.89, 11.07 |
| Top 3 | 7.04, 7.10, 7.54 |
| Top 4 | 7.08, 7.53, 8.24 |
| Top 5 | 11.92, 12.61, 13.05 |

Figure 32:
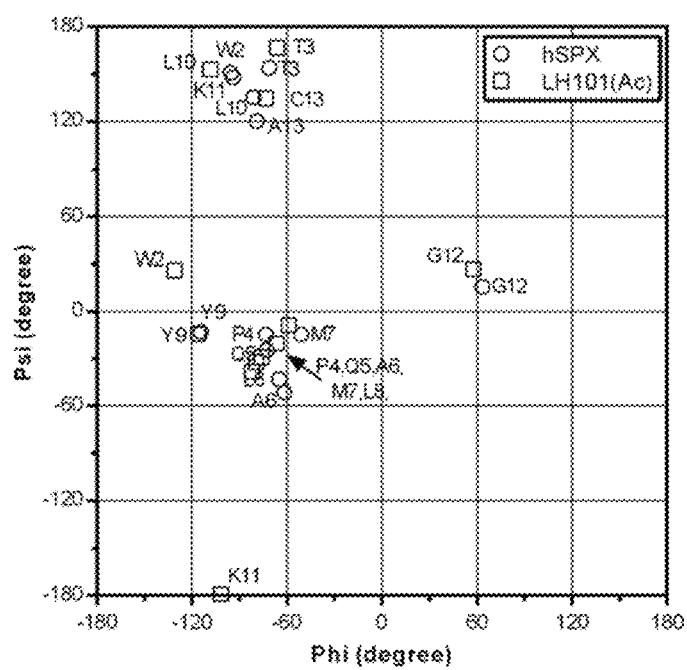
Figure 33:
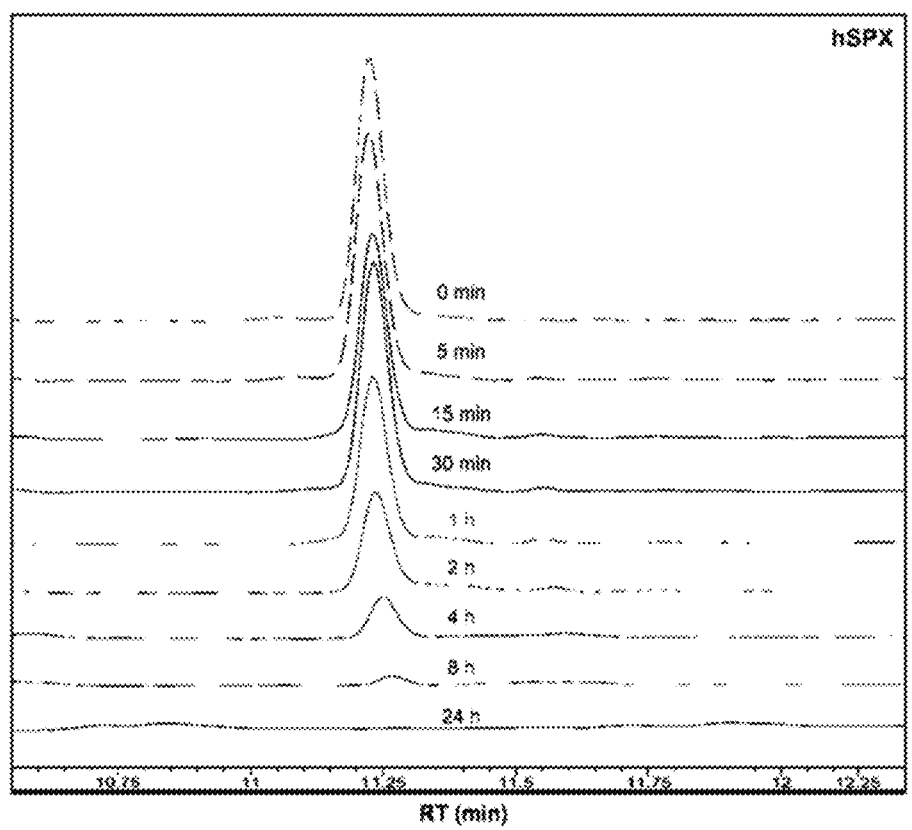
Figure 34:
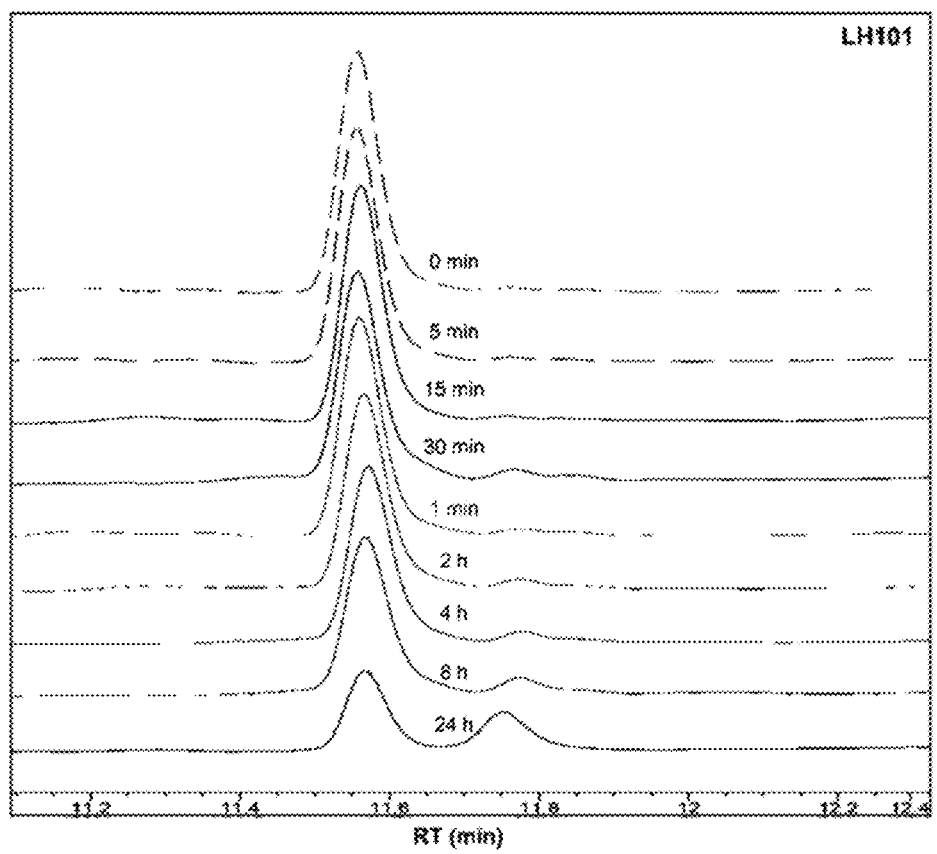
Figure 35:
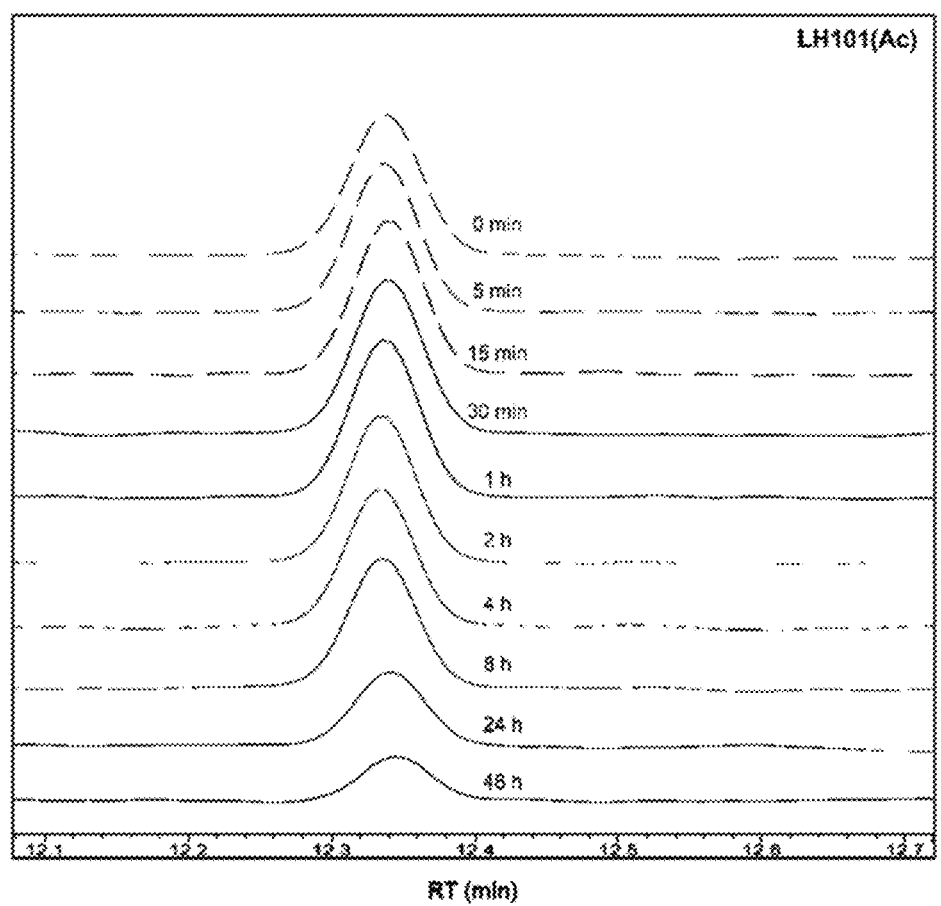
Figure 36:
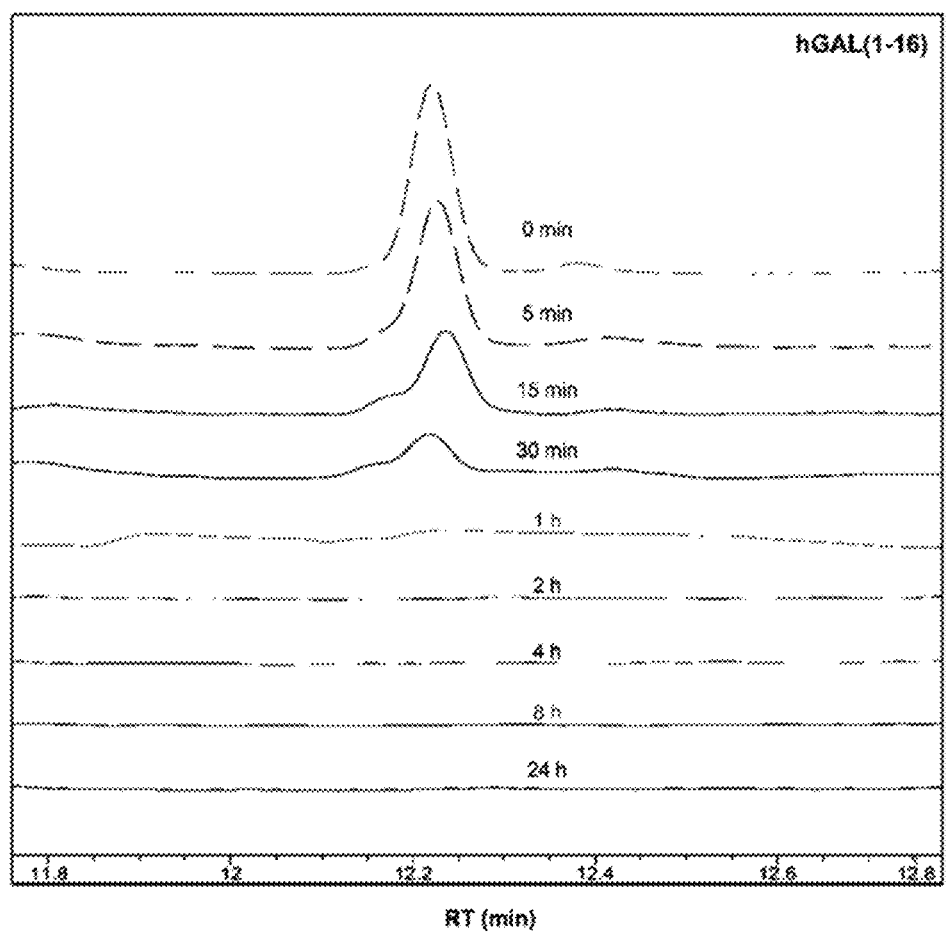
Figure 37:
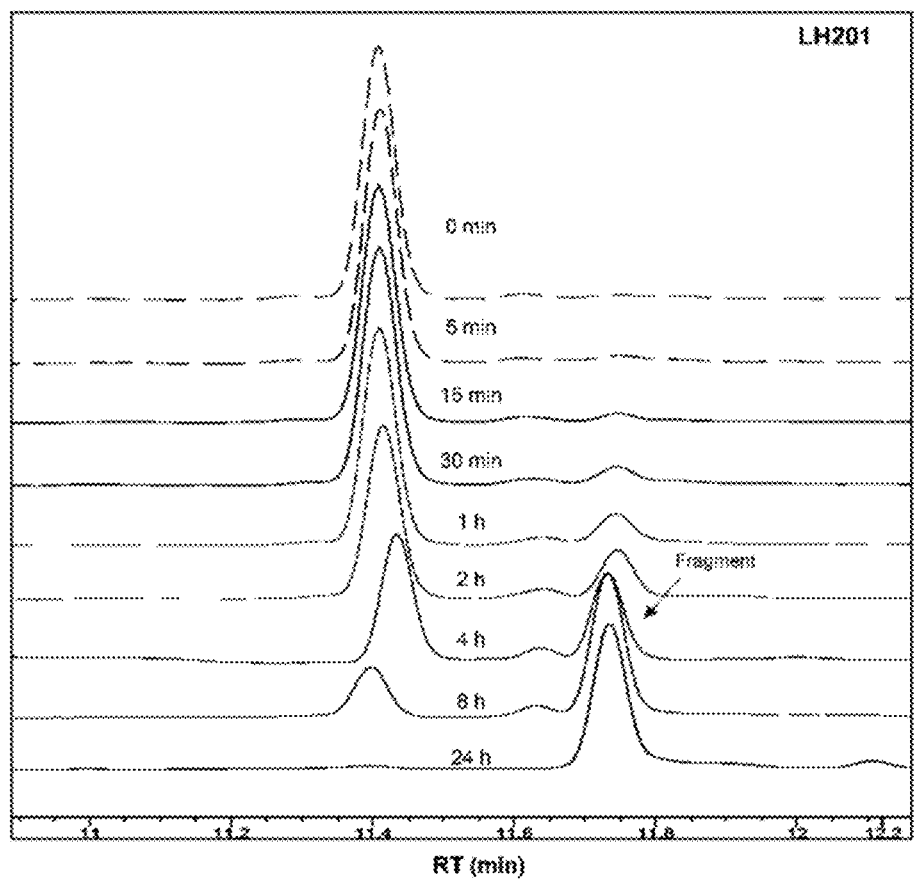
Figure 38:
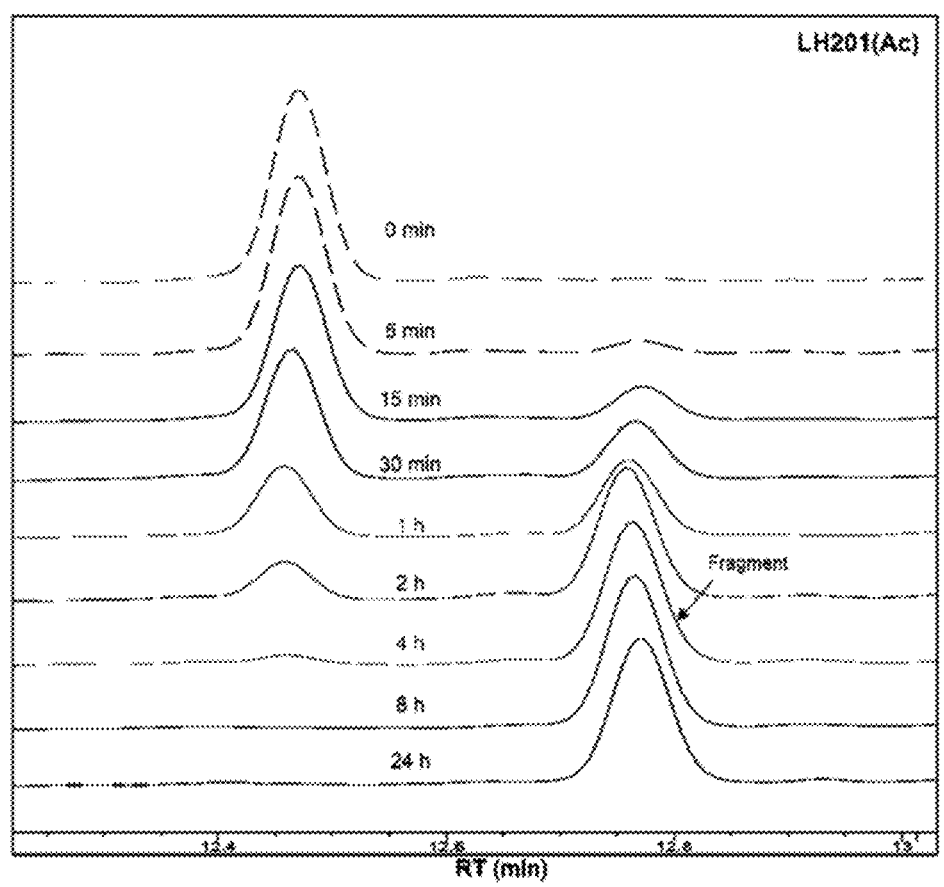

The key structural features of hSPX βαβ conformation, including the two β turns characterized by backbone hydrogen bonds $T^3.O\text{-}A^6.H$ and $A^6.O\text{—}Y^9.H$, were well preserved in LH101(Ac) (FIG. 4B). The conformations of hSPX and LH101 (Ac) were found to be highly similar, with 1.40 Å main-chain atom RMSD between them (Table 11). The backbone dihedral angle analysis also supported the existence of a short, nascent helix from $P^4$ to $L^8$ (FIG. 32, Table 12). The disulfide bond between $C^1$ and $C^{13}$ in LH101 (Ac) seemed to well mimic the hydrophobic packing between $W^2$ and $L^{10}$ in hSPX (FIG. 4B). One structural difference between LH101 (Ac) and hSPX was the position of the $W^2$ side-chain; in LH101 (Ac) it was 'outward' while in hSPX it was 'inward' (FIG. 4B). The biological consequences of such change requires further investigation. It is possible that this change moderately weakens the receptor interaction, masking the gain from stabilization of the βαβ conformation by the disulfide bond.

TABLE 11

The main-chain atom RMSD between hSPX βαβ conformation (MD + NMR) and LH101 (Ac) βαβ conformation (MD + NMR).

| Residue | RMSD (Å) |
|---|---|
| N1/C1[1] | 4.05 |
| W2 | 1.30 |
| T3 | 0.46 |
| P4 | 0.65 |
| Q5 | 0.65 |
| A6 | 0.31 |
| M7 | 0.62 |
| L8 | 0.38 |
| Y9 | 0.58 |
| L10 | 0.28 |
| K11 | 0.84 |
| G12 | 1.01 |
| A13/C13[2] | 1.55 |
| Q14 | 1.78 |
| Overall | 1.40 |

[1]The 1$^{st}$ residue in hSPX is Asn, while it is Cys in LH101 (Ac).
[2]The 13$^{th}$ residue in hSPX is Ala, while it is Cys in LH101 (Ac).

TABLE 12

The backbone dihedrals of hSPX and LH101 (Ac) βαβ conformation.

| | hSPX | | LH101 (Ac) | |
|---|---|---|---|---|
| Residue | Phi (degree) | Psi (degree) | Phi (degree) | Psi (degree) |
| W2 | −95.6 | 151.0 | −131.2 | 26.2 |
| T3 | −71.3 | 153.9 | −73.6 | 134.6 |
| P4 | −73.3 | −14.7 | −66.7 | −20.6 |
| Q5 | −72.6 | −24.7 | −76.2 | −29.3 |
| A6 | −61.8 | −51.7 | −79.5 | −32.4 |
| M7 | −51.0 | −14.7 | −59.0 | −8.7 |
| L8 | −64.9 | −43.2 | −82.1 | −38.5 |
| Y9 | −114.6 | −13.0 | −116.0 | −14.2 |
| L10 | −81.2 | 135.4 | −108.4 | 152.8 |
| K11 | −94.0 | 147.8 | −101.8 | −179.0 |
| G12 | 63.3 | 15.7 | 57.8 | 26.9 |
| A13/C13[1] | −79.1 | 120.2 | −66.2 | 166.7 |

[1]The 13$^{th}$ residue in hSPX is Ala, while it is Cys in LH101 (Ac).

The folding trajectory suggests that LH101 (Ac) rarely adopts the α-helix conformation in water (FIGS. 4C and 4D). The folding kinetics of LH101 (Ac) βαβ conformer was also analyzed and compared with hSPX. Both the folding rate and life time were much increased in LH101 (Ac) (FIG. 4E). The maximum life time of βαβ conformation in LH101 (Ac) even exceeded one microsecond (FIG. 4E), indicating that in LH101 (Ac) the βαβ conformation is significantly reinforced. Without wishing to be bound by theory, it was thus inferred from this finding and the bioactivity data that the βαβ is the most likely biological active conformer recognized by GalR2 and GalR3.

Improved Serum Stability of the Cyclic Analogs of hSPX

The serum stability of CSAs was tested using an in vitro assay followed by reverse-phase high-performance liquid chromatography (RP-HPLC) analysis (FIGS. 33-38).

Figure 39A:
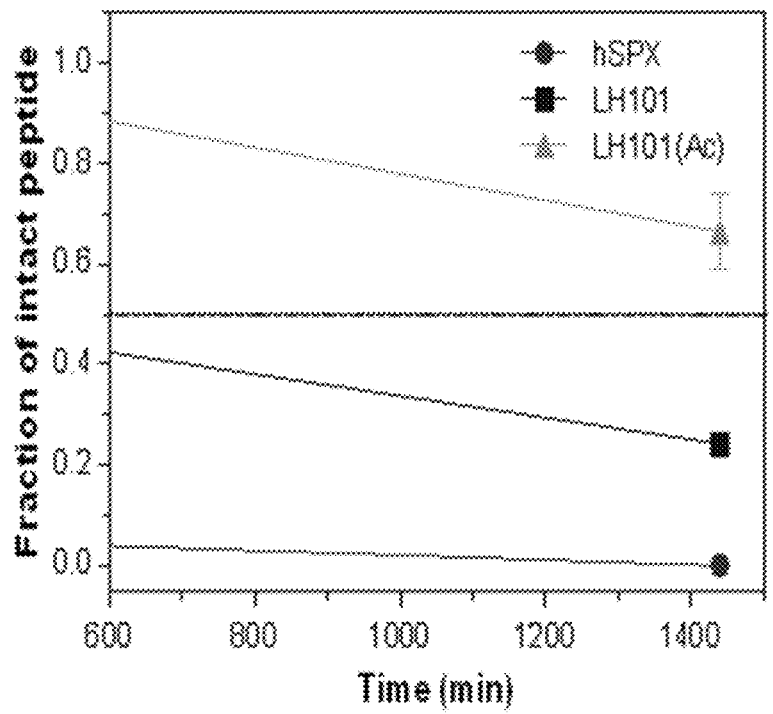
Figure 39B:
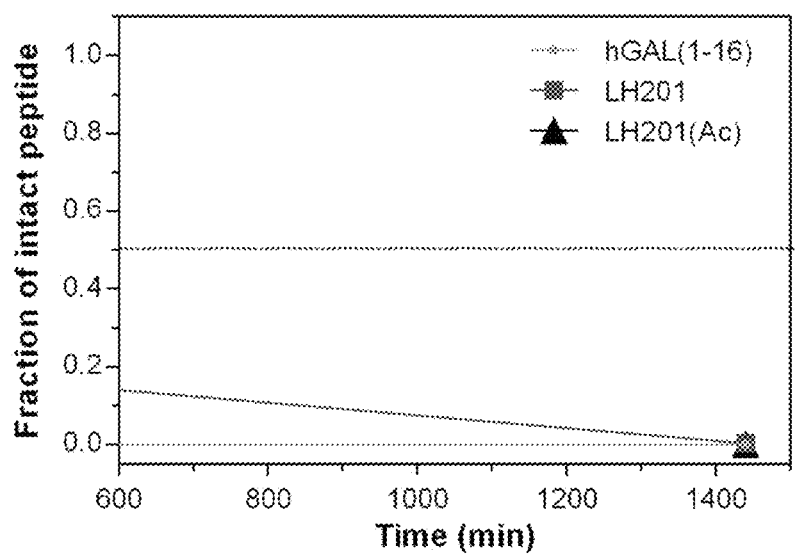

The intact peptides of hSPX degraded quickly in serum ($t_{1/2}$=66.5 min), and almost vanished after 8 h incubation (FIGS. 5A and 39). LH101 was relatively stable in serum ($t_{1/2}$=355.7 min, 5.3-fold enhancement), and 46% of intact peptide of LH101 could be detected even after 8 h incubation (FIGS. 5A and 39). Surprisingly, the acetylation of LH101 led to dramatic enhancement of serum stability. LH101 (Ac) was extremely stable at the first 8 hours incubation (FIG. 5A). The half-life time of LH101 (Ac) was greater than 1 day ($t_{1/2}$=1973.7 min)—a significant 29.1-fold enhancement compared with hSPX (FIGS. 5A and 39). Consistently, the cyclic analog, LH201 ($t_{1/2}$=169.4 min), was also more stable than its wildtype counterpart human galanin (1-16) ($t_{1/2}$=14.1 min) (FIG. 5B). However, LH201 (Ac) ($t_{1/2}$=51.9 min) was less stable than LH201, but still more stable than hGAL (1-16) (FIG. 5B).

LH101 Suppressed Body Weight Gain in High-Fat-Diet Induced Obesity Mice

Previous studies suggested that down-regulation of spexin was associated with several disorders, such as obesity, type-II diabetes, nonalcoholic fatty liver disease, and constipation. To demonstrate the therapeutic value of this hSPX cyclic analog, the effect of LH101 on body weight gain in male mice (C57BL/6J) with diet-induced obesity (DIO) was investigated.

Male mice (C57BL/6J) weighing about 22-25 g were purchased from the Laboratory Animal Services Center, The Chinese University of Hong Kong, Hong Kong. The animals were fed with a high fat diet (Research Diets, New Brunswick, N.J.) ad libitum with free access to water and were housed in rooms maintained at 22±1° C. with a 12 h light/dark cycle (lights on 6:00-18:00). Animals were constantly acclimated to the facility until the body weight reached 45-50 g. Then all the diet induced obese mice were divided into 2 groups randomly for the drug treatment. The Animal Ethics Committees of Hong Kong Baptist University, approved all experimental protocols, in accordance with "Institutional Guidelines and Animal Ordinance" from Department of Health, Hong Kong Special Administrative Region.

In the result, LH101 at 25 µg/kg by intraperitoneal injection (i.p.) suppressed mice body weight gain over the course of 14-days-treatment while controls receiving PBS continued to gain weight on the high fat diet (FIG. 43), suggesting that LH101 maintains the biological functions of spexin in vivo.

LH101(Ac) Demonstrated Better Body Weight Control Efficacy than hSPX

Previous studies have suggested that down-regulation of SPX is associated with several disorders, including obesity. To demonstrate the potential therapeutic value of CSAs, the effect of LH101 (Ac) on body weight gain in C57BL/6J mice with high-fat-diet (HFD) induced obesity was tested.

Female and male C57BL/6J mice weighing 22-25 g were purchased from the Laboratory Animal Services Center, The Chinese University of Hong Kong, Hong Kong. The animals were fed with rodent diet with 60 kcal % fat (Research Diets, New Brunswick, N.J.) ad libitum with free access to water and were housed in rooms maintained at 22±1° C. with a 12 h light/dark cycle (lights on 6:00-18:00). Animals were constantly acclimated to the facility until the body weight reached no less than 30 g. Then all the diet-induced obese mice were divided into 3 groups randomly for the drug treatment. Mice body weight was daily monitored, and the food intake amount was recorded every 3 days. The Animal Ethics Committee of Hong Kong Baptist University approved all experimental protocols in accordance with "Institutional Guidelines and Animal Ordinance" from Department of Health, Hong Kong Special Administrative Region.

During an 18 day treatment study, LH101 (Ac) at 25 µg/kg by i.p. injection significantly suppressed body weight gain compared with negative controls, which received phosphate-buffered saline (PBS) (FIG. 6A) injection. The body weight control efficacy of LH101 (Ac) was comparable to that of the positive controls receiving hSPX treatment (FIG. 6A), suggesting that LH101 (Ac) retained the biological function of hSPX in vivo. It is worth noting that the weight gain of the LH101(Ac) group started to wane after 8 days, while in the hSPX group weight gain only started decreasing after 10 days (FIG. 6A), indicating potential better body weight control efficacy of LH101(Ac) than hSPX. The area-under-curve (AUC) analysis also supports the conclusion that LH101 (Ac) and hSPX exhibit significant body weight control efficacy (FIG. 6B). The anti-obesity effect induced by hSPX and LH101 (Ac) may be partially caused by the inhibitory effects on food consumption (FIG. 6C).

Since it was discovered three decades ago, the solution structures of GAL have drawn substantial research interest. Initially, the solution structure of rat GAL (identical to hGAL in the first 15 amino acids) was demonstrated to be primarily helical in TFE and disordered in water. However, CD and NMR detected a nascent helix spanning from $Thr^3$ to $Leu^{11}$ in hGAL, in aqueous solution and the first 12 amino acids of GAL kept helical conformation in the chimeric peptide transportan, in neutral phospholipid bicelles. Furthermore, Gly1 was thought to be crucial to stabilize the N-terminal helix of GAL, which was in turn believed to be important to the activation of GalR1. The α-helix conformation of GAL was thought to be biologically active, being recognized by GalRs, at least for GalR1. In the proposed complex model by Kask et al., GAL made interactions with GalR1 via the N-terminal fragment in α-helix conformation. In line with all these observations, the α-helix conformation was also observed in gSPX in 60% TFE solution, suggesting that the helical structure of gSPX can be formed in close proximity to plasma membrane of target cells. This α-conformation has been a well-established model to explain ligand-GalR recognition, used for years. In line with the observation in galanin, the α-helix conformation of goldfish spexin was observed in 60% TFE solution. However, in the present invention, MD simulations suggested an unexpected low-energy conformation of hSPX in aqueous solution, β-hairpin, which was not observed in NMR study of goldfish spexin. If the β conformer were true, hSPX could have two distinct low-energy conformations, but how is hSPX recognized by its cognate receptors?

Proposed herein is a new βαβ conformation of hSPX in the recognition of GalR2 and GalR3, which is supported by a combination of computational simulation, biophysical, and molecular biology studies. Moreover, the results of cyclic analogs of hGAL (1-16) suggest that they are also applicable to other GAL family members, such as hGAL, in activation of GalR2 and GalR3.

By using cysteine-scanning, three sites (1, 4, 13) were identified as candidate sites for incorporation of cysteine residues and disulfide formation. Cyclic peptide LH101 (CWTPQAMLYLKGCQ-NH$_2$ (SEQ ID NO: 6)), wherein a disulfide bond is present between C1 and C13, was demonstrated to be a potent activator of both hGalR2 and hGalR3. The results described herein support the hypothesis that hSPX activates cognate receptors via a possible β conformation. The results of the cyclic analog of human galanin (1-16) support the conclusion that human galanin (1-16) may activate GalR2 and GalR3 by utilizing a similar β conformation as hSPX.

With a hydrophobic core in the middle, the βαβ conformer may be inserted into the receptor binding cavity, leaving both N- and C-terminals pointing to the extracellular space. In this binding orientation, it is expected that modifications to the N- and C-terminus could yield analogs with similar properties. This proposed binding mode may explain why chemical modifications with large functional groups on the SPX N-terminal does not affect its binding to GalR2/GalR3. It may also explain why the galanin-like peptide (GALP)—a neuropeptide containing 60 amino acids with large flanking extensions at both N- and C-terminals compared with GAL—has preferential binding affinity to GalR2.

The βαβ model can be used to design a new generation of GalR agonists/antagonists. Provided herein is a novel class of GalR2 and GalR3 agonists, e.g., the cyclic spexin analogs (CSAs). The CSAs exhibit sub-micromolar bioactivity, superior serum stability, and improved anti-obesity efficacy. Peptide-based therapeutics oftentimes suffer from poor stability and/or bioavailability. However, exhibit improved stability and bioavailability.

Cyclic peptides containing a disulfide bond, e.g., LH101, LH102, and LH101 (Ac) as analogs of hSPX, and LH201 and LH201 (Ac) as analog of human galanin (1-16) have been discovered. Compared with wild type hSPX, the concentration of one agonist to induce 50% maximum activation of its receptor ($EC_{50}$) of LH101 was slightly increased, but can be recovered by N-terminal acetylation (in the case of LH101(Ac)). For LH201, the EC50 on hGalR2 was indeed better than human galanin (1-16). Another advantage of cyclic peptides is better serum stability. LH101 and LH101 (Ac) were both more stable in serum than hSPX. Given these advantages, LH101, LH102, LH101 (Ac), LH201 and LH201 (Ac) can be further developed as intravenous administration pharmaceuticals, like the pioneering works on somatostatin. It is also possible that orally administrated spexin or galanin analogs could be designed based on LH101, LH102, LH101 (Ac), LH201 and LH201 (Ac) scaffolds.

The galanin receptors (GalR1, GalR2 and GalR3) are close to somatostain receptors (SSTR1, SSTR2, SSTR3, SSTR4 and SSTR5) in polygenetic tree, and both of them belong to the γ-subfamily of GPCR. It seemed to be naturally that these receptors recognize their cognate ligands in a similar way.

The present disclosure also paves the way to clinical application of spexin or galanin signaling modulators. With good bioactivity and plasma stability, cyclic peptides LH101, LH102, LH101 (Ac), LH201 and LH201 (Ac) have potential to be applied in the treatment of GalR2 and GalR3-related diseases. LH101, LH102, and LH101(Ac) can be regarded as hSPX analogs with prolonged action, and can be used in treatment of a number of human disorders with spexin-deficiency, such as obesity, type-II diabetes, nonalcoholic fatty liver disease, constipation, and other diseases related with cardiovascular and renal function, nociception, reproduction. In particular, spexin was the most down-regulated gene in obese human fat, and spexin treatment reduced caloric intake with weight loss in rats. The data provided herein demonstrates that LH101 does inhibit body weight gain in high-fat-diet induced obesity mice, which supports the therapeutic value of LH101.

MD Simulations

Initial structure in fully extended conformation was generated by cpptraj within AMBER 14. It was solvated into a cubic box containing TIP3P water or water-TFE mixture (percentage of TFE are 0% and 50%, respectively) with buffer distance 12 Å. Charge was neutralized by counter ions. An AMBERff99SB force field was used for protein parameterization, while parameters for TFE were adopted from published work. Prepared systems were minimized and equilibrated by sander via three stages: (1) heating from 100 K to 300 K in 20 ps; (2) adjusting solvent density in 80 ps with constant pressure and constant temperature (NPT); (3) further equilibrating in 2,000 ps with NPT. Finally, all-atoms, unbiased, 10-μs, constant volume and constant temperature (NVT) simulations were performed in Amber 14 with CUDA (Compute Unified Device Architecture) accelerated PMEMD (algorithm for accelerated computation). 2 fs time step and SHAKE-enabled (algorithm for accelerated computation with fixed hydrogen atoms) setting were used for all equilibration and production stages, and a Berendsen thermostat was used for temperature control. Simulation frame was saved every 250 ps. Resulted trajectories were further analyzed with cpptraj. Conformational clusters of hSPX were calculated using Ca RMSD of hSPX (2-13) with 2.5 Å as threshold. Representative conformation of each cluster was used to define secondary structural components. Among representative conformers, the one belonged to the largest β cluster was used as reference structure of β conformer. Each frame of hSPX was compared with hSPX α-helix conformer solved by NMR and hSPX β-hairpin conformer predicted by MD simulation in terms of Ca RMSD of Trp2 to Lys11. A folding event of α-helix or β-hairpin was reached if Ca RMSD of Trp2 to Lys11 was less than 2.5 Å. In folding trajectory analysis, each frame was compared with gSPX α-helix conformer and the hSPX βαβ conformer in terms of main-chain atom RMSD of hSPX (2-13). A folding event of a or βαβ conformation was reached if the RMSD was less than 2.5 Å compared with reference structures. Folding time was defined as how long it took from end of last folding event to start of current folding event, while unfolding time was defined as how long it stayed in current folding event.

NMR Analysis

NMR experiments were performed in $H_2O:D_2O$ (90:10) with 5 mM sample concentration solvent at 298° K. For TOCSY experiments, the mixing time was 70 ms; while for NOESY, it was 500 ms. Data was acquired with Avance 600 MHz NMR Spectrometry (Bruker, Germany) in Shanghai Jiao Tong University. Data analysis were done with CcpNmr Analysis (version 2.4.2).

Peptide Synthesis and Characterization

All peptides used in this study were synthesized by Scilight Biotechnology LLC (Beijing, China) with standard solid-phase peptide synthesis procedures. Cyclic peptides (<1 mg/mL) were generated by oxidation in 20% dimethyl sulfoxide (DMSO) with overnight incubation. All peptides were characterized by MALDI-MS spectrum in Department of Chemistry, Hong Kong Baptist University.

Receptor Activation Assay

The hGalR1, hGalR2, hGalR3, and SRE-Luc plasmids were provided by Yingrun Biotechnology Co., Ltd (Changsha, China), while $G_{qi}$ plasmids were gifts from Prof. Jae Young Seong. HEK293 cells were cultured regularly in Dulbecco's Modified Eagle's Medium (DMEM) containing 10% fetal bovine serum (FBS) and seeded into 24-well plates with 50,000 cells per well. After being cultured for 24 h, the seeded cells were transiently transfected with equal amount of hGalR-, $G_{\alpha i}$-, and SRE-Luc plasmids by using Lipofectamine 3000 (Thermo Fisher Scientific, USA). Eighteen hours ahead of drug treatment, the medium was changed to serum-free medium. Cells were lysed after 6 h drug treatment, and the cell lysates were centrifuged at 13,000 rpm for 10 mins. 20 μL supernatant was subject to luciferase assay using Dual-Luciferase® Reporter Assay System (Promega, Madison, Wis., USA).

Serum Stability Assay

750 μL RPMI medium 1640 (Thermo Fisher Scientific) was mixed with 250 pt rat serum, and incubated at 37° C. for 15 min before adding peptide. The peptide dissolved in water was added into the reaction buffer to make a final concentration of 100 μg/mL. At each time point (5, 15, 30, 60, 120, 240, and 480 min), 100 μL reaction solution were taken, and mixed with 200 μL 6% trichloroacetic acid (TCA, Sigma-Aldrich). The resulting cloudy solution was cooled at 4° C. for 15 min, and centrifuged for 10 mins at 13,000 rpm. The supernatant was then analyzed by RP-HPLC. The extent of intact peptide was calculated based on the peak area and was normalized using a control sample.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extent. All publications cited herein are hereby incorporated by reference in their entirety.

INDUSTRIAL APPLICABILITY

Provided herein are cyclic peptide agonists toward human galanin receptor 2 (GalR2) and galanin receptor 3 (GalR3) useful in the treatment of GalR2 and GalR3 related and spexin-deficient disorders. In particular, the cyclic peptides and derivatives thereof are potent spexin and hGAL analogs with prolonged action, which are novel therapies for GalR2, GalR3 spexin-deficient disorders, such as obesity.

We claim:

1. A peptide comprising a sequence having at least 92.8% homology with SEQ ID NO: 23 or SEQ ID NO: 24; or having at least 93.7% homology with SEQ ID NO: 25 or a therapeutically effective salt thereof, wherein R1 is hydrogen, alkyl, or acyl with the proviso that SEQ ID NO: 23 must contain cysteine at position one and position thirteen of SEQ ID NO: 23; SEQ ID NO: 24 must contain cysteine at position four and position thirteen of SEQ ID NO: 24; and SEQ ID NO: 25 must contain cysteines at position one and position thirteen of SEQ ID NO: 25.

2. The peptide of claim 1, wherein R1 is hydrogen, $(C_1$-$C_6)$alkyl, or $(C_1$-$C_6)$acyl.

3. The peptide of claim 1, wherein R1 is hydrogen or $(C_1$-$C_3)$acyl.

4. The peptide of claim 1, wherein R1 is hydrogen or acetyl.

5. The peptide of claim 1 comprising SEQ ID NO: 23; SEQ ID NO: 24; or SEQ ID NO: 25.

6. The peptide of claim 5, wherein R1 is hydrogen, $(C_1$-$C_6)$alkyl, or $(C_1$-$C_6)$acyl.

7. The peptide of claim 5, wherein R1 is hydrogen or $(C_1$-$C_3)$acyl.

8. The peptide of claim 5, wherein R1 is hydrogen or acetyl.

9. A peptide consisting of SEQ ID NO: 23; SEQ ID NO: 24; or SEQ ID NO: 25 or a therapeutically effective salt thereof, wherein R1 is hydrogen, alkyl, or acyl.

10. The peptide of claim 9, wherein R1 is hydrogen, $(C_1\text{-}C_6)$alkyl, or $(C_1\text{-}C_6)$acyl.

11. The peptide of claim 9, wherein the peptide is SEQ ID NO: 6; SEQ ID NO: 7; SEQ ID NO: 8; SEQ ID NO: 10; or SEQ ID NO: 11.

12. A pharmaceutical composition comprising a peptide of claim 1 and at least one pharmaceutically acceptable excipient.

13. A method of treating a spexin-deficient disorder in a patient in need thereof comprising the step of administering a therapeutically effective amount of a peptide of claim 1 to the patient, wherein the spexin-deficient disorder is selected from the group consisting of obesity, type-II diabetes, non-alcoholic fatty liver disease and constipation.

14. The method of claim 13, wherein the peptide comprises SEQ ID NO: 23; SEQ ID NO: 24; or SEQ ID NO: 25; or a therapeutically acceptable salt thereof.

15. The method of claim 13, wherein the peptide is SEQ ID NO: 6; SEQ ID NO: 7; SEQ ID NO: 8; SEQ ID NO: 10; or SEQ ID NO: 11; or a therapeutically acceptable salt thereof.

16. The method of claim 13, wherein the spexin-deficient disorder is obesity.

17. The method of claim 13, wherein the peptide is administered to the patient intraperitoneally.

18. The method of claim 16, wherein the peptide comprises SEQ ID NO: 23; SEQ ID NO: 24; or SEQ ID NO: 25; or a therapeutically acceptable salt thereof.

19. The method of claim 16, wherein the peptide is SEQ ID NO: 6; SEQ ID NO: 7; SEQ ID NO: 8; SEQ ID NO: 10; or SEQ ID NO: 11; or a therapeutically acceptable salt thereof.

* * * * *

SEQUENCE LISTING

```
<160> NUMBER OF SEQ ID NOS: 25

<210> SEQ ID NO 1
<211> LENGTH: 30
<212> TYPE: PRT
<213> ORGANISM: human
<220> FEATURE:
<221> NAME/KEY: AMIDATION
<222> LOCATION: (30)..(30)
<223> OTHER INFORMATION: The C-terminal is amidated

<400> SEQUENCE: 1

Gly Trp Thr Leu Asn Ser Ala Gly Tyr Leu Leu Gly Pro His Ala Val
1               5                   10                  15

Gly Asn His Arg Ser Phe Ser Asp Lys Asn Gly Leu Thr Ser
            20                  25                  30

<210> SEQ ID NO 2
<211> LENGTH: 14
<212> TYPE: PRT
<213> ORGANISM: human
<220> FEATURE:
<221> NAME/KEY: AMIDATION
<222> LOCATION: (14)..(14)
<223> OTHER INFORMATION: The C-terminal is amidated

<400> SEQUENCE: 2

Asn Trp Thr Pro Gln Ala Met Leu Tyr Leu Lys Gly Ala Gln
1               5                   10

<210> SEQ ID NO 3
<211> LENGTH: 14
<212> TYPE: PRT
<213> ORGANISM: Artificial Sequence
<220> FEATURE:
<223> OTHER INFORMATION: hSPX with the amino acid at position one
      replaced by cysteine, Synthesized in the Lab
<220> FEATURE:
<221> NAME/KEY: AMIDATION
<222> LOCATION: (14)..(14)
<223> OTHER INFORMATION: The C-terminal is amidated
```

```
<400> SEQUENCE: 3

Cys Trp Thr Pro Gln Ala Met Leu Tyr Leu Lys Gly Ala Gln
1               5                   10

<210> SEQ ID NO 4
<211> LENGTH: 14
<212> TYPE: PRT
<213> ORGANISM: Artificial Sequence
<220> FEATURE:
<223> OTHER INFORMATION: hSPX with the amino acid at position four
      replaced by cysteine, Synthesized in the Lab
<220> FEATURE:
<221> NAME/KEY: AMIDATION
<222> LOCATION: (14)..(14)
<223> OTHER INFORMATION: The C-terminal is amidated

<400> SEQUENCE: 4

Asn Trp Thr Cys Gln Ala Met Leu Tyr Leu Lys Gly Ala Gln
1               5                   10

<210> SEQ ID NO 5
<211> LENGTH: 14
<212> TYPE: PRT
<213> ORGANISM: Artificial Sequence
<220> FEATURE:
<223> OTHER INFORMATION: hSPX with the amino acid at position thirteen
      replaced by cysteine, Synthesized in the Lab
<220> FEATURE:
<221> NAME/KEY: AMIDATION
<222> LOCATION: (14)..(14)
<223> OTHER INFORMATION: The C-terminal is amidated

<400> SEQUENCE: 5

Asn Trp Thr Pro Gln Ala Met Leu Tyr Leu Lys Gly Cys Gln
1               5                   10

<210> SEQ ID NO 6
<211> LENGTH: 14
<212> TYPE: PRT
<213> ORGANISM: Artificial Sequence
<220> FEATURE:
<223> OTHER INFORMATION: hSPX incorporating mutagenesis (LH101),
      Synthesized in the Lab
<220> FEATURE:
<221> NAME/KEY: DISULFID
<222> LOCATION: (1)..(13)
<223> OTHER INFORMATION: The side chain of C in positions one and
      thirteen are covalently bonded via a disulfide bond
<220> FEATURE:
<221> NAME/KEY: AMIDATION
<222> LOCATION: (14)..(14)
<223> OTHER INFORMATION: The C-terminal is amidated

<400> SEQUENCE: 6

Cys Trp Thr Pro Gln Ala Met Leu Tyr Leu Lys Gly Cys Gln
1               5                   10

<210> SEQ ID NO 7
<211> LENGTH: 14
<212> TYPE: PRT
<213> ORGANISM: Artificial Sequence
<220> FEATURE:
<223> OTHER INFORMATION: hSPX incorporating mutagenesis (LH102),
      Synthesized in the Lab
<220> FEATURE:
<221> NAME/KEY: DISULFID
<222> LOCATION: (4)..(13)
<223> OTHER INFORMATION: The side chain of C in positions four and
      thirteen are covalently bonded via a disulfide bond
<220> FEATURE:
<221> NAME/KEY: AMIDATED
```

```
<222> LOCATION: (14)..(14)
<223> OTHER INFORMATION: The C-terminal is amidated

<400> SEQUENCE: 7

Asn Trp Thr Cys Gln Ala Met Leu Tyr Leu Lys Gly Cys Gln
1               5                   10

<210> SEQ ID NO 8
<211> LENGTH: 14
<212> TYPE: PRT
<213> ORGANISM: Artificial Sequence
<220> FEATURE:
<223> OTHER INFORMATION: hSPX incorporating mutagenesis (LH101(Ac)),
      Synthesized in the Lab
<220> FEATURE:
<221> NAME/KEY: ACYLATED
<222> LOCATION: (1)..(1)
<223> OTHER INFORMATION: The N-terminal is acylated
<220> FEATURE:
<221> NAME/KEY: DISULFIDE
<222> LOCATION: (1)..(13)
<223> OTHER INFORMATION: The side chain of C in positions one and
      thirteen are covalently bonded via a disulfide bond
<220> FEATURE:
<221> NAME/KEY: AMIDATED
<222> LOCATION: (14)..(14)
<223> OTHER INFORMATION: The C-terminal is amidated

<400> SEQUENCE: 8

Cys Trp Thr Pro Gln Ala Met Leu Tyr Leu Lys Gly Cys Gln
1               5                   10

<210> SEQ ID NO 9
<211> LENGTH: 16
<212> TYPE: PRT
<213> ORGANISM: human
<220> FEATURE:
<221> NAME/KEY: AMIDATED
<222> LOCATION: (16)..(16)
<223> OTHER INFORMATION: The C-terminal is amidated

<400> SEQUENCE: 9

Gly Trp Thr Leu Asn Ser Ala Gly Tyr Leu Leu Gly Pro His Ala Val
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: hGAL(1-16) incorporating mutagenesis (LH201),
      Synthesized in the Lab
<220> FEATURE:
<221> NAME/KEY: DISULFID
<222> LOCATION: (1)..(13)
<223> OTHER INFORMATION: the side chain of C in positions one and
      thirteen are covalently bonded via a disulfide bond
<220> FEATURE:
<221> NAME/KEY: AMIDATED
<222> LOCATION: (16)..(16)
<223> OTHER INFORMATION: The C-terminal is amidated

<400> SEQUENCE: 10

Cys Trp Thr Leu Asn Ser Ala Gly Tyr Leu Leu Gly Cys His Ala Val
1               5                   10                  15

<210> SEQ ID NO 11
<211> LENGTH: 16
<212> TYPE: PRT
<213> ORGANISM: Artificial Sequence
<220> FEATURE:
```

```
<223> OTHER INFORMATION: hGAL(1-16) incorporating mutagenesis
      (LH201(Ac)), Synthesized in the Lab
<220

```
<213> ORGANISM: Artificial Sequence
<220> FEATURE:
<223> OTHER INFORMATION: hSPX with the amino acid at position six
      replaced by cysteine, Synthesized in the Lab
<220> FEATURE:
<221> NAME/KEY: AMIDATED
<222> LOCATION: (14)..(14)
<223> OTHER INFORMATION: The C-terminal is amidated

<400> SEQUENCE: 15

Asn Trp Thr Pro Gln Cys Met Leu Tyr Leu Lys Gly Ala Gln
1               5                   10

<210> SEQ ID NO 16
<211> LENGTH: 14
<212> TYPE: PRT
<213> ORGANISM: Artificial Sequence
<220> FEATURE:
<223> OTHER INFORMATION: hSPX with the amino acid at position seven
      replaced by cysteine, Synthesized in the Lab
<220> FEATURE:
<221> NAME/KEY: AMIDATED
<222> LOCATION: (14)..(14)
<223> OTHER INFORMATION: The C-terminal is amidated

<400> SEQUENCE: 16

Asn Trp Thr Pro Gln Ala Cys Leu Tyr Leu Lys Gly Ala Gln
1               5                   10

<210> SEQ ID NO 17
<211> LENGTH: 14
<212> TYPE: PRT
<213> ORGANISM: Artificial Sequence
<220> FEATURE:
<223> OTHER INFORMATION: hSPX with the amino acid at position eight
      replaced by cysteine, Synthesized in the Lab
<220> FEATURE:
<221> NAME/KEY: AMIDATED
<222> LOCATION: (14)..(14)
<223> OTHER INFORMATION: The C-terminal is amidated

<400> SEQUENCE: 17

Asn Trp Thr Pro Gln Ala Met Cys Tyr Leu Lys Gly Ala Gln
1               5                   10

<210> SEQ ID NO 18
<211> LENGTH: 14
<212> TYPE: PRT
<213> ORGANISM: Artificial Sequence
<220> FEATURE:
<223> OTHER INFORMATION: hSPX with the amino acid at position nine
      replaced by cysteine, Synthesized in the Lab
<220> FEATURE:
<221> NAME/KEY: AMIDATED
<222> LOCATION: (14)..(14)
<223> OTHER INFORMATION: The C-terminal is amidated

<400> SEQUENCE: 18

Asn Trp Thr Pro Gln Ala Met Leu Cys Leu Lys Gly Ala Gln
1               5                   10

<210> SEQ ID NO 19
<211> LENGTH: 14
<212> TYPE: PRT
<213> ORGANISM: Artificial Sequence
<220> FEATURE:
<223> OTHER INFORMATION: hSPX with the amino acid at position ten
      replaced by cysteine, Synthesized in the Lab
<220> FEATURE:
<221> NAME/KEY: AMIDATED
<222> LOCATION: (14)..(14)
```

```
<223> OTHER INFORMATION: The C-terminal is amidated

<400> SEQUENCE: 19

Asn Trp Thr Pro Gln Ala Met Leu Tyr Cys Lys Gly Ala Gln
1               5                   10

<210> SEQ ID NO 20
<211> LENGTH: 14
<212> TYPE: PRT
<213> ORGANISM: Artificial Sequence
<220> FEATURE:
<223> OTHER INFORMATION: hSPX with the amino acid at position eleven
      replaced by cysteine, Synthesized in the Lab
<220> FEATURE:
<221> NAME/KEY: AMIDATED
<222> LOCATION: (14)..(14)
<223> OTHER INFORMATION: The C-terminal is amidated

<400> SEQUENCE: 20

Asn Trp Thr Pro Gln Ala Met Leu Tyr Leu Cys Gly Ala Gln
1               5                   10

<210> SEQ ID NO 21
<211> LENGTH: 14
<212> TYPE: PRT
<213> ORGANISM: Artificial Sequence
<220> FEATURE:
<223> OTHER INFORMATION: hSPX with the amino acid at position twelve
      replaced by cysteine, Synthesized in the Lab
<220> FEATURE:
<221> NAME/KEY: AMIDATED
<222> LOCATION: (14)..(14)
<223> OTHER INFORMATION: The C-terminal is amidated

<400> SEQUENCE: 21

Asn Trp Thr Pro Gln Ala Met Leu Tyr Leu Lys Cys Ala Gln
1               5                   10

<210> SEQ ID NO 22
<211> LENGTH: 14
<212> TYPE: PRT
<213> ORGANISM: Artificial Sequence
<220> FEATURE:
<223> OTHER INFORMATION: hSPX with the amino acid at position fourteen
      replaced by cysteine, Synthesized in the Lab
<220> FEATURE:
<221> NAME/KEY: AMIDATED
<222> LOCATION: (14)..(14)
<223> OTHER INFORMATION: The C-terminal is amidated

<400> SEQUENCE: 22

Asn Trp Thr Pro Gln Ala Met Leu Tyr Leu Lys Gly Ala Cys
1               5                   10

<210> SEQ ID NO 23
<211> LENGTH: 14
<212> TYPE: PRT
<213> ORGANISM: Artificial Sequence
<220> FEATURE:
<223> OTHER INFORMATION: hSPX incorporating mutagenesis, Synthesized in
      the Lab
<220> FEATURE:
<221> NAME/KEY: DISULFID
<222> LOCATION: (1)..(13)
<223> OTHER INFORMATION: The side chain of C in positions one and
      thirteen are covalently bonded via a linker
<220> FEATURE:
<221> NAME/KEY: misc_feature
<222> LOCATION: (1)..(1)
<223> OTHER INFORMATION: The N-terminal amine is represented by -NHR1
<220> FEATURE:
```

```
<221> NAME/KEY: AMIDATED
<222> LOCATION: (14)..(14)
<223> OTHER INFORMATION: The C-terminal is amidated

<400> SEQUENCE: 23

Cys Trp Thr Pro Gln Ala Met Leu Tyr Leu Lys Gly Cys Gln
1               5                   10

<210> SEQ ID NO 24
<211> LENGTH: 14
<212> TYPE: PRT
<213> ORGANISM: Artificial Sequence
<220> FEATURE:
<223> OTHER INFORMATION: hSPX incorporating mutagenesis, Synthesized in
      the Lab
<220> FEATURE:
<221> NAME/KEY: misc_feature
<222> LOCATION: (1)..(1)
<223> OTHER INFORMATION: The N-terminal amine is represented by -NHR1
<220> FEATURE:
<221> NAME/KEY: DISULFID
<222> LOCATION: (4)..(13)
<223> OTHER INFORMATION: The side chain of C in positions four and
      thirteen are covalently bonded via a linker
<220> FEATURE:
<221> NAME/KEY: AMIDATED
<222> LOCATION: (14)..(14)
<223> OTHER INFORMATION: The C-terminal is amidated

<400> SEQUENCE: 24

Asn Trp Thr Cys Gln Ala Met Leu Tyr Leu Lys Gly Cys Gln
1               5                   10

<210> SEQ ID NO 25
<211> LENGTH: 16
<212> TYPE: PRT
<213> ORGANISM: Artificial Sequence
<220> FEATURE:
<223> OTHER INFORMATION: hGAL(1-16) incorporating mutagenesis,
      Synthesized in the Lab
<220> FEATURE:
<221> NAME/KEY: DISULFID
<222> LOCATION: (1)..(13)
<223> OTHER INFORMATION: The side chain of C in positions one and
      thirteen are covalently bonded via a linker
<220> FEATURE:
<221> NAME/KEY: misc_feature
<222> LOCATION: (1)..(1)
<223> OTHER INFORMATION: The N-terminal amine is represented by -NHR1
<220> FEATURE:
<221> NAME/KEY: AMIDATED
<222> LOCATION: (16)..(16)
<223> OTHER INFORMATION: The C-terminal is amidated

<400> SEQUENCE: 25

Cys Trp Thr Leu Asn Ser Ala Gly Tyr Leu Leu Gly Cys His Ala Val
1               5                   10                  15
```